US011338065B2

(12) United States Patent
Bhatia et al.

(10) Patent No.: US 11,338,065 B2
(45) Date of Patent: May 24, 2022

(54) IN SITU EXPANSION OF ENGINEERED DEVICES FOR REGENERATION

(71) Applicants: Massachusetts Institute of Technology, Cambridge, MA (US); Trustees of Boston University, Boston, MA (US)

(72) Inventors: Sangeeta N. Bhatia, Lexington, MA (US); Kelly R. Stevens, Cambridge, MA (US); Christopher S. Chen, Newton, MA (US)

(73) Assignees: Massachusetts Institute of Technology, Cambridge, MA (US); Trustees of Boston University, Boston, MA (US)

( * ) Notice: Subject to any disclaimer, the term of this patent is extended or adjusted under 35 U.S.C. 154(b) by 0 days.

(21) Appl. No.: 15/765,526

(22) PCT Filed: Oct. 7, 2016

(86) PCT No.: PCT/US2016/055972
§ 371 (c)(1),
(2) Date: Apr. 3, 2018

(87) PCT Pub. No.: WO2017/062757
PCT Pub. Date: Apr. 13, 2017

(65) Prior Publication Data
US 2019/0076578 A1   Mar. 14, 2019

Related U.S. Application Data

(60) Provisional application No. 62/239,214, filed on Oct. 8, 2015.

(51) Int. Cl.
*A61L 27/52* (2006.01)
*A61L 27/38* (2006.01)
*A61L 27/22* (2006.01)

(52) U.S. Cl.
CPC .......... *A61L 27/52* (2013.01); *A61L 27/3804* (2013.01); *A61L 27/3808* (2013.01);
(Continued)

(58) Field of Classification Search
CPC ............. A61L 27/3804; A61L 27/3808; A61L 27/3886; A61L 27/52; A61L 27/3891; A61L 27/225; A61L 2430/28
See application file for complete search history.

(56) References Cited

U.S. PATENT DOCUMENTS 4,853,332 A    8/1989  Mark et al.
5,116,964 A    5/1992  Capon et al.
(Continued)

FOREIGN PATENT DOCUMENTS

EP    1083945 A1    3/2001
EP    1500697 A2    1/2005
(Continued)

OTHER PUBLICATIONS

Takebe et al. Engineering of human hepatic tissue with functional vascular networks. Organogenesis (Apr. 2014), 10(2), 260-267. (Year: 2014).*

(Continued)

*Primary Examiner* — Sean C. Barron
(74) *Attorney, Agent, or Firm* — McCarter & English, LLP

(57) ABSTRACT

Engineered human tissue seed constructs are provided that are suitable for implantation in subjects. Methods of making and using the engineered tissue seed constructs are provided.

29 Claims, 22 Drawing Sheets

(52) U.S. Cl.
CPC ....... *A61L 27/3886* (2013.01); *A61L 27/3891* (2013.01); *A61L 27/225* (2013.01); *A61L 2430/28* (2013.01)

(56) References Cited

U.S. PATENT DOCUMENTS

| | | | |
|---|---|---|---|
| 5,123,950 | A | 6/1992 | Homma et al. |
| 5,624,840 | A | 4/1997 | Naughton et al. |
| 5,712,161 | A | 1/1998 | Koezuka et al. |
| 6,368,612 | B1 | 4/2002 | Lanza et al. |
| 6,509,514 | B1 | 1/2003 | Kneteman et al. |
| 6,864,402 | B1 | 3/2005 | Rogler et al. |
| 6,995,299 | B2 | 2/2006 | Wu et al. |
| 7,273,963 | B2 | 9/2007 | Kneteman et al. |
| 7,498,479 | B2 | 3/2009 | Kneteman et al. |
| 7,626,075 | B2 | 12/2009 | Beschomer et al. |
| 8,852,932 | B2 | 10/2014 | Forgacs et al. |
| 10,004,826 | B2 | 6/2018 | Bhatia et al. |
| 10,072,257 | B2 | 9/2018 | Bhatia et al. |
| 10,260,039 | B2 | 4/2019 | Bhatia et al. |
| 10,426,870 | B2 | 10/2019 | Chen et al. |
| 2002/0182633 | A1 | 12/2002 | Chen et al. |
| 2003/0203003 | A1 | 10/2003 | Nelson et al. |
| 2004/0096966 | A1 | 5/2004 | Ingram |
| 2004/0121066 | A1 | 6/2004 | Anderson et al. |
| 2004/0126405 | A1 | 7/2004 | Sahatjian et al. |
| 2005/0053642 | A1 | 3/2005 | Ulbricht et al. |
| 2005/0169962 | A1 | 8/2005 | Bhatia et al. |
| 2006/0258000 | A1 | 11/2006 | Allen et al. |
| 2006/0270032 | A1 | 11/2006 | Bhatia et al. |
| 2008/0075750 | A1 | 3/2008 | Akins |
| 2008/0226604 | A9 | 9/2008 | Kellar et al. |
| 2008/0280360 | A1 | 11/2008 | Kaplan et al. |
| 2009/0018033 | A1 | 1/2009 | Morgan et al. |
| 2009/0035855 | A1 | 2/2009 | Ying et al. |
| 2009/0117655 | A1 | 5/2009 | Kubota et al. |
| 2009/0285892 | A1 | 11/2009 | Sakthivel et al. |
| 2009/0319033 | A1 | 12/2009 | Niklason et al. |
| 2010/0040584 | A1 | 2/2010 | Melero-Martin et al. |
| 2010/0099048 | A1 | 4/2010 | Thomas et al. |
| 2010/0168872 | A1 | 7/2010 | Brown et al. |
| 2010/0184220 | A1 | 7/2010 | Ram-Liebig et al. |
| 2010/0189712 | A1 | 7/2010 | L'Heureux et al. |
| 2010/0278798 | A1 | 11/2010 | Sia et al. |
| 2010/0285094 | A1* | 11/2010 | Gupta ............... A61L 15/60 424/429 |
| 2011/0035024 | A1 | 2/2011 | Malmquist et al. |
| 2012/0141547 | A1 | 6/2012 | Zhao et al. |
| 2012/0216304 | A1 | 8/2012 | Bhatia et al. |
| 2014/0212910 | A1 | 7/2014 | Bhatia et al. |
| 2015/0082468 | A1 | 3/2015 | Bhatia et al. |
| 2015/0087004 | A1 | 3/2015 | Chen et al. |
| 2015/0125507 | A1 | 5/2015 | Chen et al. |
| 2019/0376024 | A1 | 12/2019 | Bhatia et al. |
| 2020/0101201 | A1 | 4/2020 | Chen et al. |
| 2021/0213171 | A1 | 7/2021 | Chen et al. |
| 2021/0213173 | A1 | 7/2021 | Bhatia et al. |

FOREIGN PATENT DOCUMENTS

| | | |
|---|---|---|
| EP | 1939280 A1 | 7/2008 |
| WO | 94/08570 A1 | 4/1994 |
| WO | 1999/52573 A1 | 10/1999 |
| WO | 2004/046337 A2 | 6/2004 |
| WO | 2006001778 A1 | 1/2006 |
| WO | 08/148026 A1 | 12/2008 |
| WO | 2012/048170 A2 | 4/2012 |
| WO | 2014/011775 A1 | 1/2014 |

OTHER PUBLICATIONS

Maurice et al. Effects of Imidazole derivatives on cytochromes P450 from human hepatocytes in primary culture. FASEB J. (1992), 6, 752-758. (Year: 1992).*

Baudin et al. A protocol for isolation and culture of human umbilical vein endothelial cells. Nature Protocols (2007), 2(3), 481-485. (Year: 2007).*

Tamai et al. Characterization of a Liver Organoid Tissue Composed of Hepatocytes and Fibroblasts in Dense Collagen Fibrils. Tissue Engineering Part A (2013), 19(21), 2527-2535. (Year: 2013).*

Rnjak et al. Primary human dermal fibroblast interactions with open weave three-dimensional scaffolds prepared from synthetic human elastin. Biomaterials (2009), 30, 6469-6477. (Year: 2009).*

International Preliminary Report on Patentability, PCT/US2016/055972, dated Apr. 10, 2018, 6 pages.

International Search Report and Written Opinion, PCT/US2016/055972, dated Jan. 10, 2017, 8 pages.

U.S. Appl. No. 14/116,901, filed Apr. 14, 2014, Sangeeta N. Bhatia.
U.S. Appl. No. 16/358,160, filed Mar. 19, 2019, Sangeeta N. Bhatia.
U.S. Appl. No. 14/381,866, filed Aug. 28, 2014, Sangeeta N. Bhatia.
U.S. Appl. No. 14/593,555, filed Jan. 9, 2015, Christopher S. Chen.
U.S. Appl. No. 13/267,866, filed Oct. 6, 2011, Sangeeta N. Bhatia.
U.S. Appl. No. 14/116,901, Nov. 21, 2018.
U.S. Appl. No. 14/116,901, Mar. 9, 2018.
U.S. Appl. No. 14/116,901, Mar. 2, 2017.
U.S. Appl. No. 14/116,901, Jun. 17, 2016.
U.S. Appl. No. 14/116,901, Sep. 24, 2015.
U.S. Appl. No. 14/381,866, May 17, 2018.
U.S. Appl. No. 14/381,866, Apr. 26, 2017.
U.S. Appl. No. 14/381,866, Jun. 30, 2016.
U.S. Appl. No. 14/381,866, Nov. 18, 2015.
U.S. Appl. No. 14/593,555, Aug. 1, 2019.
U.S. Appl. No. 14/593,555, Nov. 26, 2018.
U.S. Appl. No. 14/593,555, Jan. 12, 2018.
U.S. Appl. No. 14/593,555, Jun. 5, 2018.
U.S. Appl. No. 14/593,555, Apr. 26, 2017.
U.S. Appl. No. 14/593,555, Nov. 18, 2016.
U.S. Appl. No. 14/593,555, Aug. 29, 2016.
U.S. Appl. No. 13/267,866, Mar. 8, 2018.
U.S. Appl. No. 13/267,866, Feb. 9, 2017.
U.S. Appl. No. 13/267,866, Mar. 21, 2016.
U.S. Appl. No. 13/267,866, Jul. 31, 2014.
U.S. Appl. No. 13/267,866, Aug. 5, 2013.
U.S. Appl. No. 13/267,866, Sep. 11, 2012.

Nikkhah, M. et al., "Directed Endothelial Cell Morphogenesis in Micropatterned Gelatin Methacrylate Hydrogels," Biomaterials, vol. 33(35): 9009-9018 (2012).

Takebe, T. et al., "Vascularized and functional human liver from an iPSC-derived organ bud transplant," Nature, vol. 499: 481-485 (2013).

Takebe, T. et al., "Generation of a vascularized and functional human liver from an iPSC-derived organ bud transplant," Nature Protocols, vol. 9 (2): 396-409 (2014).

Abu-Absi, S. F. et al., "Structural polarity and functional bile canaliculi in rat hepatocyte spheroids," Exp Cell Res., vol. 274(1):56-67 (2002).

Aird, W. C., "Endothelium in health and disease," Pharmacol Rep. vol. 60 (1):139-143 (2008).

Akselrod, G. M. et al., "Laser-guided assembly of heterotypic three-dimensional living cell microarrays," Biophys J., vol. 91 (1): 3465-3473 (2006).

Albrecht, D. R., et al. "Probing the role of multicellular organization in three-dimensional microenvironments," Nat Methods, vol. 3(5): 369-375 (2006).

Antonchuk, J. et al., "AggreWell 400 and AggreWell 800 Provide a Unique Platform for Generation of Size-Controlled Aggregates Including Human Embryoid Bodies," STEMCell Technologies, Poster Presentation, 1 page (2010).

Arcaute, K. et al., "Stereolithography of three-dimensional bioactive poly(ethylene glycol) constructs with encapsulated cells," Annals of Biomedical Engineering, vol. 34(9):1429-1441 (2006).

Atala, A., "Engineering organs," Curr Opin Biotechnol., vol. 20(5):575-592 (2009).

Azuma, Hisaya et al., "Robust expansion of human hepatocytes in Fah–/–/Rag2–/–/Il2rg–/– mice," Nature Biotechnology, vol. 25(8):903-910 (2007).

(56) References Cited

OTHER PUBLICATIONS

Baranski, J. et al., "Geometric control of vascular networks to enhance engineered tissue integration and function," PNAS, vol. 110(19): 7586-7591 (2013).
Barron, J. A, et al., "Biological laser printing: a novel technique for creating heterogeneous 3-dimensional cell patterns," Biomed Microdevices, vol. 6 (2):139-147 (2004).
Berry, M.N., et al., "High-yield preparation of isolated rat liver parenchymal cells: a biochemical and fine structural study," J. Cell Biol., vol. 43(3), pp. 506-520 (1969).
Bhatia, S. N., et al."Effect of cell-cell interactions in preservation of cellular phenotype: cocultivation of hepatocytes and nonparenchymal cells," FASEB J., vol. 13 (14):1883-1900 (1999).
Brophy, C. M. et al."Rat hepatocyte spheroids formed by rocked technique maintain differentiated hepatocyte gene expression and function," Hepatology vol. 49(2):578-586 (2009).
Cao, X. et al., "Differentiation and Functional Comparison of Monocytes and Macrophages from hiPSCs with Peripheral Blood Derivatives," Stem Cell Reports, vol. 12(6): 1282-1297 (2019).
Chan, V. et al., "Three-dimensional photopatterning of hydrogels using stereolithography for long-term cell encapsulation," Lab Chip, vol. 10: 2062-2070 (2010).
Chen, A. A., et al., "Humanized mice with ectopic artificial liver tissues," Proc Natl Acad Sci USA, vol. 108 (29):11842-11847 (2011).
Cho, C. et al., "Layered patterning of hepatocytes in co-culture systems using microfabricated stencils," Biotechniques, vol. 48(1): 47-52 (2010).
Cho, N-J., et al., "Viral infection of human progenitor and liver-derived cells encapsulated in three-dimensional PEG-based hydrogel," Biomedical Materials, vol. 4: 1-7 (2009).
Choi et al. "Patterning and transferring hydrogel-encapsulated bacterial cells for quantitative analysis of synthetically engineered genetic circuits." Biomaterials. Jan. 2012;33(2):624-33. doi: 10.1016/j.biomaterials.2011.09.069. Epub Oct. 19, 2011.
Cleaver, O.et al., "Endothelial signaling during development," Nat Med, vol. 9(6):661-668 (2003).
Culver, J. C., et al., "Three-dimensional biomimetic patterning in hydrogels to guide cellular organization," Adv Mater, vol. 24(17):2344-2348 (2012).
Deforest, C. A., et al.,"Cytocompatible click-based hydrogels with dynamically tunable properties through orthogonal photoconjugation and photocleavage reactions," Nat Chem., vol. 3(12):925-931 (2012).
Ding, B. S. et al., "Endothelial-derived angiocrine signals initiate and sustain regenerative lung alveolarization," Cell, vol. 147(3):539-553 (2011).
Ding, B. S. et al., "Inductive angiocrine signals from sinusoidal endothelium are required for liver regeneration," Nature, vol. 468(7321):310-315 (2010).
Douglas, E. et al., "Self-assembled cellular microarrays patterned using DNA barcodes," Lab On A Chip, vol. 7(11), 7 pages (2007).
Du, Y, et al., "Directed assembly of cell-laden microgels for fabrication of 3D tissue constructs," Proc Natl Acad Sci USA, vol. 105(28):9522-9527 (2008).
Dunn, J. C., et al., "Long-term in vitro function of adult hepatocytes in a collagen sandwich configuration," Biotechnol Prog., vol. 7(3):237-245 (1991).
Ennett, A. B. et al., "Tissue engineering strategies for in vivo neovascularisation," Expert Opin Biol Ther., vol. 2 (8):805-818 (2002).
Francipane, M. et al., "Maturation of embryonic tissues in a lymph node: a new approach for bioengineering complex organs," Organogenesis, vol. 10 (3):323-331(2014).
Franses, J. W., et al., "Stromal endothelial cells directly influence cancer progression," Sci Transl Med., vol. 3 (66):66ra5, 18 pages (2011).
Gartner, Z. J., et al. "Programmed assembly of 3-dimensional microtissues with defined cellular connectivity" PNAS, vol. 106(12), pp. 4606-4610 (2009).
Glicklis, R., et al., "Hepatocyte behavior within three-dimensional porous alginate scaffolds," Biotechnol Bioeng., vol. 67(3), 344-353 (2000).
Hamada, H., "In search of Turing in vivo: understanding Nodal and Lefty behavior," Dev Cell, vol. 22(5): 911-912 (2012).
He, J. Q. et al., "Human embryonic stem cells develop into multiple types of cardiac myocytes: action potential characterization," Circ Res., vol. 93(1): 32-39 (2003).
Hsiao, S. C.; "Direct Cell Surface Modification with DNA for the Capture of Primary Cells and the Investigation of Myotube Formation on Defined Patterns," Langmuir, vol. 25(12), pp. 6985-6991(2009).
Hui, E. et al., "Micromechanical control of cell-cell interactions," Proc Natl Acad Sci USA, vol. 104(14):5722-5726 (2007).
Inman, J. L. et al., "Apical polarity in three-dimensional culture systems: where to now?," J Biol., vol. 9(1): 2 (2010).
International Preliminary Report on Patentability for Application No. PCT/US2011/055179, 12 pages, dated Apr. 9, 2013.
International Preliminary Report on Patentability, PCT/US2012/037656, dated Nov. 12, 2013, 9 pages.
International Preliminary Report on Patentability, PCT/US2013/028345, dated Sep. 2, 2014, 6 pages.
International Search Report and Written Opinion for Application No. PCT/US2011/055179, 17 pages, dated May 23, 2012.
International Search Report and Written Opinion, PCT/US2012/037656, dated Oct. 17, 2012, 9 pages.
International Search Report and Written Opinion, PCT/US2013/028345, dated May 24, 2013, 9 pages.
Invitation to Pay Additional Fees, and, Where Applicable, Protest Fee for Application No. PCT/US2011/055179, 5 pages, dated Feb. 13, 2012.
Jakab, K, et al., "Engineering biological structures of prescribed shape using self-assembling multicellular systems," Proc Natl Acad Sci USA, vol. 101(9):2864-2869 (2004).
Jakab, K., et al., "Tissue engineering by self-assembly and bio-printing of living cells," Biofabrication, vol. 2(2): 022001 (2010).
Kachouie, N. et al., "Directed assembly of cell-laden hydrogels for engineering functional tissues," Organogenesis, pp. 234-244 (2010) <URL:http://ukpmc.ac.uk/articles/PMC3055649 /pdf/org0604 0234.pdf> [retrieved on Oct. 2, 2012].
Kaji, H. et al., "Engineering systems for the generation of patterned co-cultures for controlling cell-cell interactions," Biochim Biophys Acta, vol. 1810(3): 239-250 (2011).
Kaufmann, P.M. et al., "Highly Porous Polymer Matrices as a Three-dimensional Culture System for Hepatocytes," Cell Transplantation, vol. 6(5):463-468 (1997).
Khademhosseini, Ali et al., "Progress in Tissue Engineering," Scientific American, vol. 300:64-71 (2009).
Khetani, S. R., et al., "Microscale culture of human liver cells for drug development," Nat Biotechnol., vol. 26 (1):120-126 (2008).
Khetani, Salman R. et al., "Exploring Interactions Between Rat Hepatocytes and Nonparenchymal Cells Using Gene Expression Profiling," Hepatology, vol. 40:545-554 (2004).
Khetani, SR et al., "T-cadherin modulates hepatocyte functions in vitro," FASEB J vol. 22(11):3768-3775 (2008).
Kloxin, A. M., et al."Photodegradable hydrogels for dynamic tuning of physical and chemical properties," Science, vol. 324(5293): 59-63 (2009).
Kneser, Ulrich et al., "Long-term differentiated function of heterotopically transplanted hepatocytes on three-dimensional polymer matrices," J. Biomed. Mater. Res., vol. 47:494-503 (1999).
Komori, J. et al., "the mouse lymph node as an ectopic transplantation site for multiple tissues," Nature Biotechnology, vol. 30(10):976-985 (2012).
Lammert, E., et al., "Induction of pancreatic differentiation by signals from blood vessels," Science, vol. 294(5542): 564-567 (2001).
Lammert, E., et al., "Role of endothelial cells in early pancreas and liver development," Mech Dev., vol. 120(1): 59-64 (2003).
Landry, J., et al., "Spheroidal aggregate culture of rat liver cells: histotypic reorganization, biomatrix deposition, and maintenance of functional activities," J Cell Biol, vol. 101(3): 914-923 (1985).

(56) References Cited

OTHER PUBLICATIONS

Lang, H. et al., "Transplantation of Mouse Embryonic Stem Cells into the Cochlea of an Auditory-Neuropathy Animal Model: Effects of Timing after Injury," JARO, vol. 9: 225-240 (2008).
Laube, F. et al., "Reprogramming of newt cardiomyocytes is induced by tissue regeneration," Journal of Cell Science, vol. 119 (22):4719-4729 (2006).
Lee, H. et al., "Local Delivery of Basic Fibroblast Growth Factor Increases Both Angiogenesis and Engraftment of Hepatocytes in Tissue-Engineered Polymer Devices," Transplantation, vol. 73:1589-1593 (2002).
Levenberg, S. et al., "Engineering vascularized skeletal muscle tissue," Nat Biotechnol., vol. 23(7): 879-884 (2005).
Li, C. et al. "DNA-templated assembly of droplet-derived PEG microtissues," Lab On A Chip, vol. 11(17), 9 pages ( 2011).
Li, G. et al., "The dose of growth factors influences the synergistic effect of vascular endothelial growth factor on bone morphogenetic protein 4-induced ectopic bone formation," Tissue Engineering, vol. 15(8) 2123-2133 (2009).
Liu, Valerie A. et al., "Three-Dimensional Photopatterning of Hydrogels Containing Living Cells," Biomedical Microdevices, vol. 4(4):257-266 (2002).
Lu, H. F. et al., "Three-dimensional co-culture of rat hepatocyte spheroids and NIH/3T3 fibroblasts enhances hepatocyte functional maintenance," Acta Biomater., vol. 1(4):399-410 (2005).
MacNeil, S., "Progress and opportunities for tissue-engineered skin," Nature vol. 445(7130):874-880 (2007).
Mailleux, A. A., et al., "Lumen formation during mammary epithelial morphogenesis: insights from in vitro and in vivo models," Cell Cycle, vol. 7 (1) :57-62 (2008).
March, S., et al., "Microenvironmental regulation of the sinusoidal endothelial cell phenotype in vitro,"Hepatology, vol. 50(3):920-928 (2009).
Matsumoto, K., "Liver organogenesis promoted by endothelial cells prior to vascular function," Science, vol. 294 (5542):559-563 (2001).
Matsumura, T. et al., "Establishment of an immortalized human-liver endothelial cell line with SV40T and hTERT," Transplantation, vol. 77(9):1357-1365 (2004).
Mei, J. et al., "Improved survival of fulminant liver failure by transplantation of microencapsulated cryopreserved porcine hepatocytes in mice," Cell Transplantation, vol. 18:101-110 (2009).
Mikos, A. G., et al., "Engineering Complex Tissues," Tissue Eng vol. 12 (12): 3307-3339(2006).
Miller, J. S., et al. "Rapid casting of patterned vascular networks for perfusable engineered 3D tissues," Nat Mater., vol. 11(9): 768-774 (2012).
Mironov, V., et al., "Organ printing: computer-aided jet-based 3D tissue engineering.," Trends Biotechnol., vol. 21 (4): 157-161 (2003).
Moscona, A., "Rotation-mediated histogenetic aggregation of dissociated cells. A quantifiable approach to cell interactions in vitro," Exp Cell Res., vol. 22:455-475 (1961).
Mueller, P., et al., "Differential diffusivity of Nodal and Lefty underlies a reaction-diffusion patterning system," Science, vol. 336(6082): 721-724(2012).
Mueller, P., et al., "Extracellular movement of signaling molecules," Dev Cell., vol. 21(1): 145-158 (2011).
Nahmias, Y., et al., "Integration of technologies for hepatic tissue engineering,"Adv Biochem Eng Biotechnol., vol. 103:309-329 (2006).
Nahmias, Y., et al., "Laser-guided direct writing for three-dimensional tissue engineering," Biotechnol Bioeng., vol. 92 (2):129-136 (2005).
Nelson, C. et al., "Microstructured extracellular matrices in tissue engineering and development," Current Opinion in Biotechnology, vol. 17:518-523 (2006).
Nelson, C. M., et al., "Tissue geometry determines sites of mammary branching morphogenesis in organotypic cultures," Science, vol. 314(5797): 298-300 (2006).
Nomi, M. et al., "Principals of neovascularization for tissue engineering," Molecular Aspects of Med., vol. 23: 463-483 (2002).
Ohashi, Kazuo et al., "Liver Tissue Engineering at Extrahepatic Sites in Mice as a Potential New Therapy for Genetic Liver Diseases," Hepatology, vol. 41:132-140 (2005).
Panda, P. et al., Stop-flow lithography to generate cell-laden microgel particles, Lab on a Chip, vol. 8(7):1056-1061 (2008).
Parenteau, N. L., "Commercial development of cell-based therapeutics: strategic considerations along the drug to tissue spectrum," Regen Med., vol. 4(4): 601-611 (2009).
Peshwa, M. V., et al., "Mechanistics of formation and ultrastructural evaluation of hepatocyte spheroids," In Vitro Cell Dev Biol Anim., vol. 32(4): 197-203 (1996).
Qiu et al. "Generation of Uniformly Sized Alginate Microparticles for Cell Encapsulation by Using a Soft-Lithography Approach." Advanced Materials 19.12 (2007): 1603-1607.
Raghavan, S. et al., "Geometrically Controlled Endothelial Tubulogenesis in Micropatterned Gels," Tissue Engineering: Part A, vol. 16 (7): 2255-2263 (2010).
Rago, A. P., et al., "Encapsulated Arrays of Self-Assembled Microtissues: An Alternative to Spherical Microcapsules," Tissue Eng Part A 15, 387-395 (2009).
Ramanan, V. et al., "Engineered ectopic human livers organize and proliferate in vivo in response to regenerative cues," BMES, 1 page (2015).
Sakai, Y., et al., "A new bioartificial liver using porcine hepatocyte spheroids in high-cell-density suspension perfusion culture: in vitro performance in synthesized culture medium and in 100% human plasma.," Cell Transplant, vol. 8 (5):531-541 (1999).
Schwartz, R.E., et al., "Modeling hepatitis C virus infection using human induced pluripotent stem cells," Proc Natl Acad Sci USA, vol. 109(7):2544-2548 (2012).
Seglen, P. O., "Preparation of isolated rat liver cells," Methods Cell Biol., vol. 13: 29-83 (1976).
Seo, S. et al., "Enhanced liver functions of hepatocytes cocultured with NIH 3T3 in the alginate/galactosylated chitosan scaffold," Biomaterials, vol. 27: 1487-1495 (2007).
Si-Tayeb, K. et al., "Highly efficient generation of human hepatocyte-like cells from induced pluripotent stem cells," Hepatology, vol. 51(1): 297-305 (2010).
Stevens KR, et al., "InVERT molding for scalable control of tissue microarchitecture," Nat Commun., vol. 4 (1847) doi:10.1038/ncomms2853 (2013).
Stevens, K. R et al., "Physiological function and transplantation of scaffold-free and vascularized human cardiac muscle tissue," Proc Natl Acad Sci USA., vol. 106(39): 16568-16573 (2009).
Stevens, Molly M. et al., "In vivo engineering of organs: The bone bioreactor," PNAS, vol. 102(32):11450-11455 (2005).
Takahashi K. et al., "Induction of pluripotent stem cells from mouse embryonic and adult fibroblast cultures by defined factors," Cell, vol. 126 (4): 663-676 (2006).
Tan, W. et al., "Layer-by-layer microfluidics for biomimetic three-dimensional structures," Biomaterials, vol. 25 (7-8):1355-1364, (2004).
Tateno, Chise et al., "Near Completely Humanized Liver in Mice Shows Human-Type Metabolic Responses to Drugs," American Journal of Pathology, vol. 165(3):901-912 (2004).
Tekin, H., et al., "Responsive micromolds for sequential patterning of hydrogel microstructures," J Am Chem Soc., vol. 133(33): 12944-12947 (2011).
Tsang, L. V et al., "Three-dimensional tissue fabrication," Advanced Drug Delivery Reviews, Elsevier BV, Amsterdam, NL, vol. 56(11):1635-1647 (2004).
Tsang, L.V. et al., "Fabrication of 3D hepatic tissues by additive photopatterning of cellular hydrogels," FASEB J., vol. 21(3): 790-801 (2007).
Tsuda, Y. et al., "Cellular control of tissue architectures using a three-dimensional tissue fabrication technique," Biomaterials, vol. 28(33): 4939-4946 (2007).
Ulbricht, J. et al., "On the biodegradability of polyethylene glycol, polypeptides and poly(2-oxazoline)s," Biomaterials, vol. 35:4848-4861 (2014).
Underhill, G. H. et al., "Assessment of hepatocellular function within PEG hydrogels," Biomaterials, vol. 28(2):256-270 (2007).

(56) References Cited

OTHER PUBLICATIONS

Ungrin, M. D., et al., "Reproducible, Ultra High-Throughput Formation of Multicellular Organization from Single Cell Suspension-Derived Human Embryonic Stem Cell Aggregates," PLoS One vol. 3 (2):e1565(2008).
Uyama, Shiro et al., "Hepatocyte Transplantation Using Biodegradable Matrices in Ascorbic Acid-deficient Rats: Comparison with Heterotopically Transplanted Liver Grafts," Transplantation, vol. 71(9):1226-1231 (2001).
Valignat, M-P., et al., "Reversible self-assembly and directed assembly of DNA-linked micrometer-sized colloids," PNAS, vol. 102(12), pp. 4225-4229 (2005).
Vanbuskirk, Kelley M. et al., "Preerythrocytic, live-attenuated Plasmodium falciparum vaccine candidates by design," PNAS, vol. 106(31):13004-13009 (2009).
Williams, C. M. et al., "Autocrine-Controlled Formation and Function of Tissue-Like Aggregates by Primary Hepatocytes in Micropatterned Hydrogel Arrays," Tissue Eng Part A vol. 17 (7-8), 1055-1068 (2011).
Wong, S. F., et al., "Concave microwell based size-controllable hepatosphere as a three-dimensional liver tissue model," Biomaterials, vol. 32(32):8087-8096 (2011).
Wylie, R. G. et al., "Spatially controlled simultaneous patterning of multiple growth factors in three-dimensional hydrogels," Nat Mater., vol. 10 (10): 799-806 (2011).
Yokoyama, T. et al., "In Vivo Engineering of Metabolically Active Hepatic Tissues in a Neovascularized Subcutaneous Cavity," American Journal of Transplantation, vol. 6:50-59 (2006).
Zhang, S. C. et al., "In vitro differentiation of transplantable neural precursors from human embryonic stem cells," Nat Biotechnol., vol. 19(12): 1129-1133(2001).
Zhou, J. et al., "Neural cell injury microenvironment induces neural differentiation of human umbilical cord mesenchymal stem cells," Neural Regen Res., vol. 7(34): 2689-2697 (2012).
Au et al., Bone marrow-derived mesenchymal stem cells facilitate engineering of long-lasting functional vasculature. Blood. May 1, 2008;111(9):4551-8.
Chen et al., Prevascularization of a fibrin-based tissue construct accelerates the formation of functional anastomosis with host vasculature. Tissue Eng Part A. Jun. 2009;15(6):1363-71.
Chen et al., Rapid anastomosis of endothelial progenitor cell-derived vessels with host vasculature is promoted by a high density of cotransplanted fibroblasts. Tissue Eng Part A. Feb. 2010;16(2):585-94.
Chen et al., Spatio-temporal VEGF and PDGF delivery patterns blood vessel formation and maturation. Pharm Res. Feb. 2007;24(2):258-64.
Cheng et al., Engineered blood vessel networks connect to host vasculature via wrapping-and-tapping anastomosis. Blood. Oct. 27, 2011;118(17):4740-9.
Debbage et al., Intravital lectin perfusion analysis of vascular permeability in human micro- and macro-blood vessels. Histochem Cell Biol. Oct. 2001;116(4):349-59.
Debbage et al., Lectin intravital perfusion studies in tumor-bearing mice: micrometer-resolution, wide-area mapping of microvascular labeling, distinguishing efficiently and inefficiently perfused microregions in the tumor. J Histochem Cytochem. May 1998;46(5):627-39.
Folkman, Looking for a good endothelial address. Cancer Cell. Mar. 2002;1(2):113-5.
Gjorevski et al., Endogenous patterns of mechanical stress are required for branching morphogenesis. Integr Biol (Camb). Sep. 2010;2(9):424-34.
Harding et al., An implantable vascularized protein gel construct that supports human fetal hepatoblast survival and infection by hepatitis C virus in mice. PLoS One. Apr. 1, 2010;5(4):e9987.
Hristov et al., Endothelial progenitor cells: mobilization, differentiation, and homing. Arterioscler Thromb Vase Biol. Jul. 1, 2003;23(7):1185-9.

Intaglietta et al., Microvascular and tissue oxygen distribution. Cardiovasc Res. Oct. 1996;32(4):632-43.
Jain, Transport of molecules, particles, and cells in solid tumors. Annu Rev Biomed Eng. 1999;1:241-63.
Jeong et al., "Living" microvascular stamp for patterning of functional neovessels; orchestrated control of matrix property and geometry. Adv Mater. Jan. 3, 2012;24(1):58-63.
Kang et al., Bioengineered human vascular networks transplanted into secondary mice reconnect with the host vasculature and re-establish perfusion. Blood. Dec. 15, 2011;118(25):6718-21.
Kaufman-Francis et al., Engineered vascular beds provide key signals to pancreatic hormone-producing cells. PLoS One. 2012;7(7):e40741.
Kohfler et al., Improved vascular organization enhances functional integration of engineered skeletal muscle grafts. Proc Natl Acad Sci U S A Sep. 6, 2011;108(36):14789-94.
Koike et al., Tissue engineering: creation of long-lasting blood vessels. Nature. Mar. 11, 2004;428(6979):138-9.
Lee et al., Controlled growth factor release from synthetic extracellular matrices. Nature. Dec. 21-28, 2000;408 (6815):998-1000.
Leight et al., Manipulation of 3D Cluster Size and Geometry by Release from 2D Micropatterns. Cell Mol Bioeng. Sep. 1, 2012;5(3):299-306.
Liu et al., Hepatocyte cocultures with endothelial cells and fibroblasts on micropatterned fibrous mats to promote liver-specific functions and capillary formation capabilities. Biomacromolecules Mar. 10, 2014;15(3):1044-54.
Lovett et al., Vascularization strategies for tissue engineering. Tissue Eng Part B Rev. Sep. 2009;15(3):353-70.
Mcguigan et al., Vascularized organoid engineered by modular assembly enables blood perfusion. Proc Natl Acad Sci U S A. Aug. 1, 2006;103(31):11461-6.
Melero-Martin et al., Engineering robust and functional vascular networks in vivo with human adult and cord blood-derived progenitor cells. Circ Res. Jul. 18, 2008;103(2):194-202.
Mironov et al., Organ printing: tissue spheroids as building blocks. Biomaterials. Apr. 2009;30(12):2164-74.
Mooney et al., Growing new organs. Sci Am. Apr. 1999;280(4):60-5.
Nahmias et al., Laser-guided direct writing for three-dimensional tissue engineering. Biotechnol Bioeng. Oct. 20, 2005;92(2):129-36.
Nikolova et al., The vascular basement membrane: a niche for insulin gene expression and Beta cell proliferation. Dev Cell. Mar. 2006;10(3):397-405.
Phelps et al., Engineering more than a cell: vascularization strategies in tissue engineering. Curr Opin Biotechnol. Oct. 2010;21(5):704-9.
Pittman et al., Influence of microvascular architecture on oxygen exchange in skeletal muscle. Microcirculation. May 1995;2(1):1-18.
Radisic et al., High-density seeding of myocyte cells for cardiac tissue engineering. Biotechnol Bioeng. May 20, 2003;82(4):403-14.
Reid et al., Extracellular matrix gradients in the space of Disse: relevance to liver biology. Hepatology. Jun. 1992;15(6):1198-203.
Richardson et al., Polymeric system for dual growth factor delivery. Nat Biotechnol. Nov. 2001;19(11):1029-34.
Roh et al., Tissue-engineered vascular grafts transform into mature blood vessels via an inflammation-mediated process of vascular remodeling. Proc Natl Acad Sci U S A. Mar. 9, 2010;107(10):4669-74.
Rosmorduc et al., Hypoxia: a link between fibrogenesis, angiogenesis, and carcinogenesis in liver disease. Semin Liver Dis. Aug. 2010;30(3):258-70.
Smith et al., Locally enhanced angiogenesis promotes transplanted cell survival. Tissue Eng. Jan.-Feb. 2004;10 (1-2):63-71.
Traktuev et al., Robust functional vascular network formation in vivo by cooperation of adipose progenitor and endothelial cells. Circ Res. Jun. 19, 2009;104(12):1410-20.
US Department of Health and Human Services, National Organ Transplant Waiting List Report.
Vacanti et al.. Tissue engineering: the design and fabrication of living replacement devices for surgical reconstruction and transplantation. Lancet. Jul. 1999;354 Suppl 1:SI32-4.

(56) References Cited

OTHER PUBLICATIONS

Vacanti, Tissue engineering and the road to whole organs. Br J Surg. Apr. 2012;99(4):451-3.

Weber et al., Cell-matrix interactions improve beta-cell survival and insulin secretion in three-dimensional culture. Tissue Eng Part A. Dec. 2008;14(12):1959-68.

White et al., Longitudinal in vivo imaging to assess blood flow and oxygenation in implantable engineered tissues. Tissue Eng Part C Methods. Sep. 2012;18(9):697-709.

International Search Report and Written Opinion for Application No. PCT/US2013/049933, dated Dec. 17, 2013.

Partial Supplementary European Search Report for Applicatio No. 13817119.4, dated Feb. 24, 2016.

U.S. Appl. No. Oct. 1, 2019, filed Oct. 1, 2019, 2020-0101201, Published.

U.S. Appl. No. Mar. 26, 2021, filed Mar. 26, 2021, 2021-0213171, Published.

Omidan et al., Swelling and mechanical properties of modified hema-based superporous hydrogels. J Bioact Compat Polym. Sep. 2010;25:483-97.

\* cited by examiner

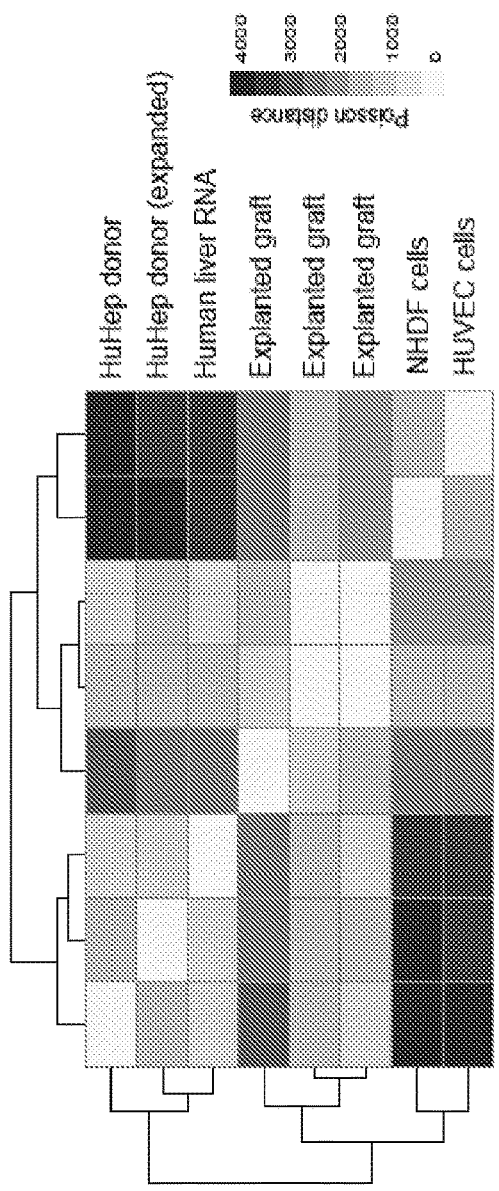
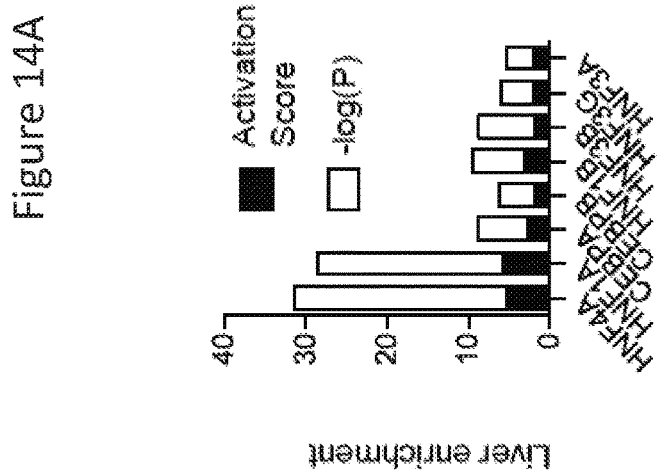
Figure 14B
Figure 14A

IN SITU EXPANSION OF ENGINEERED DEVICES FOR REGENERATION

RELATED APPLICATIONS

This application is a 35 U.S.C. 371 national stage filing of International Application No. PCT/US2016/055972, filed on Oct. 7, 2016, which claims priority to U.S. Provisional Patent Application Ser. No. 62/239,214 filed Oct. 8, 2015. The contents of the aforementioned applications are hereby incorporated by reference in their entireties.

GOVERNMENT FUNDING

This invention was made with government support under Grant Nos. R01EB008396 awarded by the National Institute of Health. The government has certain rights in the invention.

BACKGROUND

Advances in tissue engineering have enabled the generation of numerous tissue types that can recapitulate many aspects of native organs, bringing closer the promise that engineered tissues may ultimately replace whole organ transplantation (Atala, A., et al., *Science Translational Medicine* (2012), Vol. 4: 160rv112; Bianco, P. and Robey, P. G., *Nature* (2001), Vol. 414: 118-121). However, scaling up these tissues to physiologically-relevant sizes remains a major challenge. For engineered tissues that can be fed by diffusion of nutrients from the environment, the scaling problem has not been the limiting factor for clinical translation. These include thin tissues such as the cornea and skin, thick tissues with low metabolic requirements such as cartilage, or small-scale endocrine tissues such as beta-cells of the pancreas (Atala, A., et al., *Science Translational Medicine* (2012), Vol. 4: 160rv112; Bianco, P. and Robey, P. G., *Nature* (2001), Vol. 414: 118-121). However, the magnitude of the scale-up problem is enormous for large, solid organs such as the heart, kidney, and liver. For example, the liver contains over 100 billion hepatocytes, all positioned within 50 microns of the circulation (Li, A. P. *Chemico-Biological Interaction* (2007), Vol. 168: 16-29). Thus, robust vascularization is critical to the delivery of vital nutrients to the entire parenchyma of such solid organs. A need therefore exists for new approaches to engineer complex tissues for regenerative medicine.

SUMMARY

This disclosure is based, at least in part, on Applicants' discovery that an engineered human tissue seed can grow by in situ expansion of cellular components in response to systemic regenerative cues, following implantation in a host. In some aspects, an engineered human tissue seed of the disclosure includes human hepatocytes, endothelial cells, and fibroblasts in a degradable, biocompatible, hydrogel which is implanted ectopically to expand as much as 50-fold in situ in response to regenerative cues. The resultant engineered human liver tissue phenocopies several aspects of native liver structure and function including perfused vascular networks, self-assembled structures resembling bile ducts, and a repertoire of human hepatocyte blood products.

In some aspects, the disclosure relates to engineered tissue seeds suitable for implantation in a host, in which a first cell population of human parenchymal cells is co-cultured with a second cell population of human stromal cells, thereby forming a cell aggregate. The cell aggregate is combined with a third cell population of vascular cells micropatterned in a biocompatible hydrogel scaffold to form geometrically defined vascular cell cords, such that when the parenchymal and stromal cell aggregates are combined with the vascular cell cords, the aggregates are not in direct contact with the vascular cell cords. The parenchymal and stromal cell aggregates are encapsulated with the vascular cell cords in the biocompatible hydrogel scaffold, thereby forming an engineered tissue seed suitable for implantation in a host.

Applicants have discovered that the organization of the three cell populations in the engineered tissue seed (the cell architecture) programs the engineered tissue seed implant into a regenerative state, such that upon implantation in a host, factors are produced by the cells within the engineered tissue seed implant (paracrine signaling) and from the invading host. Such factors are regenerative cues that result in growth of the implant into an engineered tissue having normal architecture of a human tissue, such as a human liver, through cellular reorganization (lack of fibrosis) without rejection, inflammation, or scarring of the implant.

Accordingly, one aspect of the disclosure relates to an engineered tissue seed suitable for implantation in a host, comprising
  (a) a first cell population of primary human hepatocytes;
  (b) a second cell population of human fibroblasts;
  (c) a third cell population of primary human endothelial cells; and
  (d) a biocompatible hydrogel scaffold,
wherein the first and second cell populations are combined to form hepatocyte aggregates, wherein the third cell population is micropatterned in the biocompatible hydrogel scaffold to form geometrically defined endothelial cell cords, wherein the hepatocyte aggregates are combined with the endothelial cell cords in the biocompatible hydrogel scaffold, thereby forming an engineered tissue seed suitable for implantation in a host.

In some aspects, the engineered tissue seed of the disclosure expands in response to a regeneration cue, following implantation in a host. In some aspects, liver parenchyma in the engineered tissue seed expands in response to regeneration cues, following implantation in a host. In other aspects, vasculature in the engineered tissue seed expands in response to regeneration cues, following implantation in a host. In yet other aspects, the engineered tissue seed of the disclosure expands about 50-fold in situ, following implantation in a host.

In some aspects, the disclosure relates to an engineered tissue seed as described herein which secretes a hepatocyte blood factor selected from the group consisting of albumin, transferrin, alpha-1-antitrypsin, and fibronectin, or a combination thereof, following implantation in a host.

In some aspects, the engineered tissue seed as described herein expands to form densely packed hepatocytes, following implantation in a host. In some aspects, the engineered tissue seed of the disclosure expands to form duct-like structures resembling bile ducts, following implantation in a host. In some aspects, the engineered tissue seed of the disclosure expands to form biliary epithelial-like cells, following implantation in a host. In some aspects, the engineered tissue seed as described herein expands to form blood vessels, following implantation in a host. In some aspects, the engineered tissue seed as described herein expands to form blood vessels containing human endothelial cells, following implantation in a host.

In some aspects of the disclosure, the engineered tissue seed as described herein expands in response to paracrine signaling between cells in the engineered tissue seed, following implantation in a host. In some aspects the engineered tissue seed of the disclosure expands in response to a regeneration cue from the host, wherein the regeneration cue is due to an injury in the host. In some aspects, the engineered tissue seed of the disclosure expands in response to a regeneration cue from the host, wherein the regeneration cue is due to disease or infection in the host. In some aspects, the engineered tissue seed of the disclosure expands in response to a regeneration cue from the host, wherein the regeneration cue occurs during native development of the host. In some aspects, the engineered tissue seed as described herein expands in response to a regeneration cue which is a growth factor or cytokine.

In other aspects, the disclosure relates to an engineered tissue seed as described herein further comprising a small molecule or growth factor which stimulates or enhances expansion of the engineered tissue seed, following implantation in a host.

Other aspects of the disclosure relate to an engineered tissue seed suitable for implantation in a host, comprising
  (a) a first cell population of human parenchymal cells;
  (b) a second cell population of human stromal cells;
  (c) a third cell population of vascular cells; and
  (d) a biocompatible hydrogel scaffold,
wherein the first and second cell populations are co-cultured to form parenchymal and stromal cell aggregates, wherein the third cell population is micropatterned in the biocompatible hydrogel scaffold to form geometrically defined vascular cell cords, wherein the parenchymal and stromal cell aggregates are combined with the vascular cell cords, but not in direct contact with the vascular cell cords, and wherein the parenchymal and stromal cell aggregates are encapsulated with the vascular cell cords in the biocompatible hydrogel scaffold, thereby forming an engineered tissue seed suitable for implantation in a host.

In some aspects, the vascular cell cords of the engineered tissue seed as described herein are formed in channels in a polydimethylsiloxane (PDMS) substrate and encapsulated in a biocompatible hydrogel scaffold, thereby forming encapsulated vascular cell cords. In some aspects, the encapsulated vascular cell cords are removed from the PDMS substrate and parenchymal and stromal cell aggregates are added as a layer over the encapsulated vascular cell cords and encapsulated in the biocompatible hydrogel scaffold, thereby forming an engineered tissue seed suitable for implantation in a host.

Other aspects of the disclosure relate to methods of in situ expansion of an engineered tissue seed in a host, comprising implanting in the host an engineered tissue seed as described herein. In some aspects of the disclosure, regeneration and growth of the engineered tissue seed in situ is monitored in the host by detecting the presence of a regenerative factor (or biomarker), such as a growth factor (e.g., hepatocyte growth factor (HGF)), in a sample (such as a blood sample) from the host. Some aspects of the disclosure relate to detecting in a sample from the host the presence of one or more biomarkers that may indicate a compromised liver function in a human subject that would improve following regeneration of an engineered tissue seed. Such biomarkers include, for example, serum albumin, alpha-1 antitrypsin, transferrin, clotting factors, drug metabolism. In some aspects, the engineered tissue seed is implanted ectopically in the host. In some aspects, the host is a human subject in need thereof.

Other aspects of the disclosure relate to methods of in situ expansion of engineered human liver tissue in a host, comprising implanting in the host an engineered human liver tissue seed comprising
  (a) a first cell population of primary human hepatocytes;
  (b) a second cell population of human fibroblasts;
  (c) a third cell population of primary human endothelial cells; and
  (d) a biocompatible hydrogel scaffold,
wherein the first and second cell populations are combined to form hepatocyte aggregates, wherein the third cell population is micropatterned in the biocompatible hydrogel scaffold to form geometrically defined endothelial cell cords, wherein the hepatocyte aggregates are combined with the endothelial cell cords in the biocompatible hydrogel scaffold, thereby forming an engineered human liver tissue seed, and wherein the engineered human liver tissue seed expands in response to a regeneration cue following implantation in the host.

In some aspects, liver parenchyma in the engineered human liver tissue seed expands in response to regeneration cues. In some aspects, vasculature in the engineered human liver tissue seed expands in response to regeneration cues. In some aspects, the engineered human liver tissue seed expands about 50-fold in situ.

In some aspects, the engineered human liver tissue seed as described herein secretes a hepatocyte blood factor selected from the group consisting of albumin, transferrin, alpha-1-antitrypsin, and fibronectin, or a combination thereof. In some aspects, expansion of the engineered tissue seed in the host is monitored by detecting the presence of one or more hepatocyte blood factors.

In some aspects, the engineered human liver tissue seed expands to form densely packed hepatocytes. In some aspects, the engineered human liver tissue seed expands to form duct-like structures resembling bile ducts. In some aspects, the engineered human liver tissue seed expands to form biliary epithelial-like cells. In some aspects, the engineered human liver tissue seed expands to form blood vessels. In some aspects, the engineered human liver tissue seed expands to form blood vessels containing human endothelial cells.

In some aspects, the engineered human liver tissue seed expands in response to paracrine signaling between cells in the engineered tissue seed following implantation in a host. In some aspects, the engineered human liver tissue seed expands in response a regeneration cue due to an injury (e.g., surgical, chemical injury) in the host. In other aspects, the engineered human liver tissue seed expands in response to a regeneration cue due to disease (e.g., cancer, cirrhosis) or infection (e.g., viral (e.g., hepatitis) infection) in the host. In some aspects, the engineered human liver tissue seed expands in response to a regeneration cue which occurs during native development of the host. In some aspects the regeneration cue is a growth factor or cytokine.

Other aspects of the disclosure relate to methods of making an engineered tissue seed suitable for implantation in a host, comprising
  (a) providing a co-culture comprising a population of primary human hepatocytes and a population of human fibroblasts, thereby forming hepatocyte aggregates;
  (b) providing a population of primary human endothelial cells; and
  (c) providing a biocompatible hydrogel scaffold, wherein the population of primary human endothelial cells is micropatterned in the biocompatible hydrogel scaffold to form geometrically defined endothelial cell cords, and (d) combining the hepatocyte aggregates with the endothelial cell cords in the biocompatible hydrogel scaffold, wherein the hepatocyte aggregates are micropatterned between endothelial cell cords and not in direct contact with the endothelial cell cords, thereby forming an engineered tissue seed suitable for implantation in a host.

In some aspects, the engineered tissue seed as described herein proliferates to enlarge the graft in response to regeneration cues, following implantation in a host. In some aspects, the engineered tissue seed graft volume expands 11-fold in response to a regeneration cue, following implantation in a host.

In some aspects, the engineered tissue seed as described herein is functional and synthesizes more human proteins in response to a regeneration cue, following implantation in a host.

In some aspects, the engineered tissue seed as described herein expresses genes of major hepatic drug metabolism pathways, similar to levels in the human liver, in response to a regeneration cue following implantation in a host. In some aspects, the engineered tissue seed as described herein expresses Phase I cytochrome P450 enzymes, Phase II enzymes, Phase III anion and ATP-binding transporters in response to a regeneration cue, following implantation in a host. In some aspects, the engineered tissue seed as described herein expresses drug-metabolizing enzymes in response to a regeneration cue, following implantation in a host. In some aspects, the drug-metabolizing enzymes are enhanced after administration of Rifampin. In some aspects, the engineered tissue seed as described herein retains a hepatic phenotype and is functional, as characterized by synthesis and drug metabolism.

In some aspects, the engineered tissue seed as described herein expands in response to a regeneration cue, following implantation in a host, and comprises dense aggregate-like units that exhibit structure reminiscent of hepatic cords in the normal liver. In some aspects, the engineered tissue seed as described herein expands in response to a regeneration cue, following implantation in a host, and comprises hepatic units arranged within a syncytium of interconnected lacunae containing endovascular stroma and lined with collagen III. In some aspects, the engineered tissue seed as described herein expands in response to a regeneration cue, following implantation in a host, and comprises bile canalicular-like structures between adjacent hepatocytes. In some aspects, the engineered tissue seed as described herein expands in response to a regeneration cue, following implantation in a host, and comprises larger vacuolar structures lined with multidrug resistance-associated protein 2 (MRP2). In some aspects, the engineered tissue seed as described herein expands in response to a regeneration cue, following implantation in a host, and comprises human biliary epithelial-like cells that have self-assembled to form ductal-like structures at an ectopic location with the seed. In some aspects, the ductal structures are associated with features of portal triads, such as vasculature and connective tissue. In some aspects, the engineered tissue seed as described herein self assembles upon expansion to create densely packed ectopic hepatic tissue with several microstructural hallmarks typically associated with human liver, in response to a regeneration cue, following implantation in a host.

In some aspects, the engineered tissue seed as described herein comprises red blood cells. In some aspects, the engineered tissue seed as described herein comprises red blood cells identified by erythrocyte markers. In some aspects, the erythrocyte marker is Ter-119. In some aspects, a blood pool within the engineered tissue seed as described herein expands in response to a regeneration cue, following implantation in a host. In some aspects, the engineered tissue seed as described herein comprises significantly more blood in response to a regeneration cue, following implantation in a host, compared to a suitable control. In some aspects, the engineered tissue seed as described herein comprises human vascular networks carrying blood in response to a regeneration cue, following implantation in a host.

In some aspects, the engineered tissue seed as described herein comprises angiocrine factors. In some aspects, expansion of the engineered tissue seed in response to a regeneration cue, following implantation in a host, is enhanced by expression of angiocrine signals. In some aspects, the endothelial cords within the engineered tissue seed release angiocrine signals in response to a regeneration cue, following implantation in a host.

In some aspects, the engineered tissue seed as described herein comprises hepatocyte cellular aggregates and endothelial cords, wherein the endothelial cords are near but not in contact with the hepatocytes aggregates.

Other aspects of the disclosure relate to an engineered tissue seed suitable for implantation in a host, comprising
(a) a first cell population of human cardiomyocyte cells;
(b) a second cell population of human stromal cells;
(c) a third cell population of vascular cells; and
(d) a biocompatible hydrogel scaffold,
wherein the first and second cell populations are co-cultured to form cardiomyocyte and stromal cell aggregates, wherein the third cell population is micropatterned in the biocompatible hydrogel scaffold to form geometrically defined vascular cell cords, wherein the cardiomyocyte and stromal cell aggregates are combined with the vascular cell cords, but not in direct contact with the vascular cell cords, and wherein the cardiomyocyte and stromal cell aggregates are encapsulated with the vascular cell cords in the biocompatible hydrogel scaffold, thereby forming an engineered tissue seed suitable for implantation in a host.

Other aspects of the disclosure relate to an engineered tissue seed suitable for implantation in a host, comprising
(a) a first cell population of human myocyte cells;
(b) a second cell population of human stromal cells;
(c) a third cell population of vascular cells; and
(d) a biocompatible hydrogel scaffold,
wherein the first and second cell populations are co-cultured to form myocyte and stromal cell aggregates, wherein the third cell population is micropatterned in the biocompatible hydrogel scaffold to form geometrically defined vascular cell cords, wherein the myocyte and stromal cell aggregates are combined with the vascular cell cords, but not in direct contact with the vascular cell cords, and wherein the myocyte and stromal cell aggregates are encapsulated with the vascular cell cords in the biocompatible hydrogel scaffold, thereby forming an engineered tissue seed suitable for implantation in a host.

In some aspects, the engineered tissue seed as described herein comprises mitogens to promote expansion in a host. In some aspects, the mitogen is IGF-1 or bFGF.

BRIEF DESCRIPTION OF THE FIGURES

FIG. 8A shows hepatocytes and NHDFs in aggregates self-organized over 20 days in vitro. Scale bars are 100 µm. FIG. 8B is a bar graph depicting the addition of NHDFs resulted in a dose-dependent increase in albumin production at day 20.

FIG. 11A is a bar graph depicting the percentage of EdU+Ck-18+ cells. *=p<0.05. FIG. 11B provides representative images of tissue seeds. Scale bars are 25 µm.

FIG. 13B shows Phase I enzymes CYP3A4 (left) and CYP2B6 (right) gene expression. FIG. 13C shows Phase II enzyme SULT1A1 gene expression. FIG. 13D shows Phase III anion SLCO1B1 gene expression. FIG. 13E shows ATP-binding transporter ABCG5 gene expression. FIG. 13F shows rifampin induced CYP3A4 expression. *=p<0.05

FIGS. 14A and 14B show the assessment of the fraction of genes known to be downstream of given transcription factors that were differentially regulated between seeds and HUVEC/NHDF controls using Ingenuity Pathway Analysis. FIG. 14A shows the transcription factors identified. FIG. 14B shows hierarchical clustering of transcriptomes identified by RNA-seq of expanded seeds, pure human primary hepatocytes, human liver, and pure populations of NHDFs and HUVECs. Seeds cluster between the primary hepatocyte/human liver samples and non-parenchymal HUVEC/NHDF cell lines.

FIG. 15A shows hematoxylin and eosin (H&E) staining. FIG. 15B shows Arg-1 staining. FIG. 15C shows Ck-18 and multidrug resistance-associated protein 2 (MRP2) staining. FIG. 15D shows reticulin staining.

FIG. 20A is a schematic showing human liver tissues created in which hepatocytes, HUVECs and NHDFs were randomly organized as single cells within fibrin hydrogels (left), hepatocytes, HUVECs and NHDFs were aggregated to create tri-cell aggregates, which were then randomly seeded within fibrin hydrogels (middle), or hepatocytes and NHDFs were patterned together in aggregates and HUVECs in endothelial cords followed by molding together to form seeds (right). FIG. 20B provides representative images wherein all three architectural conformations produced Ck-18+ hepatic grafts after 80 days. Scale bars 100 µm. FIG. 20C shows bar graphs depicting graft size (pixels; left), albumin production (ng/ml; middle) and transferrin production (ng/ml; right). FIG. 20D is a bar graph showing inclusion of both NHDFs and HUVECs in seeds was necessary for maximal hepatic function after expansion, as measured by human albumin production (ng/ml). FIG. 20E shows a comparison of the mRNA expression patterns present in engineered constructs with either random HUVECs or endothelial cords, one day after formation of the tissues in vitro. Pre-organization of HUVECs into endothelial cords resulted in increased expression of several key angiocrine genes. *p<0.05

DETAILED DESCRIPTION

The present disclosure relates to methods and constructs for tissue engineering in situ to regenerate an organ from an engineered tissue seed comprised of mature cell populations that coordinately grow following implantation. In some aspects, the engineered tissues seeds are composed of human parenchymal cells, vascular cells and stromal cells in a specified architecture in a degradable biomaterial that collectively supports expansion in response to regenerative stimuli following implantation in a host. Engineered tissue seeds of the disclosure engraft and expand ectopically by 50-fold and demonstrate emergence of self-organized biliary networks within the newly-formed, vascularized hepatic parenchyma. Notably, engineered tissue seeds of the disclosure expand in response to regenerative cues to contain biliary epithelial-like cells that self-organized into structures resembling bile ducts, thus resembling a human liver with anatomic features that recapitulate the native liver.

Engineered tissue seeds of the disclosure engraft and likely respond to multicellular paracrine signaling loops existing between hepatocytes, endothelial cells, and stromal cells, including, for example, signals such as hepatocyte growth factor (HGF), transforming growth factor α (TGFα), wingless-related integration site 2 (Wnt2), and angiopoietin-2 from stellate cells or endothelial cells to neighboring hepatocytes which are known to be critical for normal organogenesis and regeneration.

Figure 1A:
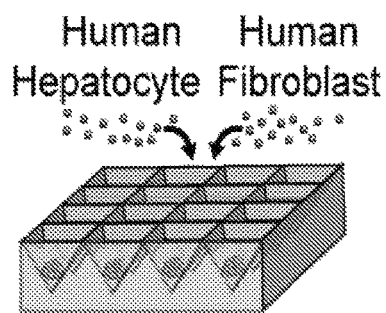
FIG. 1A is a schematic showing hepatocyte aggregates containing human hepatocytes and human fibroblasts created using pyramidal microwells.
Figure 1A:
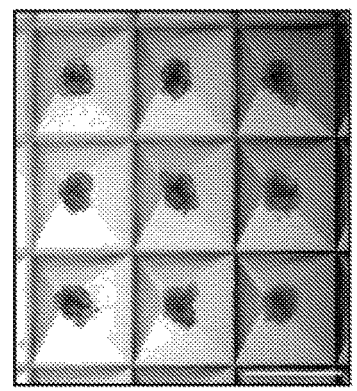
Figure 1B:
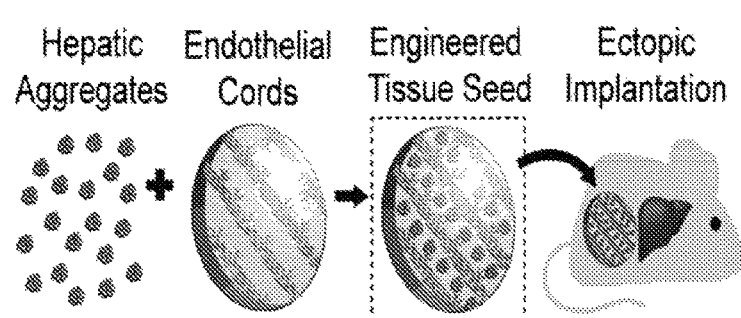
FIG. 1B is a schematic showing hepatocyte aggregates combined with endothelial cords to generate an engineered tissue seed of the disclosure that is implanted ectopically into a mouse. All scale bars are 400 µm.
Figure 1B:
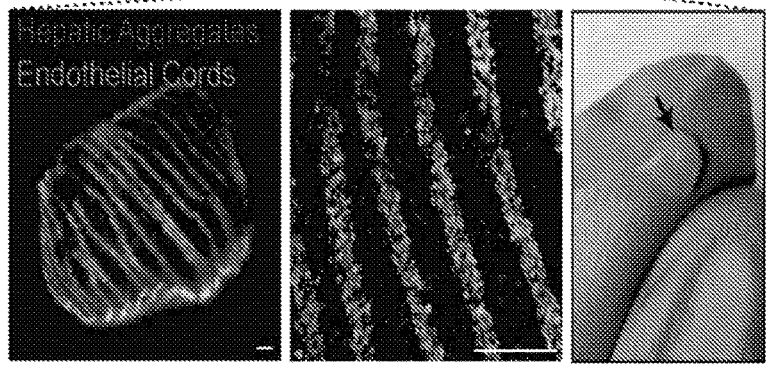

As described herein, the architecture of the engineered tissue constructs of the disclosure is important for proper expansion as paracrine signals are often influenced by the spatial proximity between different cell types (see FIG. 1B). Engineered tissue constructs with hepatocytes in direct contact with stromal cells (e.g., as aggregates) and endothelial cells micropatterned in cords such that the endothelial cells are near, but not in contact with hepatocytes leads to optimal hepatic function (see FIG. 9). Thus, some embodiments of the disclosure features engineered tissue seeds with patterned stromal cells in immediate proximity to hepatocytes within cellular aggregates and distinct endothelial cords near to but not touching hepatic aggregates in biocompatible hydrogels.

In addition to local signals from neighboring cell types, engineered tissue seeds of the disclosure respond to systemic regenerative signals (e.g., growth factors) following implantation in a host, such as regenerative signals due to injury, disease or infection. Signals mediating this interaction include growth factors which control hepatocyte proliferation in regeneration and development, such as hepatocyte growth factor (HGF) or biomarkers of human disease, such as liver cirrhosis.

Other aspects of the disclosure feature an engineered tissue seed which provides additional microenvironmental cues such as microbeads releasing small molecules or growth factors incorporated into the engineered tissue seed to stimulate or enhance hepatocyte proliferation and expansion.

Some aspects of the disclosure feature a human engineered tissue seed made of a biocompatible hydrogel scaffold comprising a first population of cells having a specific morphology, phenotype and/or highly differentiated function. In certain embodiments, the human tissue construct comprises at least one population of parenchymal cells having a specific morphology, phenotype and/or highly differentiated function. Exemplary cells include, but are not limited to hepatocytes, chondrocytes, adipocytes, myocytes, pancreatic cells, splenocytes, pancreatic islet cells, enterocytes, neurons, and other parenchymal cells described herein.

In certain embodiments, the human engineered tissue seed comprises at least one population of non-parenchymal cells, co-cultured in heterotypic contact with the parenchymal cells so as to support the specific morphology, phenotype and/or highly differentiated function and/or viability of the parenchymal cells. In other embodiments, the human engineered tissue seed comprises at least one population of cells, optionally not in contact with the parenchymal cells (or parenchymal cell:non-parenchymal cell co-cultures), wherein the population further supports the morphology, phenotype, function and/or viability of the parenchymal cells (or co-cultures comprising same), for example, by secreting or producing factors, e.g., soluble factors, or biochemical cues that support said morphology, phenotype, function or viability. Co-encapsulated non-parenchymal cells can also have the dual function of supporting the differentiated morphology, phenotype and/or function of the parenchymal cells and effecting the host environment or microenvironment surrounding the implanted constructs. For example, non-parenchymal cells encapsulated in the constructs described herein can secrete, e.g., growth factors and/or cytokines that promote vascularization of the constructs in vivo. Without being bound in theory, it is also contemplated that the non-parenchymal cells encapsulated in the constructs described herein may play a role in recruiting, for example, inflammatory cells, thus mediating (e.g., promoting or deterring) interaction with the immune system of the host animal (e.g., a bidirectional interaction between the implanted construct and the surrounding environment).

In certain embodiments, the engineered tissue seed of the disclosure comprises a first population of parenchymal cells, a second population of non-parenchymal cells, and a third population of vascular cells. The vascular cells are micropatterned in a biocompatible hydrogel scaffold to form geometrically defined vascular cell cords, allowing for vascularization of the engineered tissue seed upon engraftment. In certain embodiments, the vascular cells are endothelial cells.

The skilled artisan will appreciate that various encapsulation formats are useful and that variation of the encapsulation format can be made to optimize the desired function of the engineered tissue seed. For example, in some embodiments, the parenchymal cells and one or more populations of non-parenchymal cells can be in contact, e.g., heterotypic contact between parenchymal cells and one or more populations of non-parenchymal cells, optionally with heterotypic contact between various populations of non-parenchymal cells. However, due the soluble nature of certain biochemical cues secreted by the non-parenchymal cells, cell-cell contact is not necessarily required in the constructs described herein.

Such engineered tissue seeds are particularly suited for implantation in a host, for example a human or non-human, animal host. In some embodiments, engineered tissue seeds as described herein are useful to produce an animal (e.g., a mouse) having an engineered human tissue. In such fashion, these animals are made having a host of uses, in particular, in pharmaceutical development and as animal models of disease.

Definitions

So that the disclosure may be more readily understood, certain terms are first defined.

As used herein, the term "co-culture" refers to a collection of cells cultured in a manner such that more than one population of cells are in association with each other. Co-cultures can be made such that cells exhibit heterotypic interactions (i.e., interaction between cells of populations of different cell types), homotypic interactions (i.e., interaction between cells of the same cell types) or co-cultured to exhibit a specific and/or controlled combination of heterotypic and homotypic interactions between cells.

As used herein, the term "encapsulation" refers to the confinement of a cell or population of cells within a material, in particular, within a biocompatible hydrogel. The term "co-encapsulation" refers to encapsulation of more than one cell or cell type or population or populations of cells within the material, e.g., the hydrogel.

As used herein, the term "biochemical factor" or "biochemical cue" refers to an agent of a chemical nature having a biological activity, for example, on a cell or in a tissue. Exemplary biochemical factors or cues include, but are not limited to growth factors, cytokines, nutrients, oxygen, proteins, polypeptides and peptides, for example, adhesion-promoting proteins, polypeptides and peptides, and the like. Exemplary adhesion-promoting peptides include those derived from the extracellular matrix (ECM) of a cell or tissue, including, but not limited to collagen-derived peptides, laminin-derived peptides, fibronectin-derived peptides (e.g., the RGD-peptides), and the like.

The term "regeneration cue" as used herein, refers to a biochemical factor involved in the recruitment, proliferation, and differentiation of cells, for example, a factor produced by one or more cell populations within the engineered tissue seed or by cells of the host following implantation due to injury, disease, infection or native development of the host. In certain embodiments, the engineered tissue seed expands in situ in response to a regeneration cue. In certain embodiments, the regenerative cue is endogenous. In certain embodiments, the regenerative cue is exogenous, such as provided by a small molecule or growth factor, incorporated, for example, into the engineered tissue seed to stimulate or enhance cell proliferation and expansion.

The term "paracrine signal" as used herein, refers to a biochemical factor or cue involved in recruitment, proliferation, and differentiation of cells that originates from one or more cell populations within the engineered tissue seed.

Co-cultures can be included in engineered tissue seeds as described herein, and implanted in vivo. Co-cultivation of hepatocytes with non-parenchymal fibroblast cells prior to encapsulation improves hepatocyte survival compared to hepatocytes alone. In some embodiments, the microenvironment within the hydrogels is further tuned to exploit the importance of facilitating cell:matrix interactions within implantable engineered tissue seeds by conjugating to the polymer backbone peptides derived from extracellular-matrix molecules. In particular, tethered RGDS from fibronectin improves encapsulated hepatocellular functions (e.g., albumin secretion, urea synthesis).

As used herein, the term "hydrogel" refers to a network of polymer chains that are hydrophilic in nature, such that the material absorbs a high volume of water or other aqueous solution. Hydrogels can include, for example, at least 70% v/v water, at least 80% v/v water, at least 90% v/v water, at least 95%, 96%, 97%, 98% and even 99% or greater v/v water (or other aqueous solution). Hydrogels can comprise natural or synthetic polymers, the polymeric network often featuring a high degree of crosslinking. Hydrogels also possess a degree of flexibility very similar to natural tissue, due to their significant water content. Hydrogels are particularly useful in tissue engineering applications as scaffolds for culturing cells. In certain embodiments, the hydrogels are made of biocompatible polymers.

As used herein, the term "parenchymal cells" refers to cells of, or derived from, the parenchyma of an organ or gland, e.g., a mammalian organ or gland. The parenchyma of an organ or gland is the functional tissue of the organ or gland, as distinguished from surrounding or supporting or connective tissue. As such, parenchymal cells are attributed with carrying out the particular function, or functions, of the organ or gland, often referred to in the art as "tissue-specific" function. Parenchymal cells include, but are not limited to, hepatocytes, pancreatic cells (alpha, beta, gamma, delta), myocytes, e.g., smooth muscle cells, cardiac myocytes, and the like, enterocytes, renal epithelial cells and other kidney cells, brain cell (neurons, astrocytes, glia cells), respiratory epithelial cells, stem cells, and blood cells (e.g., erythrocytes and lymphocytes), adult and embryonic stem cells, blood-brain barrier cells, adipocytes, splenocytes, osteoblasts, osteoclasts, and other parenchymal cell types known in the art.

Because parenchymal cells are responsible for tissue-specific function, parenchymal cells express or secrete certain tissue specific markers. In the liver, for example, liver tissue specific proteins include, but are not limited to, albumin, fibrinogen, transferrin, and cytokeratin 18 and cytokeratin 19. The functional activity of a particular parenchymal cell can vary with the type of non-parenchymal cell included within constructs described herein. For example, the quantity and rate of expression of albumin by hepatocytes in co-culture can vary between the type of fibroblast cell line used in a construct described herein.

Certain precursor cells can also be included as "parenchymal cells", in particular, if they are committed to becoming the more differentiated cells described above, for example, liver progenitor cells, oval cells, adipocytes, osteoblasts, osteoclasts, myoblasts, stem cells (e.g., embryonic stem cells, hematopoietic stem cells, mesenchymal stem cells, endothelial stem cells, and the like). In some embodiments stem cells can be encapsulated and/or implanted under specified conditions such that they are induced to differentiate into a desired parenchymal cell type, for example, in the engineered tissue seed. It is also contemplated that parenchymal cells derived from cell lines can be used in the methodologies of the disclosure.

The term "non-parenchymal cells" as used herein, refers to the cells of or derived from the tissue surrounding or supporting parenchymal tissue in an organ or gland, for example, in a mammalian (e.g., human) organ or gland, or the connective tissue of such an organ or gland. Exemplary non-parenchymal cells include, but are not limited to, stromal cells (e.g., fibroblasts), endothelial cells, stellate cells, cholangiocytes (bile duct cells), Kupffer cells, pit cells, and the like. The choice of non-parenchymal cells used in the constructs described herein will depend upon the parenchymal cell types used. For example, a variety of both liver and non-liver derived non-parenchymal cells have been reported to induce hepatic function in co-culture.

The term "engineered tissue seed" as used herein, refers to a construct that expands in size, volume, and cell number following implantation in a host. In some embodiments, the engineered tissue seed develops parenchyma and develops vasculature. In some embodiments, the engineered tissue seed includes a population of parenchymal cells, a population of non-parenchymal cells, and a population of vascular cells (e.g., endothelial cells). In some embodiments, the parenchymal and non-parenchymal cells are co-cultured together to form aggregates. In certain embodiments, the vascular cells (e.g., endothelial cells) are micropatterned into vascular cell cords. In some embodiments, the engineered tissue seed contains parenchymal and non-parenchymal cell aggregates and endothelial cords.

As used herein, the term "vascular cell cord" or "endothelial cell cord" refers to micropatterning of vascular cells into structures that resemble cylinders, rods, strings, or filaments and networks of such structures. In certain aspects, vascular cell cords when incorporated into an engineered tissue seed described herein provide an architecture for vascular expansion and development in the graft by providing a template for capillary formation. In some embodiments, vascular cells are used to form cords. In some embodiments, endothelial cells are used to form cords. In some embodiments, cords are generated by using pre-patterned biomaterials such as channels in a polydimethylsiloxane (PDMS) substrate and encapsulated in a biocompatible hydrogel scaffold.

As used herein, the term "hepatocellular function" refers to a function or activity of a hepatic cell (e.g., a hepatocyte) characteristic of, or specific to, the function of liver parenchymal cells, e.g., liver-specific function. Hepatocellular functions include, but are not limited to albumin secretion, urea production, liver-specific transcription factor activity, metabolism, e.g., drug metabolism. In certain embodiments, the hepatocellular function is drug metabolism, for example, the enzymatic activity of human Phase I detoxification enzymes (e.g., cytochrome P450 activity), human Phase II conjugating enzymes, human Phase III transporters, and the like. For example coumarin 7-hydroxylation is a human-specific process mediated by human Phase I metabolic enzymes, e.g., CYP2A6 or CYP2A2, in response to known substrates and/or inducers. Hepatocellular function is also determined by measuring a "hepatocyte blood factor." In certain embodiments, the hepatocyte blood factor is albumin, transferrin, alpha-1-antitrypsin, or fibronectin.

Maintenance of hepatocellular function can result from maintaining the desired morphology, cell-cell contact, environmental biochemical cues, adhesion, and the like, and within engineered tissue seeds described herein, can further result from promoting sufficient vascularization and oxygen and nutrient transport to the implanted construct.

As used herein, the term "liver regeneration" refers to the expansion, growth, and increase in volume of the liver. Liver regeneration can occur with replacement of tissue loss with phenotypic fidelity of cell types (i.e., each cell type of the liver enters into proliferation to replace its own cellular compartment). Liver regeneration can also occur by replacement of tissue by activation of transdifferentiation pathways originating from stem cells. In certain embodiments, liver regeneration is deemed to have occurred by an increase in hepatocyte cell number, an increase in cell size, an increase in volume of the liver, and/or an increase in size of the liver and/or by an increase in production of a liver derived factor (e.g., HGF). See e.g., Michalopoulos (*Comprehensive Physiology* (2013), Vol. 3: 485-513), herein incorporated by reference.

The term "expand" as used herein, refers to an increase in size, volume or area of a tissue graft. In certain embodiments, an engineered tissue seed expands, as determined by volume, weight, and area. In some embodiments, the engineered tissue seed expands in volume 11-fold. In some embodiments, the engineered tissue expands in volume 50-fold.

As used herein, the term "ectopic" means occurring in an abnormal position or place. Accordingly, "implantation at an ectopic site" means implantation at an abnormal site or at a site displaced from the normal site. Exemplary ectopic sites of implantation include, but are not limited to the intraperitoneal space and ventral subcutaneous space. Ectopic sites of implantation can also be within an organ, i.e., an organ different than that of the source cells of the construct being implanted (e.g., implanting a human liver construct into the spleen of an animal). Ectopic sites of implantation can also include other body cavities capable of housing a construct described herein. In some embodiments, ectopic sites include, for example, lymph nodes. At least one unexpected feature of the constructs described herein is that constructs implanted at ectopic sites in animals survive, expand, and maintain differentiated function for significant periods of time. This is in contrast to the art-recognized belief that implantation at an orthotopic site (i.e., occurring in a normal position or place) is required to provide trophic factors necessary to support viability (e.g., trophic factors from the gut necessary to support viability in transplanted hepatocyte systems). The term "ectopic" and "heterotropic" can be used interchangeably herein.

As used herein and in the appended claims, the singular forms "a," "and," and "the" include plural referents unless the context clearly dictates otherwise. Thus, for example, reference to "a cellular aggregate" includes a plurality of such cellular aggregates and reference to "the cell" includes reference to one or more cells known to those skilled in the art, and so forth.

Cell Aggregates

Parenchymal cells can be obtained from a variety of sources including, but not limited to, liver, skin, pancreas, neuronal tissue, muscle (e.g., heart and skeletal), and the like. Parenchymal cells can be obtained from parenchymal tissue using any one of a host of art-described methods for isolating cells from a biological sample, e.g., a human biological sample. Parenchymal cells. e.g., human parenchymal cells, can be obtained by biopsy or from cadaver tissue. In certain embodiments, parenchymal cells are derived from lung, kidney, nerve, heart, fat, bone, muscle, thymus, salivary gland, pancreas, adrenal, spleen, gall bladder, liver, thyroid, paraythyroid, small intestine, uterus, ovary, bladder, skin, testes, prostate, or mammary gland.

In certain embodiments, constructs contain human parenchymal cells optimized to maintain the appropriate morphology, phenotype and cellular function conducive to use in the methods of the disclosure. Primary human parenchymal cells can be isolated and/or pre-cultured under conditions optimized to ensure that the parenchymal cells of choice (e.g., hepatocytes) initially have the desired morphology, phenotype and cellular function and, thus, are poised to maintain said morphology, phenotype and/or function in the constructs, and in vivo upon implantation to create the engineered tissue seeds described herein.

Cells useful in the constructs and methods of the disclosure are available from a number of sources including commercial sources. For example, hepatocytes may be isolated by conventional methods (Berry and Friend, 1969, J. Cell Biol. 43:506-520) which can be adapted for human liver biopsy or autopsy material. In general, cells may be obtained by perfusion methods or other methods known in the art, such as those described in U.S. Pat. Pub. No. 20060270032.

Parenchymal and non-parenchymal cell types that can be used in the above-described constructs include, but are not limited to, hepatocytes, pancreatic cells (alpha, beta, gamma, delta), myocytes, enterocytes, renal epithelial cells and other kidney cells, brain cell (neurons, astrocytes, glia), respiratory epithelium, stem cells, and blood cells (e.g., erythrocytes and lymphocytes), adult and embryonic stem cells, blood-brain barrier cells, and other parenchymal cell types known in the art, fibroblasts, endothelial cells, and other non-parenchymal cell types known in the art.

In some embodiments, the cells used in the engineered tissue seeds described herein are mammalian cells, although the cells may be from two different species (e.g., humans, mice, rats, primates, pigs, and the like). The cells can be primary cells, or they may be derived from an established cell-line. Cells can be from multiple donor types, can be progenitor cells (e.g., liver progenitor cells), tumor cells, and the like. In certain embodiments, the cells are freshly isolated cells (for example, encapsulated within 24 hours of isolation), e.g., freshly isolated hepatocytes from cadaveric donor livers. Although any combination of cell types that promotes maintenance of differentiated function of the parenchymal cells can be used in the methods and constructs described herein (e.g., parenchymal and one or more populations of non-parenchymal cells, e.g., stromal cells), exemplary combinations of cells for producing the constructs include, without limitation: (a) human hepatocytes (e.g., primary hepatocytes) and fibroblasts; (b) hepatocytes and fibroblasts and endothelial cells; and (c) human hepatocytes and more than one population of fibroblasts. Other exemplary combinations include, without limitation, (a) human hepatocytes (e.g., primary hepatocytes) and fibroblasts (e.g., normal or transformed fibroblasts, including, for example, non-human transformed fibroblasts); (b) hepatocytes and at least one other cell type, particularly liver cells, such as Kupffer cells, Ito cells, endothelial cells, and biliary ductal cells; and (c) stem cells (e.g., liver progenitor cells, oval cells, hematopoietic stem cells, embryonic stem cells, and the like) and a non-parenchymal cell population, for example, stromal cells (e.g., fibroblasts). In some embodiments, combinations of hepatocytes, liver cells, and liver precursor cells may be used. In some embodiments it may be desirable to include immune cells in the constructs, e.g., Kupffer cells, macrophages, B-cells, dendritic cells, etc.

Hepatocytes which may be cultured in the co-culture system as described herein may be from any source known in the art, e.g., primary hepatocytes, progenitor-derived, ES-derived, induced pluripotent stem cells (iPS-derived), etc. Hepatocytes useful in the constructs and methods described herein may be produced by the methods described in Takashi Aoi et al., Science 321 (5889): 699-702; U.S. Pat. Nos. 5,030,105; 4,914,032; 6,017,760; 5,112,757; 6,506, 574; 7,186,553; 5,521,076; 5,942,436; 5,580,776; 6,458, 589; 5,532,156; 5,869,243; 5,529,920; 6,136,600; 5,665, 589; 5,759,765; 6,004,810; U.S. patent application Ser. Nos.

11/663,091; 11/334,392; 11/732,797; 10/810,311; and PCT application PCT/JP2006/306783, all of which are incorporated herein by reference in their entirety.

Further cell types which may be cultured in the engineered tissue seeds disclosed herein include pancreatic cells (alpha, beta, gamma, delta), enterocytes, renal epithelial cells, astrocytes, muscle cells, brain cells, neurons, glia cells, respiratory epithelial cells, lymphocytes, erythrocytes, blood-brain barrier cells, kidney cells, cancer cells, normal or transformed fibroblasts, liver progenitor cells, oval cells, adipocytes, osteoblasts, osteoclasts, myoblasts, beta-pancreatic islets cells, stem cells (e.g., embryonic stem cells, hematopoietic stem cells, mesenchymal stem cells, endothelial stem cells, etc.), cells described in U.S. patent application Ser. No. 10/547,057 paragraphs 0066-0075 which is incorporated herein by reference, myocytes, keratinocytes, and indeed any cell type that adheres to a substrate.

It is understood that the engineered tissue seeds disclosed herein may contain parenchymal cells with one, or two or more types of non-parenchymal cells such as, for example, stromal cells, endothelial cells, stellate cells, cholangiocytes (bile duct cells), Kupffer cells, pit cells, etc. In some embodiments, the parenchymal cells (e.g., hepatocytes) cultured in heterotypic contact with a first population of non-parenchymal cells and a second population of non-parenchymal cells are mixed and distributed around the co-cultured parenchymal cells. In some embodiments, the cell culture may contain at least one non-parenchymal cell population. In certain embodiments, the cell culture may contain more than one non-parenchymal cell population. One of skill in the art will appreciate that particular patterns of non-parenchymal cells surrounding the parenchymal cells may be desired in some cases, e.g., when it is desired to mimic certain in vivo environments. It is understood that any support or accessory cells may be included in the engineered tissue seeds disclosed herein.

In some embodiments, the parenchymal cell:non-parenchymal cell ratio within the aggregate is 1:2. In some embodiments, the hepatocytes:fibroblast cell ratio within the aggregate is 1:2.

In certain embodiments, supporting or accessory non-parenchymal cells can serve to enhance vascular recruitment to the constructs described herein. For example, non-parenchymal cells can be selected for encapsulation in the engineered tissue seeds disclosed herein based on their ability to secrete one or more pro-angiogenic factors. Exemplary pro-angiogenic factors include, but are not limited to vascular endothelial growth factor (VEGF), including isoforms A, B, C, and D, basic fibroblast growth factor (bFGF), interleukin-6 (IL-6), and other inflammatory cytokines, tumor necrosis factor alpha (TNFα), hepatocyte growth factor (HGF) and the like. Non-parenchymal cells can be selected that secret such factors, or can be engineered (e.g., recombinantly engineered) to secrete such factors.

Without being bound in theory, it is also contemplated that one or more soluble factors is included in an engineered tissue seed disclosed herein, for example, in drug delivery vehicle (e.g., encapsulated in a drug delivery particle, for example, a time-released delivery particle).

In certain embodiments, the engineered tissue seeds disclosed herein are engineered to include one or more adherence materials to facilitate maintenance of the desired phenotype of the encapsulated cells. The term "adherence material" is a material incorporated into an engineered tissue seed disclosed herein to which a cell or microorganism has some affinity, such as a binding agent. The material can be incorporated, for example, into a hydrogel prior to seeding with parenchymal and/or non-parenchymal cells. The material and a cell or microorganism interact through any means including, for example, electrostatic or hydrophobic interactions, covalent binding or ionic attachment. The material may include, but is not limited to, antibodies, proteins, peptides, nucleic acids, peptide aptamers, nucleic acid aptamers, sugars, proteoglycans, or cellular receptors.

The type of adherence material(s) (e.g., ECM materials, sugars, proteoglycans etc.) will be determined, in part, by the cell type or types to be cultured. ECM molecules found in the parenchymal cell's native microenvironment are useful in maintaining the function of both primary cells, and precursor cells and/or cell lines. For example, hepatocytes are known to bind to collagen. Therefore, collagen is well suited to facilitate binding of hepatocytes. The liver has heterogeneous staining for collagen I, collagen III, collagen IV, laminin, and fibronectin. Hepatocytes also display integrins $\beta$, $\beta 2$, $\alpha 1$, $\alpha 2$, $\alpha 5$, and the nonintegrin fibronectin receptor Agp110 in vivo. Cultured rat hepatocytes display integrins $\alpha 1$, $\alpha 3$, $\alpha 5$, $\beta 1$, and $\alpha 6\mu 1$, and their expression is modulated by the culture conditions.

Without being bound in theory, it is believed that optimal engineered tissue seed performance results from a combination of appropriate heterotypic contacts, for example, between parenchymal cells and at least one population of non-parenchymal cells and soluble biochemical cues (e.g., supporting parenchymal cell phenotype and function and, optionally, additionally promoting vascularization.) Parenchymal cell stabilizing cues and proangiogenic cues can come from the same, or from different populations of non-parenchymal cells. Additional stabilizing cues can include, for example, certain cell-surface molecules, cadherins, receptor ligands, and the like (see, in particular, Khetani et al. 2004, Hepatology 40(3): 545-554, the content of which is hereby incorporated by reference).

Vascular Cell and Endothelial Cell Cords

In certain embodiments, the present disclosure provides engineered tissue seeds containing organized vascular or endothelial cell cords (cords) as created by a patterned biomaterial and extracellular matrix embedded in a scaffold template.

The patterned cords of the present disclosure promote the rapid formation of vessels that are spatially delineated, providing novel approaches to vascularizing engineered tissues, treating ischemic diseases, and promoting tissue healing and integration. Implantation of pre-formed cords into a subject can lead to engraftment, remodeling of the local microenvironment, anastomosis, and formation of stable capillaries within an implanted scaffold that directs blood vessels and blood flow. By employing cords generated in vitro, the subsequent formation of blood vessels in vivo is able to be spatially controlled.

The pre-organization of cells into patterned networks (i.e., cords or cylinders) provides a means to support rapid invasion and integration of host vasculature into the device to generate perfused, functional blood vessels by providing a pre-specified architecture as a template in which the new blood vessels mirror the diameter and architecture of the implanted cords. The architecture of the networks of cells engineered in vitro during the assembly of the patterned biomaterial defines the in vivo architecture (vessel diameters and network topology) of the blood vessel network that forms after implantation. Because these patterned networks act as "blood vessel highways" for the invading host tissue, their organization (patterned orientation, size, density, connectivity) can be engineered to rationally impact the rate and extent of host cell integration, and thus be used as a means to direct revascularization from a well perfused site to reach into and support ischemic tissues. In certain embodiments, the cells and matrix originally in the patterned biomaterial can be partially or entirely replaced by host cells and tissue, with the architecture of the patterned biomaterial being templated and preserved by the new host tissue.

Successful patterning of cells and subsequent formation of vessels in vivo constitutes a significant technical advance within the field of tissue engineering. As a result, the functional importance of tissue architecture is not limited to vascularization. As such, the concepts of tissue patterning of the present disclosure are widely applicable to many different types of engineered tissues and cell types.

Generating Engineered Tissue Seeds
Methods of Fabricating the Patterned Biomaterial In certain embodiments, the engineered tissue seed of the present disclosure can be formed by a process described herein. In certain embodiments, the method for fabricating cords and embedding these structures in extracellular matrix includes (1) generating 3D templates that have been defined with channels or trenches, (2) suspending endothelial cells in liquid collagen and centrifuging these cells into the channels of the template, (3) removing excess cell/collagen suspension to allow cord aggregates to form, and (4) removing cords from templates via encapsulation in an extracellular matrix scaffold.

In certain embodiments, the method for fabricating the patterned biomaterials is provided in Raghavan et al. (*Tissue Engineering Part A* (2010), Vol. 16(7): 2255-2263), the disclosure of which is incorporated herein by reference.

In certain embodiments, the method for fabricating the cord includes (1) suspending cells in a naturally-derived and/or synthetic scaffolding, (2) placing the suspended cells into the channels of a 3D template, and (3) allowing the cells to form one or more cords at least partially embedded in the naturally-derived and/or synthetic scaffolding. In certain embodiments, the method for fabricating the engineered tissue seeds as described herein can include the removal of the cords from the 3D template via encapsulation in an extracellular matrix scaffold. In certain embodiments, the cords are not encapsulated in an ECM scaffold.

In certain embodiments, organizing cells and material into spatial arrangements, such as cords and/or cell aggregates, can be accomplished by physically constraining the placement of cells/material by the use of wells or grooves, or injecting cells into microfluidic channels or oriented void spaces/pores. In certain embodiments, the cells can be organized by physically positioning cells with electric fields, magnetic tweezers, optical tweezers, ultrasound waves, pressure waves, or micromanipulators. In certain embodiments, cells can be organized by patterning the attachment of cells into specific arrangements by seeding them onto fibers. In certain embodiments, cells can be organized by novo fabrication such as by layer-by-layer or 3D printing.

In certain embodiments, the naturally-derived and/or synthetic scaffolding, can include, but is limited to, fibrin, fibrinogen, fibronectin, collagen, polyorthoester, polyvinyl alcohol, polyamide, polycarbonate, carbohydrates, agarose, alginate, poly(ethylene) glycol, polylactic acid, polyglycolic acid, polycaprolactone, polyvinyl pyrrolidone, a marine adhesive protein, cyanoacrylate, polymeric hydrogel, analogs, or a combination thereof. In certain embodiments, the naturally-derived and/or synthetic scaffolding is fibrin.

In certain embodiments, the engineered tissue seed can be formed by adding cells directly into or onto an extracellular matrix scaffold, in the absence of collagen. For example, cords can be formed by seeding cells without collagen into pre-existing hollow channels of a 3D template and encapsulating the cells into an ECM scaffold.

In certain embodiments, the engineered tissue seed does not contain the naturally-derived and/or synthetic scaffolding or the ECM scaffolding material. In certain embodiments, the engineered tissue seed as described herein is formed in the absence of ECM scaffolding.

In certain embodiments, the cords as described herein can contain two or more cell types. In certain embodiments, the two or more cell types can be co-introduced or sequentially introduced in the patterned biomaterial. For example, the two or more cell types can be introduced in the same spatial position, similar spatial positions, or different spatial positions, relative to each other. In certain embodiments, the two or more cell types are introduced into or onto different areas of the patterned biomaterial. For example, the cords and/or cell aggregates can be embedded in a naturally-derived and/or synthetic scaffolding, e.g., collagen, which can be further encapsulated in an ECM scaffold that is seeded with a distinct cell type.

In certain embodiments, the 3D templates can include naturally-derived and/or synthetic material. For example, the template can be composed of silicone or PDMS. In certain embodiments, the template can contain one or more channels. For example, the template can contain at least 1, 2, 3, 4, 5, 6, 7, 8, 9, 10, 15, 20, 30, or 40 channels. In certain embodiments, the one or more channels can be arranged in parallel formation. In certain embodiments, the one or more channels can be arranged in a non-parallel formation. In certain embodiments, the one or more channels can be organized with specific branch patterns such as rectilinear grids, bifurcated trees, in 2D or 3D organizations, with certain spacings of less than about 1 μm, greater than about 1 μm, 2, 4, 5, 8, 10, 15, 20, 25, 30, 40, 50, 80, 100, 150, 200, 250, 300, 500, 700, or 900 μm. The width of each line, groove and/or structure can be less than about 1 μm, greater than about 1 μm, 2, 4, 5, 8, 10, 15, 20, 25, 30, 40, 50, 80, 100, 150, 200, 250, 300, 500, 700, 900 μm, 1 mm, 2 mm, 5 mm, 10 mm, or 20 mm.

In certain embodiments, the template can contain one or more wells and/or grooves to form one or more cell aggregates. For example, the template can contain at least 1, 2, 3, 4, 5, 6, 7, 8, 9, 10, 15, 20, 30, or 40 wells. In certain embodiments, the one or more wells can be organized with certain spacings of less than about 1 μm, greater than about 1 μm, 2, 4, 5, 8, 10, 15, 20, 25, 30, 40, 50, 80, 100, 150, 200, 250, 300, 500, 700, 900 μm, 1 mm, 2 mm, 5 mm, 10 mm, or 20 mm.

In certain embodiments, the 3D template can be generated by molding, templating, photolithography, printing, deposition, sacrificial molding, stereolithography, or a combination thereof.

In certain embodiments, the ECM scaffold can function as the 3D template. For example, the engineered tissue seed can be formed by at least partially encasing the 3D template in an ECM scaffold. The 3D template can then be removed to create channels, wells and/or grooves in the ECM scaffold. Cells can then be added to the newly created channels, wells and/or grooves of the ECM scaffold to form cords and/or cell aggregates. In certain embodiments, the 3D template can be a carbohydrate lattice that dissolves following incubation in cell media to form empty channels, wells, and/or grooves in the ECM scaffold.

In certain embodiments, a patterned biomaterial can be fabricated through the use a custom 3D printer technology to extrude lattices of carbohydrate glass filaments with predefined diameters, spacings and orientations. In certain embodiments, soluble (clinical-grade, sterile) fibrinogen and thrombin are then combined and poured over the lattice. After the solution has polymerized into insoluble fibrin, the carbohydrate filaments are dissolved, leaving behind channels within the fibrin. The channels can then be filled with a suspension of cells, such as endothelial and perivascular cells, in a naturally-derived or synthetic scaffolding (e.g., soluble type I collagen) that subsequently is polymerized to trap the cells within the channels to form cords.

Patterned Cell Structures

In certain embodiments, the cords and/or cell aggregates of engineered tissue seeds as described herein can be formed from any cell type using any naturally-derived or synthetic scaffolding, including, but not limited to peptides, proteins, carbohydrates, matrigel, hyaluronic acid, collagen, fibrin, fibrinogen, fibronectin, polyorthoester, polyvinyl alcohol, polyamide, polycarbonate, agarose, alginate, poly(ethylene) glycol, polylactic acid, polyglycolic acid, polycaprolactone, polyvinyl pyrrolidone, a marine adhesive protein, cyanoacrylate, polymeric hydrogel, analogs, or a combination thereof. Additional examples of scaffolding are disclosed in U.S. Pat. No. 8,318,193 and U.S. Patent Application No. 20012/0288564, which are incorporated in their entirety by reference herein.

In certain embodiments, the scaffolding can be collagen. For example, the cells can be suspended in collagen and placed in the channels or wells of a 3D template to form organized cords and/or cell aggregates in a collagen scaffold. In certain embodiments, the cells can be placed between two layers of collagen in the channels of a 3D template.

In certain embodiments, the collagen is human collagen, recombinant collagen, or recombinant human collagen. In certain embodiments, the liquid collagen can contain collagen type I, type II, type III, type IV, type V, type VI, type VII, type VIII, type IX, type X, type XI, type XII, type XIII, type XIV, type XV, type XVI, type XVII, type XVIII, type XIX, type XX, type XXI, type XXII, type XXIII, type XXIV, type XXV, type XXVI, XXVII, type XXVIII, or type XXIX, or mixtures thereof. In certain embodiments, the collagen is Type I collagen and/or approved for clinical use. In certain embodiments, the collagen is obtained from an animal, including, but not limited to, mouse, rat, bovine, and porcine.

In certain embodiments, the naturally-derived or synthetic scaffolding can be degradable upon exposure to environmental conditions. For example, the ECM scaffold can be degraded by the presence of hydrolytic enzymes, presence of proteasomal enzymes, pH lower than 5 and reducing conditions.

In certain embodiments, the cords and/or cell aggregates of engineered tissue seeds as described herein can be formed without using any naturally-derived or synthetic scaffolding.

In certain embodiments, the cords and/or cell aggregates of the engineered tissue seeds as described herein can be formed from a monotypic suspension of cells. In certain embodiments, a monotypic suspension of cells suspended in liquid collagen can be used. For example, human mesenchymal stem cells or neuronal cells can be used. In certain embodiments, the monotypic suspension of cells contains endothelial cells.

In certain embodiments, the cords and/or cell aggregates of the engineered tissue seeds as described herein can be formed from a heterotypic suspension of cells. For example, the cords of the engineered tissue seeds as described herein can be formed from a heterotypic suspension of cells suspended in liquid collagen. In certain embodiments, the heterotypic suspension of cells of the cords and/or cell aggregates contains two or more cell types.

In certain embodiments, the cell suspension can contain endothelial cells. In certain embodiments, the endothelial cells are adult vein endothelial cells, adult artery endothelial cells, embryonic stem cell-derived endothelial cells, iPS-derived endothelial cells, umbilical vein endothelial cells, umbilical artery endothelial cells, endothelial progenitors cells derived from bone marrow, endothelial progenitors cells derived from cord blood, endothelial progenitors cells derived from peripheral blood, endothelial progenitors cells derived from adipose tissues, endothelial cells derived from adult skin, or a combination thereof. In certain embodiments, the umbilical vein endothelial cells are human umbilical vein endothelial cells (HUVEC).

In certain embodiments, the cell suspension can contain fibroblast and/or fibroblast-like cells. In certain embodiments, the fibroblasts are human foreskin fibroblasts, human embryonic fibroblasts, mouse embryonic fibroblasts, skin fibroblasts cells, vascular fibroblast cells, myofibroblasts, smooth muscle cells, mesenchymal stem cells (MSCs)-derived fibroblast cells, or a combination thereof. In certain embodiments the fibroblasts are normal human dermal fibroblasts (NHDFs).

In certain embodiments, the cell suspension can contain tissue-specific cells. The tissue-specific cells can be muscle cells, pancreatic beta cells, osteoblasts, chondrocytes, myoblasts, adipocytes, neuronal cells, glial cells, cardiomyocytes, liver cells, urethral cells, kidney cells, periosteal cells, bladder cells, odontoblasts, dental pulp cells, periodontal cells, tenocytes, lung cells, cardiac cells, skeletal cells, stem cell or iPS-cell derived tissue specific cells, or a combination thereof. In certain embodiments, the tissue-specific cells are muscle cells, pancreatic beta-islet cells, cardiomyocytes, liver cells, lung cells, neural cells, bone or kidney cells, or a combination thereof.

In certain embodiments, the tissue-specific cells are of a neuronal cell type, including, but not limited to, astrocytes, glial cells, neuronal cells, or neuronal stem cells.

In certain embodiments, the heterotypic cell suspension can contain, for example, at least one of the following cell types: endothelial cells, fibroblast cells, pericytes, mesenchymal stem cells, smooth muscle cells, any other cell type that exhibits fibroblast-like properties, epithelial cells, neuronal cells, stem cells, lung cells, kidney cells, pancreatic cells, cardiac cells, liver cells, skeletal cells, urethral cells, progenitor cells, or a combination thereof.

In certain embodiments, the cells present in the heterotypic cell suspension can be in a ratio of about 50:1, 20:1, 10:1, 5:1, 2:1, or 1:1, with endothelial cells generally being the predominant cell present in the heterotypic suspension, but these ratios can vary depending on the type of cells involved. One of ordinary skill in the art, with the benefit of this disclosure, will be able to determine the appropriate ratio of cell types in a heterotypic suspension to achieve the objectives of the present disclosure.

In certain embodiments, the ratio of endothelial cells to other cell types present in the cell suspension can be from about 1:1000, about 1:100, about 50:1, about 30:1, about 20:1, about 19:1, about 18:1, about 17:1, about 16:1, about 15:1, about 14:1, about 13:1, about 12:1, about 11:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10, about 1:11, about 1:12, about 1:13, about 1:14, about 1:15, about 1:16, about 1:17, about 1:18, about 1:19, about 1:20, about 1:30, about 1:50, about 1:100 or about 1:1000. In certain embodiments, the ratio of endothelial cells to other cell types can be from about 50:1 to about 1:3.

In certain embodiments, the endothelial cells can be present in the cell suspension at a volume percentage from about 1%, 5%, 10%, 15%, 20%, 25%, 30%, 33%, 40%, 50%, 66%, 75%, 80%, 90%, 95%, 99%, or 100%. In certain embodiments, the endothelial cells are present in the cell suspension at a volume percentage from about 30%.

Cells suitable for forming the cords and/or cell aggregates of the engineered tissue seeds as described herein can be derived from any suitable source. The subject to receive the implant of the engineered tissue seeds as described herein can determine the source of the cells to form the cords and/or cell aggregates of the engineered tissue seed. In certain embodiments, the cells can be derived from an autologous source. For example, the cells can be derived from the subject to be implanted with the engineered tissue seeds as described herein. For example, endothelial cells can be derived from the skin of the subject to be implanted with the engineered tissue seed. In certain embodiments, endothelial cells can be obtained from any tissue in the body, including, but not limited to, umbilical cord, skin, heart, liver, kidney, adrenals, brain, muscle, bone, bone marrow and fat tissue. In certain embodiments, endothelial cells can also be generated from stem cells derived from various sources that are then differentiated into endothelial cells. In certain embodiments, cells can be cultured for a period of time under various conditions to induce certain phenotypes before patterning into the cords and/or cell aggregates.

In certain embodiments, the engineered tissue seed contains a combination of at least one type of endothelial cell and at least one other cell type for the formation of a three-dimensional engineered tissue containing an internal blood vessel architecture.

A heterotypic cell suspension of cells of the engineered tissue seeds as described herein can have certain advantages over the use of a monotypic suspension of endothelial cells. First, a heterotypic cell suspension having endothelial cells enhances cord formation by increasing contraction of the cell/ECM gels within the channels or trenches of the template. The resulting cords have a reduced cord diameter as compared to the channel/trench width of the template. Second, in certain instances, endothelial cells can survive and function better in the presence of other cell types.

The properties of the cords of the present disclosure can be varied to suit a particular application. In certain embodiments, the density of the cords can be changed. In certain embodiments, cords of different diameters and shapes can be fabricated. Examples of the certain shapes and diameters that the cords can be fabricated into include, but are not limited to, cylindrical, Y-shaped, and T-shaped structures. In certain embodiments, the overall network organization of cords can be defined, for example, by the number and location of branchpoints, connections, three-dimensional organization, degree of anisotropy, alignment, diameters, lengths, and the like. In certain embodiments, the organization of the one or more cords within the patterned biomaterial can be arranged to dictate the organization of the new vasculature and the directionality of blood flow. For example, the one or more cords can be organized in a parallel arrangement. In certain embodiments, the one or more cords can be organized in a non parallel arrangement.

In certain embodiments, the cords can be organized with specific branch patterns such as rectilinear grids, bifurcated trees, in 2D or 3D organizations. In certain embodiments, the spacing between adjacent cords can be less than about 1 µm, greater than about 1 µm, 2 µm, 4 µm, 5 µm, 8 µm, 10 µm, 15 µm, 20 µm, 25 µm, 30 µm, 40 µm, 50 µm, 80 µm, 100 µm, 150 µm, 200 µm, 250 µm, 300 µm, 500 µm, 700 µm, 900 µm, 1 mm, 2 mm, 5 mm, 10 mm, or 20 m or a combination thereof.

In certain embodiments, the width and/or diameter of the one or more cords of the present disclosure can be less than about greater than about 1 µm, 2 µm, 4 µm, 5 µm, 8 µm, 10 µm, 15 µm, 20 µm, 25 µm, 30 µm, 40 µm, 50 µm, 80 µm, 100 µm, 150 µm, 200 µm, 250 µm, 300 µm, 500 µm, 700 µm, 900 µm, 1 mm, 2 mm, 5 mm, 10 mm, or 20 mm or a combination thereof.

In certain embodiments, the length of the one or more cords of the engineered tissue seed can be greater than about 1 µm, 2 µm, 4 µm, 5 µm, 8 µm, 10 µm, 15 µm, 20 µm, 25 µm, 30 µm, 40 µm, 50 µm, 80 µm, 100 µm, 150 µm, 200 µm, 250 µm, 300 µm, 500 µm, 700 µm, 900 µm, 1 mm, 2 mm, 5 mm, 10 mm, or 20 mm or a combination thereof.

In certain embodiments, the number of cords contained within the engineered tissue seeds can vary. In certain embodiments, the engineered tissue seed includes at least 1, 2, 3, 4, 5, 10, 15, 20, 25, 30, 35, 50, 100, 150, 200, 300, 400, 500, 1000, 10,000, 100,000, or 1,000,000 organized cords. For example, in treatment areas where high vascular density is required or desired, the number of cords in the patterned biomaterial can be increased to the proper number. In certain embodiments, in treatment areas where lower vascular density is required or desired, the number of cords in the engineered tissue seed can be modified to the proper number to achieve the desired vascular density.

In certain embodiments, the properties of each cord within an engineered tissue seed can differ. For example, each cord of an engineered tissue seed can have different properties, such as diameter, length, density, shape and pattern. In certain embodiments, the spacing between a subset of cords can differ from the spacing between another subset of cords of the same engineered tissue seed. In certain embodiments, the 3D arrangement or pattern of a subset of cords can differ from the 3D arrangement or pattern of another subset of cords. In certain embodiments, the density, length, shape, or diameter of a subset of cords can differ from the density, length, shape, or diameter of another subset of cords.

In certain embodiments, sections of the engineered tissue seed can contain one or more cords of different alignments. For example, in one section of the engineered tissue seed, the one or more cords can be organized in a parallel arrangement and in a different section of the engineered tissue seed, the one or more cords can be organized in a non-parallel arrangement.

In certain embodiments, each cord of the engineered tissue seed can be comprised of a different cell type. For example, one cord of the engineered tissue seed can be comprised of endothelial cells and another cord of the same engineered tissue seed can be comprised of epithelial cells.

In certain embodiments, the diameters of the cords can include, but are not limited to, 75 µm, 150 µm, and/or 500 µm. One of ordinary skill in the art, with the benefit of this disclosure, will be able to optimize the cord arrangement and properties of the cords, including but not limited to, the cells used in their formation, the number, size, aspect ratio, and orientation, to meet the specific requirements for a particular tissue engineering application.

The properties of the cell aggregates of the present disclosure can be varied to suit a particular application. In certain embodiments, the density of the cell aggregates can be changed. In certain embodiments, cell aggregates of different diameters can be fabricated. In certain embodiments, the overall network organization of the one or more cell aggregates can be defined, for example, by the number, three-dimensional organization, alignment, diameters, density, and the like.

In certain embodiments, the width and/or diameter of the one or more cell aggregates of the present disclosure can be greater 1 µm, 2 µm, 4 µm, 5 µm, 8 µm, 10 µm, 15 µm, 20 µm, 25 µm, 30 µm, 40 µm, 50 µm, 80 µm, 100 µm, 150 µm, 200 µm, 250 µm, 300 µm, 500 µm, 700 µm, 900 µm, 1 mm, 2 mm, 5 mm, 10 mm, or 20 mm or a combination thereof.

In certain embodiments, the spacing between adjacent cell aggregates can be greater than about 1 µm, 2 µm, 4 µm, 5 µm, 8 µm, 10 µm, 15 µm, 20 µm, 25 µm, 30 µm, 40 µm, 50 µm, 80 µm, 100 µm, 150 µm, 200 µm, 250 µm, 300 µm, 500 µm, 700 µm, 900 µm, 1 mm, 2 mm, 5 mm, 10 mm, or 20 mm or a combination thereof.

In certain embodiments, the number of cell aggregates contained within the engineered tissue seed can vary. In certain embodiments, the engineered tissue seed includes at least 1, 2, 3, 4, 5, 10, 15, 20, 25, 30, 35, 50, 100, 150, 200, 300, 400, 500, 1000, 10,000, 100,000, or 1,000,000 organized cell aggregates.

In certain embodiments, the properties of each cell aggregate within an engineered tissue seed can differ. For example, each cell aggregate of an engineered tissue seed can have different properties, such as diameter, density, shape, 3D organization, and pattern. In certain embodiments, the spacing between a subset of cell aggregates can differ from the spacing between another subset of cell aggregates. In certain embodiments, the 3D arrangement or pattern of a subset of cell aggregates can differ from the 3D arrangement or pattern of another subset of cell aggregates. In certain embodiments, the density, shape, or diameter of a subset of cell aggregates can differ from the density, shape, or diameter of another subset of cell aggregates.

In certain embodiments, sections of the engineered tissue seed can contain one or more cell aggregates of different alignments. For example, in one section of the engineered tissue seed, the one or more cell aggregates can be organized in the same plane of the engineered tissue seed, and in a different section of the engineered tissue seed, the one or more cell aggregates can be organized in a different plane of the engineered tissue seed.

In certain embodiments, each cell aggregate of the engineered tissue seed can be comprised of a different cell type. For example, one cell aggregate of the engineered tissue seed can be comprised of endothelial cells and another cell aggregate of the same engineered tissue seed can be comprised of pancreatic beta-islet cells.

In certain embodiments, the engineered tissue seed can contain one or more cords and one or more cell aggregates. In certain embodiments, the arrangement and organization of the one or more cords and the one or more one cell aggregates of the engineered tissue seed can vary. For example, the spacing between the one or more cords can differ from the spacing between the one or more cell aggregates.

In certain embodiments, the one or more cell aggregates and the one or more cords of the engineered tissue seed can be comprised of different cell types. For example, the one or more cell aggregates of the engineered tissue seed can be comprised of neuronal cells and the one or more cords of the same engineered tissue seed can be comprised of endothelial cells. In certain embodiments, the one or more cell aggregates and the one or more cords of the engineered tissue seed can be comprised of the same cell type. For example, the one or more cell aggregates and the one or more cords of an engineered tissue seed can be comprised of endothelial cells.

In certain embodiments, the engineered tissue seed can include at least one cord and at least one cell aggregate. In certain embodiments, the at least one cord can be organized in a different section of the engineered tissue seed than the at least one cell aggregate. For example, one section of the engineered tissue seed can be comprised of the at least one cord, whereas another section of the engineered tissue seed can be comprised of the at least one cell aggregate. In certain embodiments, the at least one cord and the at least one cell aggregate can be organized in the same section of the engineered tissue seed.

In certain embodiments, the engineered tissue seed can contain one or more bioactive substances. Examples of bioactive substance(s) include, but are not limited to, hormones, neurotransmitters, growth factors, hormone, neurotransmitter or growth factor receptors, interferons, interleukins, chemokines, cytokines, colony stimulating factors, chemotactic factors, extracellular matrix components, and adhesion molecules, ligands and peptides; such as growth hormone, parathyroid hormone (PTH), bone morphogenetic protein (BMP), transforming growth factor-.alpha. (TGF-.alpha.), TGF-.beta.1, TGF-.beta.2, fibroblast growth factor (FGF), granulocyte/macrophage colony stimulating factor (GMCSF), epidermal growth factor (EGF), platelet derived growth factor (PDGF), insulin-like growth factor (IGF), scatter factor/hepatocyte growth factor (HGF), fibrin, collagen, fibronectin, vitronectin, hyaluronic acid, an RGD-containing peptide or polypeptide, an angiopoietin and vascular endothelial cell growth factor (VEGF). For example, the engineered tissue seed can include a biologically effective amount of VEGF and cords of endothelial cells. In certain embodiments, the engineered tissue seed can be free from exogenous bioactive substances.

The ECM Scaffold

In certain embodiments, the extracellular matrix (ECM) scaffold of the engineered tissue seed as described herein can include any native or synthetic ECM material. In certain embodiments, the ECM scaffold can have one or more native and/or synthetic matrix materials.

In certain embodiments, the ECM scaffold can include peptides, proteins, carbohydrates, collagen, fibrin, fibrinogen, matrigel, agarose, polyethylene glycol, dextran, hyaluronic acid, or a combination thereof. For example in certain embodiments, the ECM scaffold can include collagen or fibrin.

In certain embodiments, the ECM scaffold can include a physical solid support such as silicone rubber, plastics, glass, hydroxyappetite, poly-lactic acid, poly-glycolic acid, or other materials.

In certain embodiments, where the engineered tissue seed is used to aid vascularization, fibrin can be used as the ECM scaffold material. Other suitable ECM materials can be used as a scaffold, depending on the specific purpose for the implant and based on the properties of the ECM material, including but not limited to, the degradation properties of the ECM materials.

In certain embodiments, the ECM scaffold can be degradable upon exposure to environmental conditions. For example, the ECM scaffold can be degraded by the presence of hydrolytic enzymes, presence of proteasomal enzymes, pH lower than 5 and reducing conditions.

In certain embodiments, the ECM scaffold can have different properties, a different composition, or elicit different responses from the host cells than the naturally-derived or synthetic scaffolding used to form the cords and/or cell aggregates. For example, the naturally-derived or synthetic scaffolding used to form the cords and/or cell aggregates can degrade at a different rate than the ECM scaffolding. In certain embodiments, the naturally-derived or synthetic scaffolding used to form the cords and/or cell aggregates degrades faster than the ECM scaffolding.

In certain embodiments, the naturally-derived or synthetic scaffolding used to form the cords and/or cell aggregates can release bioactive substances compared to the ECM scaffold. For example, naturally-derived or synthetic scaffolding used to form the cords and/or cell aggregates can release pro-angiogenic factors.

In certain embodiments, the composition of the ECM scaffold differs from the composition of the naturally-derived or synthetic scaffolding used to form the cords and/or cell aggregates. For example, the naturally-derived or synthetic scaffolding can contain collagen and the ECM scaffold can contain fibrin.

In certain embodiments, the composition of the ECM scaffold can be the same as the composition of the naturally-derived or synthetic scaffolding used to form cords and/or cell aggregates. For example, the naturally-derived or synthetic scaffolding and the ECM scaffold can both contain collagen.

In certain embodiments, the cords and/or cell aggregates can be encapsulated in an ECM scaffold comprising cells of a distinct cell type. In certain embodiments, the ECM scaffold of the engineered tissue seed can be seeded with cells. In certain embodiments, the ECM scaffold can be comprised of one or more cell types. Cells can confer tissue functionality and provide structures, which can replace or facilitate the repair of a tissue of the subject. For example, the ECM scaffold can include, but is not limited to, muscle cells to provide contractile structures, vascular and/or neural cells to provide conductive elements, metabolically active secretory cells, such as liver cells, hormone synthesizing cells, sebaceous cells, pancreatic islet cells or adrenal cortex cells to provide secretory structures, stem cells, such as bone marrow-derived or embryonic stem cells, dermal fibroblasts, skin keratinocytes, Schwann cells for nerve implants, smooth muscle cells and endothelial cells for vessel structures, urothelial and smooth muscle cells for bladder/urethra structures and osteocytes, chondrocytes, and tendon cells for bone and tendon structures, or a combination thereof. In certain embodiments, the ECM scaffold can include other cell types including, but not limited, to hepatocytes and chondrocytes.

In certain embodiments, the ECM scaffold can contain at least one cell of at least one cell type. For example, the ECM scaffold can contain at least one hepatocyte or at least one pancreatic beta-islet cell. In certain embodiments, the ECM scaffold can contain at least one cell of at least two cell types.

Cells suitable for inclusion in the ECM scaffold of the engineered tissue seed of the present disclosure can be derived from any suitable source. The subject to receive the implant of the engineered tissue seed of the present disclosure can determine the source of the cells to be included in the ECM scaffold. In certain embodiments, the cells can be derived from an autologous source. For example, the cells can be derived from the subject to be implanted with the engineered tissue seed. For example, epithelial cells can be derived from the skin of the subject to be implanted with the engineered tissue seed. In certain embodiments, the cells can also be generated from stem cells derived from various sources that are then differentiated into the desired cell type. For example, the stem cells can be derived from the subject to be implanted with the engineered tissue seed. In certain embodiments, cells can be cultured for a period of time under various conditions to induce certain phenotypes before placing the cells in the ECM scaffold.

In certain embodiments, the ECM scaffold can include an engineered tissue construct. For example, an engineered tissue construct can be encapsulated in the ECM scaffold.

In certain embodiments, the engineered tissue seed can be comprised of cords and/or cell aggregates of endothelial cells formed in a naturally-derived or synthetic scaffolding that is at least partially encapsulated in an ECM scaffolding comprising cells of a distinct cell type. For example, the ECM scaffolding can be seeded with cells, including, but not limited to, pancreatic cells, cardiac cells, skim cells muscles cells, fat cells, or bone cells.

In certain other embodiments, the patterned biomaterial of the present disclosure can be encapsulated within another biomaterial or engineered tissue.

In certain embodiments, the cords can be lifted out of their template and handled or used as a suspension of the cords without a separate ECM scaffold.

In certain embodiments, the cords of the engineered tissue seed of the present disclosure can be embedded in the ECM scaffold in a parallel arrangement. In certain embodiments, the cords can be embedded in the ECM scaffold in a non-parallel arrangement.

In certain embodiments, the ECM scaffolding can contain one or more bioactive substances. Examples of bioactive substance(s) include, but are not limited to, hormones, neurotransmitters, growth factors, hormone, neurotransmitter or growth factor receptors, interferons, interleukins, chemokines, cytokines, colony stimulating factors, chemotactic factors, extracellular matrix components, and adhesion molecules, ligands and peptides; such as growth hormone, parathyroid hormone (PTH), bone morphogenetic protein (BMP), transforming growth factor-α (TGF-α), TGF-β1, TGF-β2, fibroblast growth factor (FGF), granulocyte/macrophage colony stimulating factor (GMCSF), epidermal growth factor (EGF), platelet derived growth factor (PDGF), insulin-like growth factor (IGF), scatter factor/hepatocyte growth factor (HGF), fibrin, collagen, fibronectin, vitronectin, hyaluronic acid, an RGD-containing peptide or polypeptide, an angiopoietin and vascular endothelial cell growth factor (VEGF). For example, the patterned biomaterial can include a biologically effective amount of VEGF. In certain embodiments, the ECM scaffolding can contain at least one cell of one cell type and at least one bioactive agent. In certain embodiments, the ECM scaffolding can be free from exogenous bioactive substances.

Encapsulation

Biopolymers suitable for use include any polymer that is gellable in situ, i.e., one that does not require chemicals or conditions (e.g., temperature, pH) that are not cytocompatible. In certain embodiments, polymers are synthetic or natural biopolymers (i.e., are biocompatible.) This includes both stable and biodegradable biopolymers. Biodegradable polymers are useful, for example, where proliferation of one or more populations of the encapsulated cells is desired. Polymers that can be used in the methods and constructs described herein include, but are not limited to, PEG hydrogels, poly(lactic-co-glycolic acid) (PLGA), hydroxyethyl methacrylate (HEMA), gelatin, fibrin, matrigel, alginate, agarose, polysaccharides, collagen, hyaluronic acid (HA), peptide-based self-assembling gels, thermo-responsive poly (NIPAAm). A number of biopolymers are known to those skilled in the art (Bryant and Anseth, 2001; Mann et al., 2001; and Peppas et al., 2000; all incorporated by reference).

Polymers for use herein are preferably crosslinked, for example, ionically crosslinked. In certain embodiments, the methods and constructs described herein use polymers in which polymerization can be promoted photochemically (i.e., photocrosslinked), by exposure to an appropriate wavelength of light (i.e., photopolymerizable) or a polymer which is weakened or rendered soluble by light exposure or other stimulus. Although some of the polymers listed above are not inherently light sensitive (e.g. collagen, HA), they may be made light sensitive by the addition of acrylate or other photosensitive groups.

In certain embodiments, the method utilizes a photoinitiator. A photoinitiator is a molecule that is capable of promoting polymerization of hydrogels upon exposure to an appropriate wavelength of light as defined by the reactive groups on the molecule. In the context of the disclosure, photoinitiators are cytocompatible. A number of photoinitiators are known that can be used with different wavelengths of light. For example, 2,2-dimethoxy-2-phenyl-acetophenone, HPK 1-hydroxycyclohexyl-phenyl ketone and Irgacure 2959 (hydroxyl-1-[4-(hydroxyethoxy)phenyl]-2methyl-1propanone) are all activated with UV light (365 nm). Other crosslinking agents activated by wavelengths of light that are cytocompatible (e.g. blue light) can also be used with the methods described herein.

In other embodiments, the method involves the use of polymers bearing non-photochemically polymerizable moieties. In certain embodiments, the non-photochemically polymerizable moieties are Michael acceptors. Non-limiting examples of such Michael acceptor moieties include α,β-unsaturated ketones, esters, amides, sulfones, sulfoxides, phosphonates. Additional non-limiting examples of Michael acceptors include quinines and vinyl pyridines. In some embodiments, the polymerization of Michael acceptors is promoted by a nucleophile. Suitable nucleophiles include, but are not limited to thiols, amines, alcohols and molecules possessing thiol, amine and alcohol moieties. In certain embodiments, the disclosure features use of thermally cross-linked polymers.

In certain embodiments, patterned cells suitable for the constructs and methods described herein are localized in specked locations that may occur in repeating structures within 3-dimensional biopolymer rather than being randomly localized throughout 3-dimensional slab of biopolymer, on the surface of a regularly or irregularly shaped 3-dimensional scaffold, or patterned on a 2-dimensional support (e.g. on a glass slide). The cells can be patterned by locating the cells within specific regions of relatively homogeneous slabs of biopolymers (resolution up to about 5 microns) or by creating patterned biopolymer scaffolds of defined patterns wherein the living cells are contained within the hydrogel (resolution up to about 100 microns). Patterning is performed without direct, mechanical manipulation or physical contact and without relying on active cellular processes such as adhesion of the cells.

Relatively homogeneous slab of biopolymer refers to a polymerized biopolymer scaffold that is approximately the same thickness throughout and is essentially the same shape of the casting or DEP chamber in which it was polymerized.

Patterned biopolymer scaffold refers to a biopolymer scaffold that is of a substantially different shape than the casting or DEP chamber in which it was polymerized. The pattern could be in the form of shapes (e.g. circles, stars, triangles) or a mesh or other form. In some embodiments, the biopolymer is patterned to mimic in vivo tissue architecture, such as branching structures.

The methods for use herein can be used for the production of any of a number of patterns in single or multiple layers including geometric shapes or a repeating series of dots with the features in various sizes. Alternatively, multilayer biopolymer gels can be generated using a single mask turned in various orientations. The formation of high resolution patterned cells in 3-dimensions can be achieved by methods other than photopolymerization, such that the limitations of the method are overcome.

Stereolithography via photopatterning may be used to introduce perfusion channels, thus significantly improving diffusive transport of oxygen and nutrients to photoencapsulated hepatocytes. In some embodiments, the perfusion channel consists of a single-layer hexagonal branching pattern.

Cells may be patterned within the hydrogel by selective polymerization of the biopolymer or by patterning of the cells using an electrical field or both. Theoretically a single cell can be patterned by locating it in a specific position within a biopolymer; however, in some embodiments a plurality of cells, at least 10, at least 20, at least 100, at least 500 cells, are patterned. Patterning does not require localization of all cells to a single, discrete location within the biopolymer. Cells can be localized, in lines one or two or many cells wide, or in multiple small clusters throughout a relatively homogeneous biopolymer scaffold (e.g. approximately 20,000 clusters of 10 cells each in a single scaffold). The 3-dimensional patterning can also include patterning of cells or other particles in a single plane by DEP as the cells are contained in a three dimensional scaffold. The cell patterning methods described herein, can also be used for patterning of organelles, liposomes, beads and other particles.

Cell organization can be controlled by photopatterning of the hydrogel structure. The photopolymerizable nature of acrylate-based PEG hydrogels enables the adaptation of photolithographic techniques to generate patterned hydrogel networks. In this process, patterned masks printed on transparencies act to localize the UV exposure of the prepolymer solution, and thus, dictate the structure of the resultant hydrogel.

In certain embodiments, hepatocellular hydrogel constructs with defined cellular configurations may be prepared by photopatterning PEG hydrogels containing primary hepatocytes and fibroblasts, resulting in a hydrogel network consisting of 3D hepatocyte 'aggregates' surrounded by regions containing encapsulated fibroblasts. Further control of cell orientation within these patterned domains may be achieved utilizing dielectrophoretic patterning techniques. Dielectrophoresis (DEP) can be used alone for patterning of cells in relatively homogeneous slabs of hydrogel or in conjunction with the photopolymerization method. The methods allow for the formation of three dimensional scaffolds from hundreds of microns to tens of centimeters in length and width, and tens of microns to hundreds of microns in height. A resolution of up to 100 microns in the photopolymerization method and possible single cell resolution (10 micron) in the DEP method is achievable. Photopolymerization apparatus, DEP apparatus, and other methods to produce 3-dimensional co-cultures are described in U.S. patent application Ser. No. 11/035,394, which is incorporated herein by reference.

In other embodiments, the biopolymers may additionally contain any of a number of growth factors, adhesion molecules, degradation sites or bioactive agents to enhance cell viability or for any of a number of other reasons. Such molecules are well known to those skilled in the art.

In certain embodiments, cells are encapsulated at a concentration or density of about $0.1 \times 10^6$/ml to about $100 \times 10^6$/ml, or about $0.1 \times 10^6$/ml to about $20 \times 10^6$/ml, about $0.5 \times 10^6$/ml, 1, 2, 5, 10 or $15 \times 10^6$/ml. In certain embodiments, non-parenchymal cells of a non-parenchymal cell population cell type are encapsulated at a ratio (as compared to parenchymal cells) of about 0.1:1, 0.5:1, 1:1, 1.5:1, 2:1, 3:1, 5:1 or 10:1. In some embodiments, the parenchymal cell:non-parenchymal cell:endothelial cell ratio is 1:2:1. In some embodiments, the hepatocytes:fibroblast:endothelial cell ratio is 1:2:1. In some embodiments, the above values or ranges are at the time of encapsulation. In some embodiments, the above values or ranges are at a time following encapsulation or implantation, e.g., at about 1, 2, 5, 12, 24, 36, 48, 72, 96 or more hours after encapsulation or implantation, i.e., the cells, e.g., the parenchymal cells and/or one or more non-parenchymal cell populations are encapsulated at a lower concentration or density and proliferate to achieve the indicated concentration or density after a certain time in culture or in vivo.

Primary hepatocytes representing the full complement of liver functions and drug metabolism pathways are ideal cells for building implantable human liver mimetics but are challenging to maintain upon isolation. The survival and function of primary hepatocytes within PEG hydrogels is recognized to be highly dependent on microenvironmental factors, including the interactions of hepatocyte-nonparenchymal cell with stromal fibroblasts. As previously described in US 2012/0216304, co-cultivation of hepatocytes with fibroblasts (HEP/FIB) for one-week followed by encapsulation in PEG-DA at a $8 \times 10^6$ hep/ml final density (~$0.5 \times 10^6$ total encapsulated hepatocytes) sustained hepatocyte functions, albumin secretion and urea synthesis, whereas hepatocytes encapsulated at the same density alone (HEP) declined over two to four days of culture. As described infra, the addition of fibroblasts (e.g., NHDFs) to hepatocytes aggregates enhanced albumin production. Similarly, albumin promoter activity was enhanced in animals grafted with tissue seeds containing hepatic aggregates with both NHDFs and hepatocytes compared to hepatocytes without NHDFs.

PEG hydrogels, due to their resistance to non-specific protein adsorption, are generally non-adhesive and do not support cell attachment. Incorporation of adhesive peptides into hydrogel networks enhances adhesion and modulates function for a wide range of cell types. Specifically, the presence of the RGDS peptide within PEG hydrogel enhances hepatocyte function.

The tunability of PEG scaffold chemistry allows manipulation of cell-matrix interactions of encapsulated human hepatocytes in vitro. NHS ester chemistry may be used to conjugate RGDS, or the negative control RGES peptide, to acrylate PEG monomers. In some embodiments, incorporation of said functionalized monomers within the hydrogel network improves encapsulated cells synthetic and secretory functions by two- to three-fold compared to RGES controls cultured over one week in vitro. Other conjugation chemistries are well-know in the art and interchangeable with the NHS chemistries exemplified herein.

In one aspect, the present disclosure provides a method of making an implantable human liver tissue construct, comprising obtaining a co-culture comprising a population of human hepatocytes and a population of non-parenchymal cells supporting hepatocellular viability and function; and encapsulating the co-culture in a biocompatible, hydrogel scaffold, derivatized with one or more cell-adhesive peptides, wherein the populations of cells are homogeneously distributed in the hydrogel in a manner permitting contact between the hepatocytes and the non-parenchymal cells.

In some embodiments of the method, the hydrogel is photopolymerized polyethylene glycol (PEG) hydrogel. In some embodiments of the method, the photopolymerized polyethylene glycol (PEG) hydrogel is a polyethylene glycol-diacrylate (PEG-DA) hydrogel. In some embodiments of the method, the non-parenchymal cells are stromal cells. In some embodiments, the stromal cells are fibroblasts. In some embodiments of the method, the hydrogel contains about $8 \times 10^6$ hepatocytes/ml. In some embodiments of the method, the hydrogel contains about $24 \times 10^6$ fibroblasts/ml (e.g., at the time of encapsulation).

The above methods and constructs may further comprise a population of human liver-derived non-parenchymal cells, wherein the population of liver-derived non-parenchymal cells is distributed in the hydrogel in manner preventing contact with the co-cultured hepatocytes:non-parenchymal cells. In some embodiments, the human liver-derived non-parenchymal cells are human liver endothelial cells (LECs). In some embodiments, the hydrogel contains about $6 \times 10^6$ LECs/ml (e.g., at the time of encapsulation). In some embodiments, the LECs are TMNK-1 cells. In certain embodiments of the above methods, the construct has a diameter of about 20 mm and a thickness of about 250 µm, the construct comprising about $0.5 \times 10^6$ human hepatocytes. In certain embodiments, the constructs are discs having a diameter of about 5-50 mm, preferably about 10-30 mm, for example, about 15, 20 or 25 mm in diameter and a thickness of about 50-1000 µm, 100-500 µm, 200 µm, 250 µm or 300 µm.

The hydrogel may be polymerized homogeneously or through a mask to result in selective photopolymerization and patterning of the biopolymer. In some embodiments, other ways of photopatterning are used including, but not limited to, shining light through an emulsion mask, and also including shining light in a pattern through a digital pattern generator or scanning a laser in a pattern as in stereolithography or using a hologram. In certain embodiments of the above methods, the hydrogel comprises perfusion channels supporting diffusive transport of oxygen and/or nutrients. In some embodiments of the above methods, the scaffold is biodegradable. Photopatterning allows thicker constructs of to be utilized due to increased nutrient and/or oxygen transport to encapsulated cells.

In certain embodiments of the above methods, the cell-adhesive peptide is an extracellular matrix- (ECM-) derived peptide. In some embodiments, the ECM-derived peptide is an RGDS peptide. In some embodiments, the RGDS peptide is covalently attached to a component of the hydrogel. In some embodiments, the RGDS peptide is covalently attached to an acrylate PEG monomer polymerized in the hydrogel. ECM-derived peptides can be included, for example, at a concentration of about 1-100 µM/ml, for example, at a concentration of about 2-50100 µM/ml or about 5-20100 µM/ml.

Soluble factors can be included at about 1-1000 ng/ml and, in some embodiments, can be included at up to, for example, 100 µg/ml. Soluble factors can be added or released (e.g., drug delivery means) or can be secreted by supporting cells to achieve the desired concentration, for example, at a specified time after encapsulation or implantation.

Without being bound in theory, it is also contemplated that sufficiently highly functioning parenchymal cells can be encapsulated without nonparenchymal cells, for example, if stabilized or pre-stabilized with appropriate biochemical cues.

In certain embodiments of the above methods, the construct remains viable for at least three, four, six, eight or twelve weeks upon in vivo implantation.

In certain embodiments of the above methods, one or more of the populations of cell are engineered to express a reporter protein.

Implantation of Engineered Tissue Seeds for Expansion

Current methods for engineering liver tissue and studying human liver functions in vivo are limited to insufficient. In one approach, transgenic mice are genetically engineered to express a single human gene of interest (i.e. a particular CYP3A or 2B isoenzyme, which participates with its isoenzymes in metabolizing approximately 65-80% of clinical drugs; or a human nuclear receptor such as hPXR or SXR, transcription factors which regulate CYPs) (See e.g., Xie and Evans (2002) Drug Discov. Today 7(9): p. 509-15.). However, the utility of these transgenic mice models have been limited to studying drug response profiles and transcriptional regulation of only single drug-metabolizing genes.

Azuma et. al. generated a liver-injury model (Fah−/−/Rag2−/−/Il2rg−/− mice) whereby immune-deficient mice lacking the fumarylacetoacetate hydrolase (Fah) gene develop liver disease upon removal of a protective drug (Azuma et al. (2007) Nat. Biotechnol. 25, 903-910). This mouse model provides a more flexible window of time in which to introduce human hepatocytes and was demonstrated to enable expansion human hepatocytes in vivo over several passages. Yet animals still required pretreatment with a urokinase-expressing adenovirus for human hepatocytes to efficiently engraft and repopulate the mouse liver and only 16.3% of mice injected were highly repopulated with 30-90% human hepatocytes. Despite very recent technical advances improving the repopulation efficiency of the Fah−/− model (Bissig et al. (2007) PNAS 104, 20507-20511; and Bissig et al. (2010) J. Clin. Invest. 120, 924-930), both liver-injury models demand several weeks to several months establishment time, and are inherently variable in their degree of humanization. Through the studies, described herein, in particular in the working examples presented infra, survival and liver-specific functions of engineered human liver tissue seeds has been demonstrated using a platform that supports liver functions in vivo. This disclosure will aid researchers in both academia and pharmaceutical industries in the study of human liver biology in vivo.

Regeneration Cues

Engineered tissue seeds were unexpectedly found to expand in vivo when in the presence of an injury. Specifically, engineered tissue seeds containing hepatocyte aggregates and endothelial cords expanded when implanted ectopically into a mouse where liver injury was induced. There was no expansion of the engineered tissue seed in an uninjured mouse.

The liver is capable of regenerating upon injury. In certain embodiments, liver injury is induced by an injury to the host. In certain embodiments, the injury is surgery. In certain embodiments, liver injury is induced by a chemical. In certain embodiments, the liver injury occurs from a disease or infection. In certain embodiments, the liver injury is a result of cirrhosis or cancer. In certain embodiments, the liver injury is a result of a viral infection, for example, hepatitis C (HCV).

Liver injury can induce the secretion of regeneration cues. In certain embodiments, regeneration cues secreted by an injured liver induce the expansion of the engineered tissue seed. In certain embodiments, the engineered tissue seed does not expand without injury to the liver. Liver injury increases the activity of urokinase, which then activates plasminogen into plasmin, which activates metalloproteinases. Urokinase is likely to trigger remodeling of the ECM. In certain embodiments, the injured liver secretes hepatocyte growth factor (HGF) or epidermal growth factor (EGF).

One way to assess liver regeneration is to measure biomarkers in the blood. In certain embodiments, the engineered tissue seed is implanted into a subject and expands into a functional engineered liver tissue. Expansion of the engineered tissue seed can be evaluated by measuring biomarkers. Non-limiting examples of biomarkers that indicate liver regeneration and therefore expansion of the engineered tissue seed are serum albumin, alpha-1-antitrypsin, transferring, and factor IX for hemophilia.

In some embodiments, the engineered tissue seed implanted into a subject and exposed to regeneration cues expresses and/or induces human drug-metabolizing enzymes and other key liver-specific genes (e.g., transcription factors). In some embodiments, expanded engineered tissue seeds exposed to regeneration cues express more liver-specific genes compared to unexpanded endothelial and fibroblast cells. In some embodiments, the expanded engineered tissue seeds exposed to regeneration cues express Phase I cytochrome P450 enzymes. In some embodiments, the expanded engineered tissue seeds exposed to regeneration cues express CYP3A4 and/or CYP2B6. In some embodiments, the expanded engineered tissue seeds exposed to regeneration cues express Phase II enzymes. In some embodiments, the expanded engineered tissue seeds exposed to regeneration cues express sulfotransferase. In some embodiments, the expanded engineered tissue seeds exposed to regeneration cues express Phase III anion transporters. In some embodiments, the expanded engineered tissue seeds exposed to regeneration cues express SLCO1A2/1B1. In some embodiments, the expanded engineered tissue seeds exposed to regeneration cues express ATP-binding transporters. In some embodiments, the expanded engineered tissue seeds exposed to regeneration cues express ABCB/ABCG.

In some embodiments, regeneration cues induce the expression of human cytokeratin-18 (Ck-18), an intermediate filament expressed by hepatocytes, and arginase-1 (Arg-1), an enzyme that catalyzes the hydrolysis of arginine to ornithine and urea, in hepatocytes present in the engineered tissue seeds. In some embodiments, regeneration cues induce Ck-18-positive graft area of engineered tissue seeds post-implantation. In some embodiments, regeneration cues induce Ck-18 and Ki67 double-positive cells. In some embodiments, regeneration cues induce proliferation of the cells in the engineered tissue seed post-implantation.

Engineered tissue seeds implanted in animals with liver injury, and thereby exposed to regeneration cues, exhibit several microstructural hallmarks typically associated with human liver. For example, in some embodiments, engineered tissue seeds contain duct-like structures resembling bile ducts. Cytokeratin-19 and cytokeratin-7 are both expressed in biliary epithelial cells but not hepatocytes. In some embodiments, the ductal structures contain both Ck-18 and Ck-19 double-positive cells, indicating the cells exhibit biliary epithelial-like characteristics. In some embodiments, the ductal structures contain Ck-18 and Ck-7 positive cells. In some embodiments, the Ck-18 and Ck-19 double-positive ductal structures are located within connective tissue and adjacent to human CD31-positive blood vessels. In some embodiments, the blood vessels contain Ter-119 positive erythroid cells.

In some embodiments, the engineered tissue seeds implanted in a subject contain red blood cells. In some embodiments, regeneration cues promote expansion of the blood pool in engineered tissue seeds implanted in a subject. In some embodiments, regeneration cues promote the formation of vessels in an engineered tissue implanted in a subject. In some embodiments, the vessels in an engineered tissue seed contain Ter-119 positive erythroid cells and human CD31-positive endothelial cells.

Applications for Engineered Tissue Seeds

In certain embodiments, the engineered tissue seeds described herein can be implanted in a subject. Non-limiting examples of non-human subjects include non-human primates, dogs, cats, mice, rats, guinea pigs, rabbits, fowl, pigs, horses, cows, goats, sheep, etc. In certain embodiments, the subject can be any animal. In certain embodiments, the subject can be any mammal. In certain embodiments, the subject can be a human. For example, in certain embodiments, the engineered tissue seeds described herein can be implanted in a subject by suturing the engineered tissue seeds to fat pads in the lower abdomen.

In certain embodiments, the engineered tissue seeds described herein can be used to enhance the survival, function, and expansion of hepatocytes upon implantation. Effective mass transport between the blood stream and the liver for metabolic needs relies on a precisely-defined microenvironment delineated by the paracrine signaling between hepatocytes and endothelial cells. As such, the liver serves as an ideal model to study the interaction between organized endothelial networks and cellular function.

EXAMPLES

Materials and Methods
Cell Culture

Primary cryopreserved human hepatocytes (Lot NON, 35 year old, Caucasian, Female, Celsis or Lot Hu8085; 1 year old, female, Caucasian, Invitrogen) were maintained in high-glucose DMEM (Cellgro) containing 10% (vol/vol) FBS (Gibco), 1% (vol/vol) ITS supplement (insulin, transferrin, sodium selenite; BD Biosciences), 0.49 pg/mL glucagon, 0.08 ng/mL dexamethasone, 0.018 M Hepes, and 1% (vol/vol) penicillin-streptomycin (pen-strep; Invitrogen). Primary human umbilical endothelial cells (HUVECs; Lonza; passages 4-7) were maintained in dishes in EGM-2 media (Lonza). Normal human dermal fibroblasts (NHDFs; Lonza; passages 4-8) were cultured in DMEM with 10% (vol/vol) FBS and 1% (vol/vol) pen-strep. J2-3T3 fibroblasts were maintained in high-glucose DMEM containing 10% (vol/vol) bovine serum and 1% (wt/vol) pen-strep.

Fabrication of Micropatterned 'Tissue Seeds'

Engineered liver 'tissue seeds' containing J2 cells were fabricated as described previously (Baranski et al., PNAS (2013), Vol. 110: 11842-11847), or with NHDFs with exceptions as outlined herein. To create hepatic aggregates, human primary hepatocytes were thawed and immediately plated into AggreWell micromolds along with NHDFs or J2 cells and incubated overnight. To create endothelial cords, 3 million HUVECs were suspended in 2.5 mg/mL liquid collagen (BD Biosciences) and centrifuged into polydimethylsiloxane (PDMS) channels. Collagen was polymerized, and constructs were incubated in EGM-2 media for 4 hours to allow for cord formation. Endothelial cord arrays were then embedded in 10 mg/mL fibrin (human thrombin, Sigma; bovine fibrinogen, Sigma). Hepatic aggregates (approximately 100 hepatocytes and 200 fibroblasts per aggregate) were suspended in 10 mg/mL fibrin at a concentration of 90,000 aggregates/mL fibrin and added in a second layer over endothelial cords in order to fully encase the cords in hepatic aggregates and fibrin gel. Synthetic tissues were cut with a 6 mm biopsy punch immediately prior to implantation. Each tissue contained approximately 150,000 human hepatocytes, 300,000 fibroblasts, and 150,000 HUVECs upon implantation.

Implantation and Induction of Liver Injury

All surgical procedures were conducted according to protocols approved by The Rockefeller University and Massachusetts Institute of Technology Institutional Animal Care and Use Committees. Eight- to twelve-week-old female NCR nude (Taconic; for uninjured mouse studies in FIG. 1) or FAH(−/−) backcrossed to NOD, Rag1(−/−), and Il2rγ (null) (FNRG) mice (Azuma, H. et al., Nature Biotech (2007), Vol 25: 903-910; Wilson E. M. et al., Stem Cell Research (2014), Vol. 13: 404-412; de Jong, Y. P., et al., Sci Transl Med (2014), Vol. 6:254ra129) were anesthetized using isoflurane, and the synthetic tissue constructs were sutured to the mesenteric parametrial fat pad (1 tissue per animal for nude mouse studies; 4 tissues per animal for FNRG studies). The incisions were closed aseptically, and the animals were administered 0.1 mg/mL buprenorphine every 12 hours for 3 days following surgery. NTBC was withdrawn from animals' drinking water immediately following synthetic tissue implantation and for 14 days following implantation. NTBC was then administered for four days and then cycled off/on in 14 days-off and 3-4 days-on increments for the remainder of the experiment. For hepactteomy studies, partial hepatectomy liver injury was performed one week following implantation of seeds. Prior to hepatectomy surgery, mice were administered 5 mg/kg carprofen subcutaneously. Partial hepatectomy was then performed as described previously (Mitchell, C., & Willenbring, H., Nat Protoc. Vol. 3: 1167-1170, 2008) with slight modifications. Specifically, the left lateral and left median lobes were excised, sparing the gall bladder. The abdomen was washed with saline prior to closing the peritoneum with vicryl sutures. Following hepatectomy, animals were injected with 50 mg/kg Edu (5-ethynl-2'doexyuridine; ThermoFisher Scientific) daily until sacrifice at seven days following hepatectomy.

Bioluminescence Imaging

To enable noninvasive imaging of the survival of functional hepatocytes, primary human hepatocytes were transduced in suspension culture immediately upon thawing with a lentiviral vector expressing firefly luciferase under the human albumin promoter ((pTRIP.Alb.IVSb.IRES.tagRFP-DEST, gift of Charles Rice, The Rockefeller University) before SEEDS fabrication. For viral transduction, concentrated virus was diluted 1:5 into hepatocyte media containing HEPES buffer (20 mM; Invitrogen) and polybrene (4 μg ml$^{-1}$, Invitrogen) in six-well ultra-low-attachment plates (Corning). Immediately before bioluminescence imaging, mice were injected intraperitoneally with 250 μl of 15 mg ml$^{-1}$ D-Luciferin (Caliper Life Sciences) and imaged using the IVIS Spectrum (Xenogen) system and Living Image software (Caliper Life Sciences).

Biochemical Assays

Throughout the experiment, mice were bled retro-orbitally, blood was collected, and serum was separated by centrifugation. Serum levels of human albumin were determined by an enzyme-linked immunosorbent assay (ELISA)

using goat polyclonal capture and HRP-conjugated goat anti-human albumin detection antibodies (Bethyl laboratories). At the time of sacrifice for some animals, blood was retrieved via cardiac puncture and collected in clot-activating tubes. Serum levels of human albumin (Bethyl), human alpha-1-antitrypsin (Bethyl), and human fibronectin (Boster) were determined by ELISA.

Tissue Harvesting and Immunohistochemistry

Animals were sacrificed at the termination of the experiment (80-84 days). Tissue was harvested from the intraperitoneal space, and explants were fixed in 4% (vol/vol) paraformaldehyde (PFA) for 48 hours at 4° C. Explants were sectioned into approximately 1 mm sections by hand and then dehydrated in graded ethanol (50-100%), embedded in paraffin, and sectioned using a microtome (6 μm) for immunohistochemical staining. All morphometric analyses (e.g., graft size) were performed on stained 6 μm sections from the surface of all 1 mm sections of each graft.

For gross visualization of tissue, sections were stained with hematoxylin and eosin (H&E). For visualization of type III collagen, sections were stained with reticulin/nuclear fast red stain (Dako).

For identification of primary human hepatocytes, sections were incubated with primary antibodies against human Ck-18 (mouse, 1:25; Dako) or arginase 1 (rabbit, Arg-1, 1:400; Sigma) and followed with species-appropriate secondary antibodies conjugated to Alexa 647. To determine graft size, Adobe Photoshop was used to quantify number of Ck-18 positive pixels in each graft. For identification of primary human hepatocytes in active cell cycle phases, sections were blocked using M.O.M. Blocking Reagent and normal donkey serum, then incubated with primary antibodies against human Ck-18 (mouse, 1:25; Dako) and Ki67 (rabbit, 1:500; Abcam) and followed with species-appropriate secondary antibodies conjugated to Alexa 555 and 647.

For identification of primary human hepatocytes and human bile canaliculi, sections were blocked using M.O.M. Blocking Reagent (Vector Laboratories) and normal donkey serum, then incubated with primary antibodies against human Ck-18 and human MRP2 (rabbit, 1:100; Abcam) and followed with species-appropriate secondary antibodies conjugated to Alexa 555 and 647. For identification of primary hepatocytes, human endothelial cells and mouse red blood cells, sections first were blocked using M.O.M. Blocking Reagent and normal donkey serum and then immunostained using primary antibodies against human arginase 1 (rabbit, Arg-1, 1:400; Sigma), human CD31 (mouse, 1:20; Dako), and Ter-119 (rat, 1:100; BD Pharmingen), respectively. Signal was visualized after incubation with secondary goat anti-IgG1-Alexa 555, donkey anti-rat-Alexa 488, and donkey anti-rabbit-Alexa 647 antibodies (Jackson ImmunoResearch). For identification of primary human hepatocytes and biliary cells, sections were blocked using M.O.M. Block Reagent and normal donkey serum, then immunostained with primary antibodies against human Ck-18 and Ck-19 (rabbit, 1:250; Abcam) or human CK7 (rabbit, 1:300; Novus) and followed with species-appropriate secondary antibodies conjugated to Alexa 555 and 647. Positive control human adult liver sections were purchased from Abcam. Images were obtained using a Nikon Eclipse Ti microscope, Nikon 1AR Ultra-Fast Spectral Scanning confocal microscope, or Zeiss AxioCam HRm Stereoscope.

For SWITCH tissue clarification, 1 mm thick sections of explanted expanded seed grafts were treated with glutaraldehyde and then cleared with 200 mM SDS using methods developed previously (Murray, E. et al., Cell, Vol. 163: 1500-1514, 2015). To visualize mouse versus human vessels, cleared SEED graft sections were incubated in a solution of 500 ug/ml lectin from *Helix pomatia* agglutinin (PHA) conjugated to Alexa 488 (Sigma-Aldrich) and 100 ug/ml lectin from *Ulex europaeus* agglutinin (UEA-1) conjugated to TRITC (Vector laboratories) in PBS, which have been shown previously to bind to mouse or human endothelial cells, respectively (Baranski, J. D., et al, *Proc Natl Acad Sci USA*., Vol. 110: 7586-7591, 2013). Images were obtained using an Olympus 10× CLARITY immersion medium 0.6 NA objective.

RNA-Seq and Bioinformatics

Total RNA was extracted from explanted seed grafts (n=3), primary cryopreserved human hepatocytes (immediately after thawing; n=2), human liver (n=1), HUVECs (n=1) and NHDFs (n=1_using Qiagen RNeasy Mini Kits. RNA was passed through initial quality control using an Agilent BioAnalyzer, poly-A purified and converted to cDNA using the Illumina Tru-Seq protocol, run on SPRIworks system (Beckman Coulter) using custom barcodes for library preparation, enriched by PCR, and submitted for Illumina sequencing. 40 nucleotide paired-end sequencing was then performed on an Illumina HiSeq 2000. A standard pipeline was used for quality control of HiSeq outputs, consisting of gathering fastqc and tag count statistics at the flowcell level, as well as individual fastqc on each sample.

The fastq files for each sample were aligned to both human reference genome hg19 using STAR (Dobin, A. et al., *Bioinformatics*, Vol. 29: 15-21, 2013). HTSeq (Anders, S., et al., *Bioinformatics*, Vol. 31: 166-169, 2015) was used to obtain transcript counts from the SAM outputs of the STAR alignment, using Ensembl gene annotations. The counts data was normalized for read depth and analyzed using the DESeq2 package in R, clustering was performed using the heatmap package, and plots were produced in R and Graphpad Prism. Healthy adult human liver control RNA was obtained commercially (LifeTech and CloneTech).

Statistical Analysis

All data are expressed as the mean±SEM. Statistical significance ($p<0.05$) was determined using a Students T-test or One-way ANOVA followed by Tukey's post hoc test.

Example 1

Generation of Engineered Tissue Seed

To determine the ability of an engineered tissue to expand in vivo in response to regenerative cues, a minimal engineered tissue seed composed of human hepatocytes, endothelial cells, and stromal cells was generated. Microwell technology was used to create aggregates composed of human hepatocytes and normal human dermal fibroblasts (NHDFs; FIG. 1A). Similarly, microtissue molding was used to create patterned endothelial cords from human umbilical vein endothelial cells (FIG. 1B). Hepatic cellular aggregates and endothelial cords were encapsulated in a fibrin hydrogel to create 'tissue seeds' which were implanted ectopically in the intraperitoneal mesenteric fat of mice (FIG. 1B). J2 cells, a mouse fibroblast cell line, were used initially to study the ability of tissue seeds to expand in vivo.

Figure 2A:
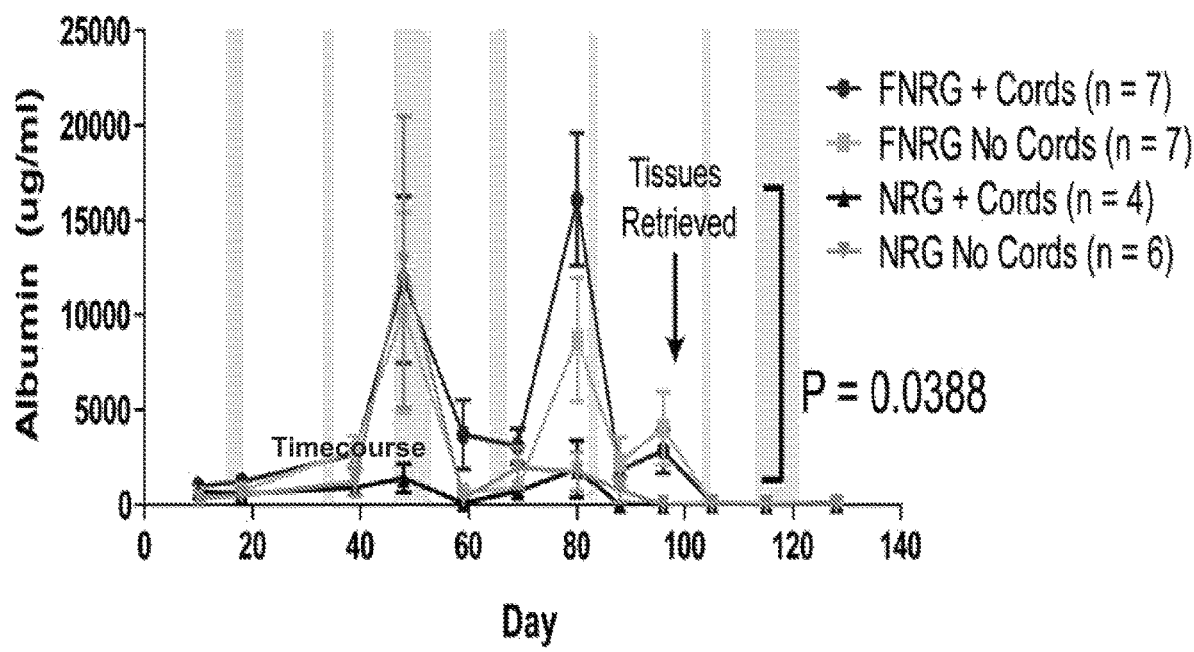
FIG. 2A is a line graph depicting human albumin production (µg/ml) over a time period of 130 days after implantation of engineered tissue seeds containing J2 mouse fibroblast cells, with or without cords. Engineered tissue seeds were implanted in NRG mice (Nod-Rag1$^{null}$ IL2rg$^{null}$, Nod rag gamma) or FNRG mice (NRG mice with fumaryl acetoacetate hydrolase knockout). Gray bars indicate where NBTC, a chemical that prevents liver injury in FNRG mice, was fed to mice.
Figure 2B:
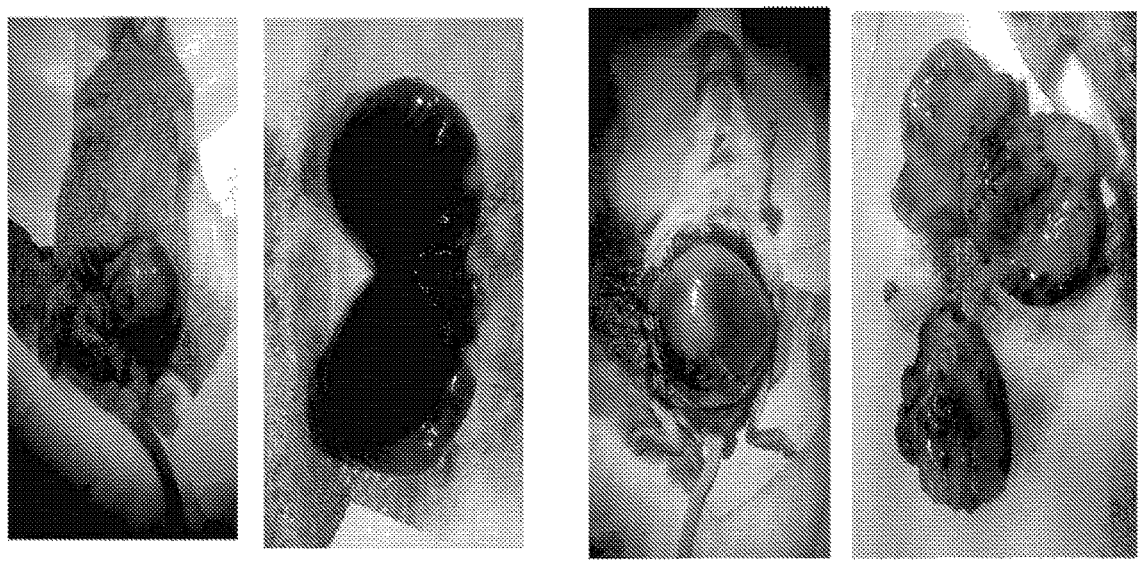
FIG. 2B shows pictures of tumors formed by the engineered tissue seeds containing J2 mouse fibroblast cells when implanted into mice.
Figure 3A:
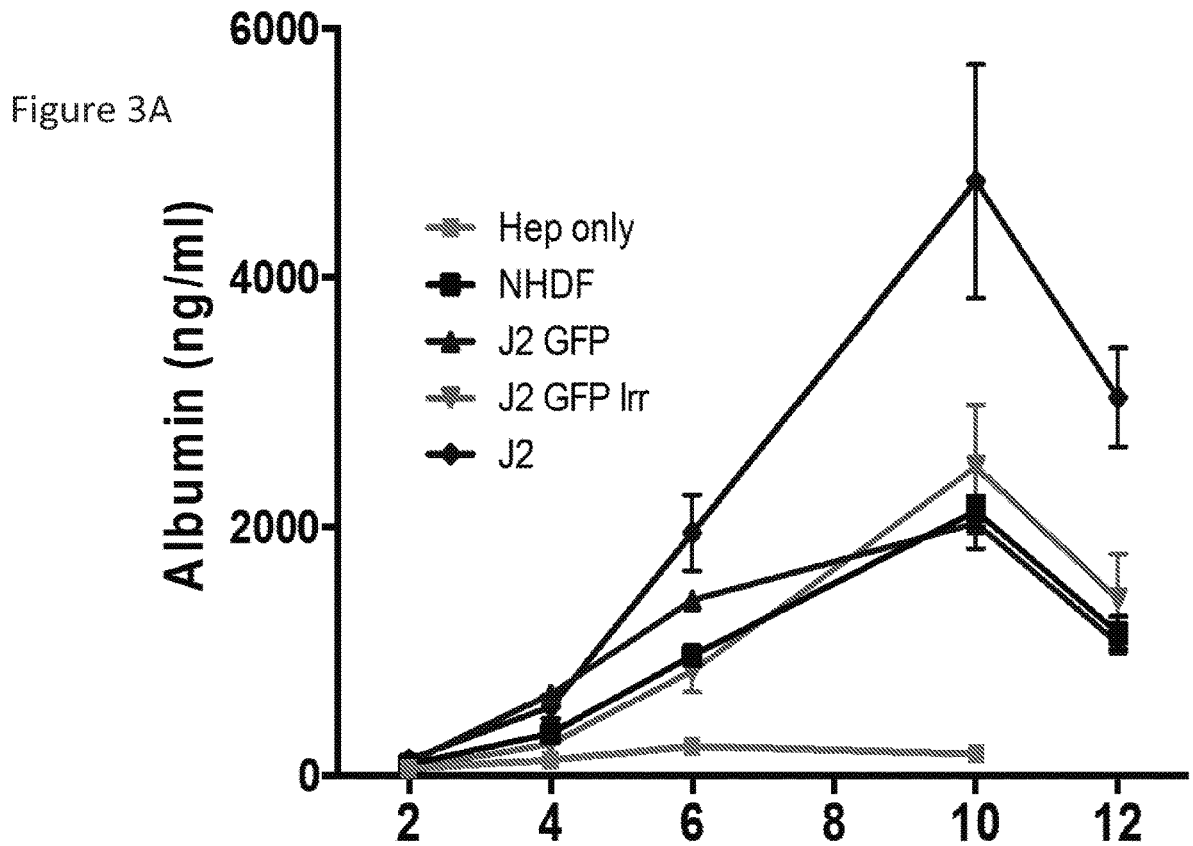
FIG. 3A is a line graph depicting human albumin production (ng/ml) over a time period of 12 days, in mice with implanted engineered tissue seeds without endothelial cords. The seeds contained either hepatocytes only ("Hep"), normal human dermal fibroblasts ("NHDF"), J2 mouse fibroblasts marked with green fluorescent protein (GFP) ("J2 GFP"), irradiated J2 mouse fibroblasts marked with GFP ("J2 GFP Irr"), or normal J2 mouse fibroblast cells.
Figure 3B:
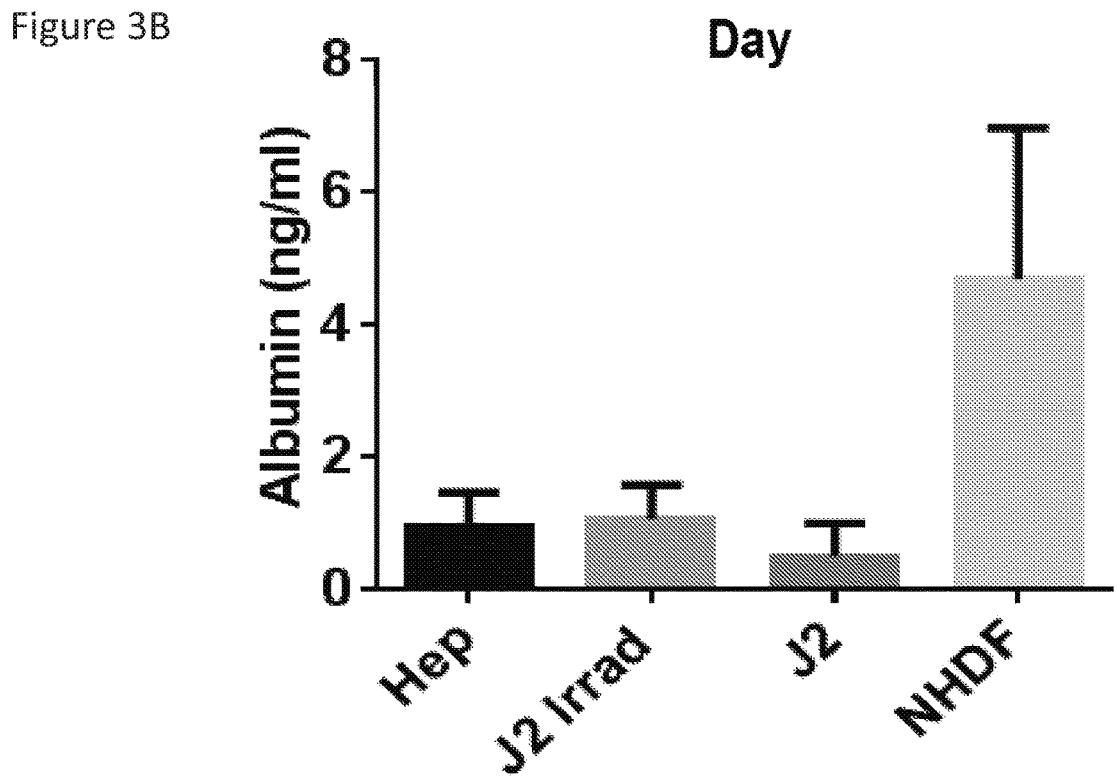
FIG. 3B is a bar graph depicting albumin production (ng/ml) in mice with implanted engineered tissue seeds with endothelial cords, around 14 days after implantation.

Previously developed constructs (Baranski et al., *PNAS* (2013), Vol. 110: 11842-11847) contained human hepatocytes and mouse fibroblast cells (J2) to generate hepatocyte aggregates. The engineered tissue seeds, with or without endothelial cords, were implanted in both NRG mice (no liver injury) and FNRG mice (liver injury) and albumin production was measured for around 130 days. FIG. 2A shows that albumin production increased in the FNRG mice that had tissue seeds containing endothelial cords compared to mice implanted with tissue seeds without endothelial cords. However, upon histology and analysis of the gross appearance, the engineered tissue seeds were found to form fibrous tumors (FIG. 2B). To prevent tumor formation, engineered tissue seeds were generated with irradiated J2 cells to slow growth of the cells, or with NHDFs. J2 cells were also marked with GFP to track the cells in the graft, and thereby analyze the tumors to determine if the tumors grew from J2 cells. These engineered tissue seeds did not contain endothelial cords. As shown in FIG. 3A, albumin production was greatest in mice containing engineered tissue seeds comprising J2 cells. However, irradiated J2 cells and NHDFs also produced significant levels of albumin compared to engineered tissue seeds comprising hepatocytes only. When endothelial cords were added to the engineered tissue seed and implanted into the mouse, unexpectedly, albumin production was highest with the seed containing NHDFs (FIG. 3B). These results indicated that NHDFs support hepatocytes and therefore may be an adequate replacement for J2 cells in the engineered tissue seed.

Figure 4A:
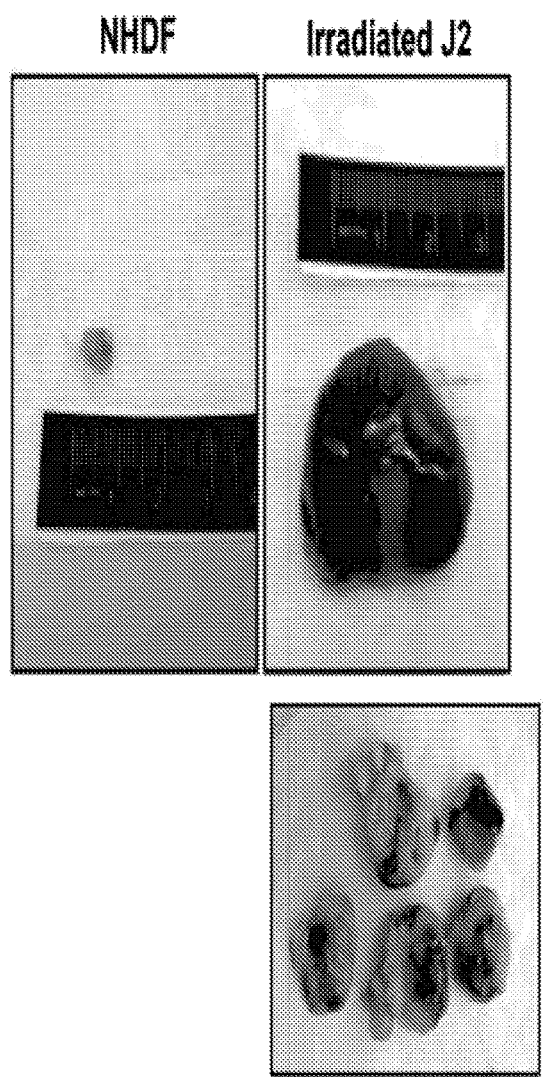
FIG. 4A provides pictures of grafts from either NHDF containing (left) or irradiated J2 containing (right) engineered tissue seeds.
Figure 4B:
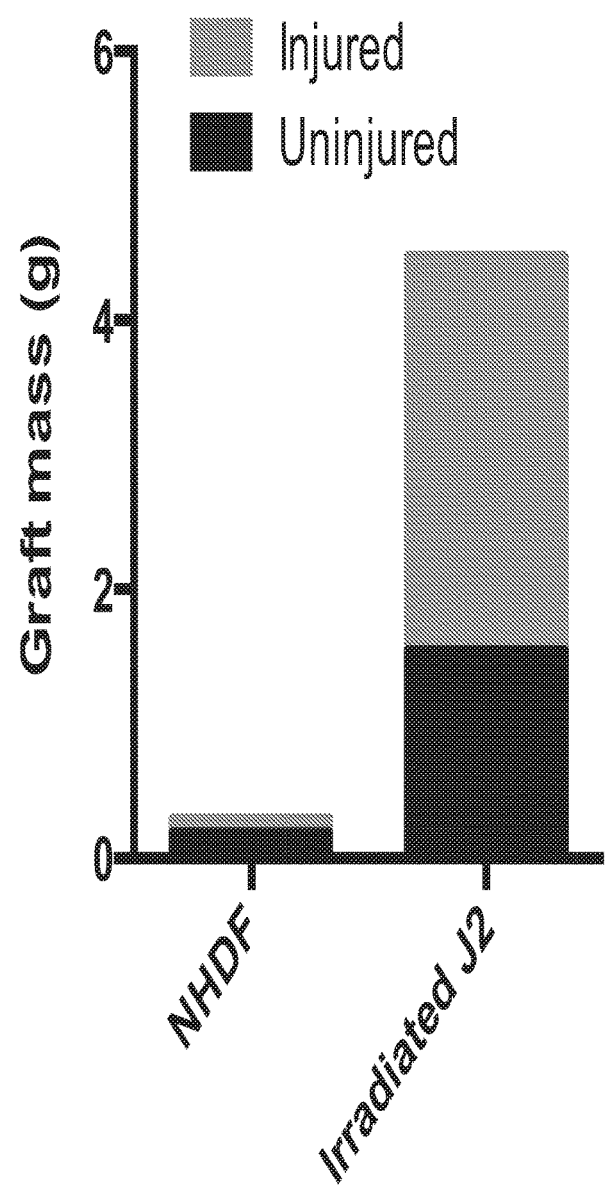
FIG. 4B depicts the weight of grafts (g) from mice implanted with either NHDF containing or irradiated J2 mouse fibroblast cells containing engineered tissue seeds, in both injured and uninjured FNRG mice.
Figure 5:
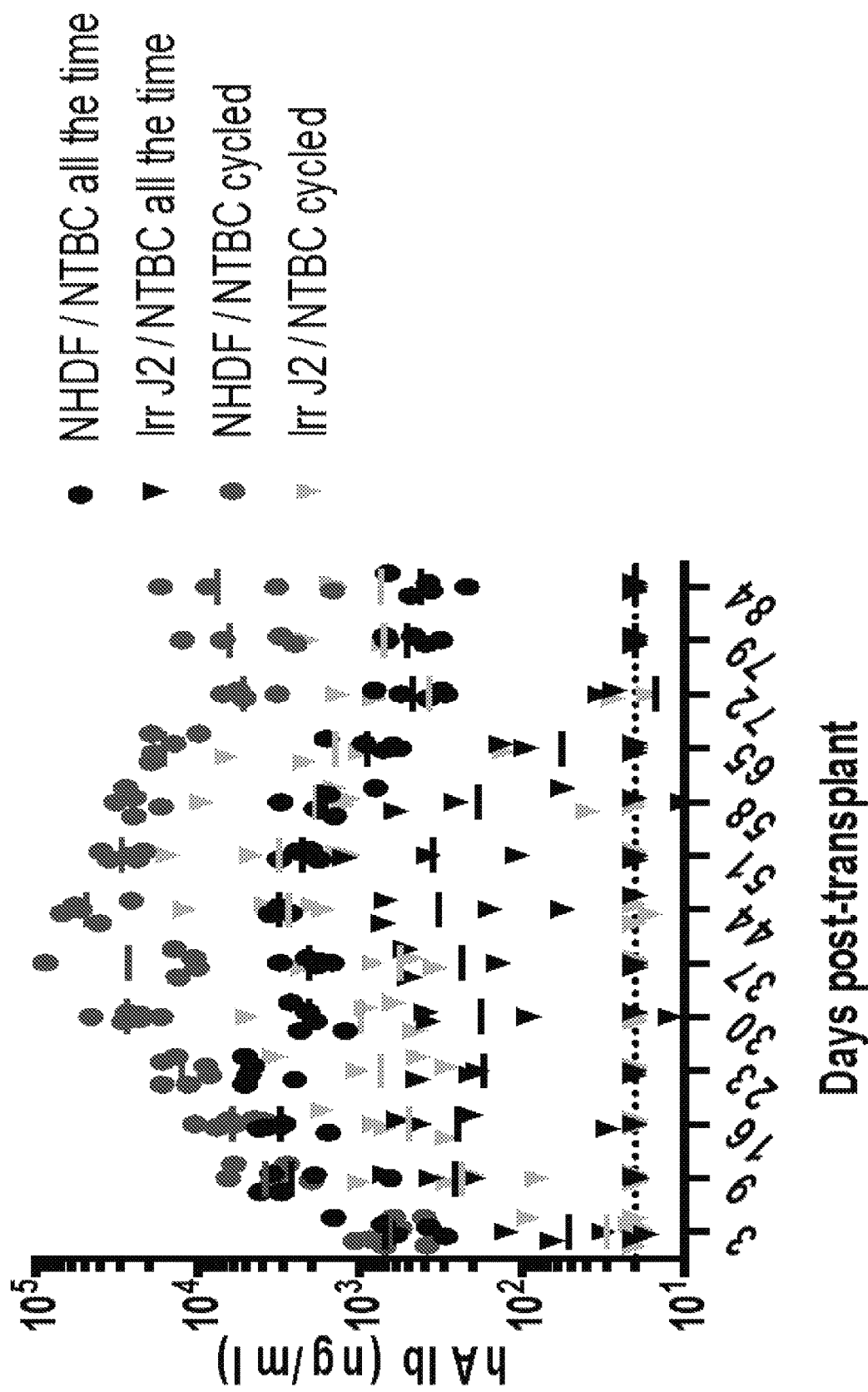
FIG. 5 depicts human albumin production (ng/ml) in mice over a time period of 84 days, in mice with implanted engineered tissue seeds containing either NHDFs or J2 mouse fibroblast cells. Mice either received NTBC continuously (uninjured) or in cycles (injured).

To further analyze the use of NHDFs in place of J2 cells, graft mass was measured in mice implanted with tissue seeds containing either irradiated J2 cells or NHDFs. FIG. 4A shows that tumors did not form from the NHDF containing seeds but still formed in J2 containing seeds. Grafts implanted in mice that had either no liver injury or liver injury as described above, were weighed. Consistent with the macroscopic observations, no tumors formed from the engineered tissue seeds containing NHDFs but did form with irradiated J2 cells (FIG. 4B). To confirm the use of NHDFs in place of J2 cells in the engineered tissue seeds, albumin production was measured over a period of 84 days post-transplantation. Tissue seeds with NHDF cells produced significantly higher levels of albumin in mice with liver injury compared to tissue seeds with J2 cells and compared to uninjured mice (FIG. 5).

Figure 6:
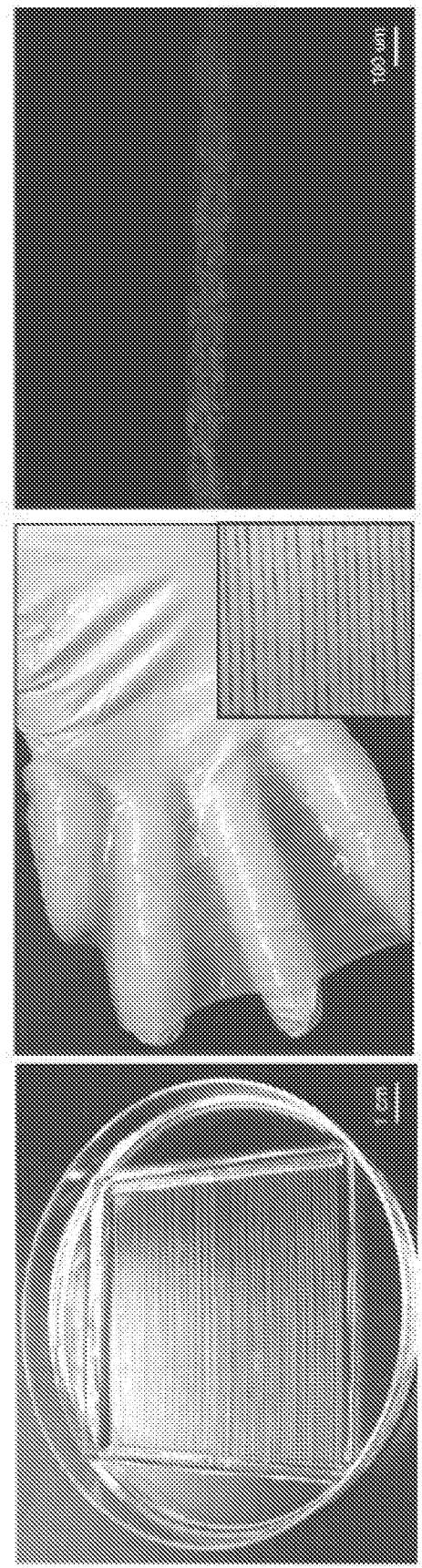
FIG. 6 provides pictures showing scaled construction of larger tissues using bioprinting. The left picture shows sacrificial lattices of carbohydrate glass constructed using bioprinting. The center picture shows a fibrin hydrogel which was embedded in the glass and then dissolved using buffer to leave open channels. The inset of the center picture and the right picture shows the channels filled with endothelial cords.

This fabrication process was adaptable for scaled construction of larger tissues using a bioprinting process previously developed (see Miller, J. S., et al., *Nat Mater* Vol. 11: 768-774, 2012) (FIG. 6).

Figure 7A:
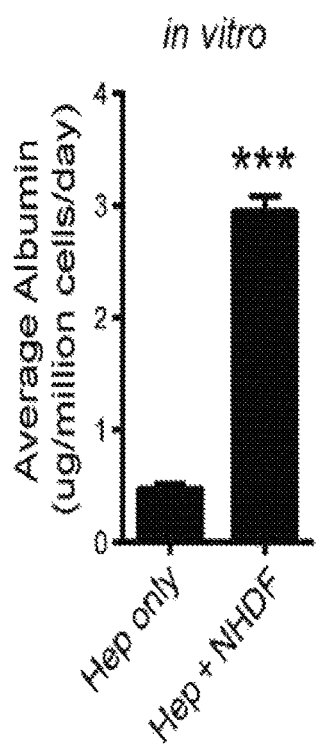
FIG. 7A is a bar graph depicting average albumin production as measured in µg/million cells/day, after engineered tissue seeds were in culture in vitro for six days. Tissue seeds contained either hepatocytes (hep) only or hepatocytes with NHDFs. ***=p<0.0001
Figure 7B:
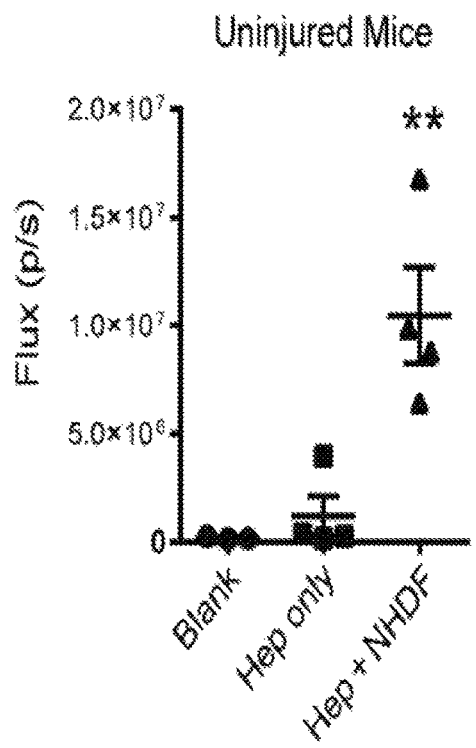
FIG. 7B shows enhancement of albumin promoter activity in uninjured mice upon implantation of engineered tissue seeds containing hepatocytes only or hepatocytes with NHDFs. On the left is a graph depicting photons/second (p/s). On the right is a representative picture of mice implanted with the engineered tissue seeds. ROI=region of interest. **p<0.01
Figure 7B:
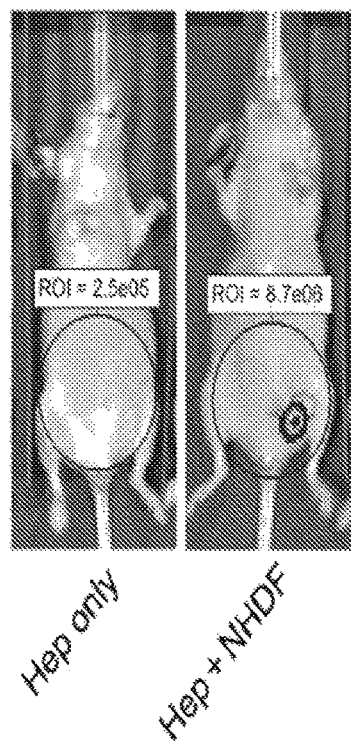
Figure 8A:
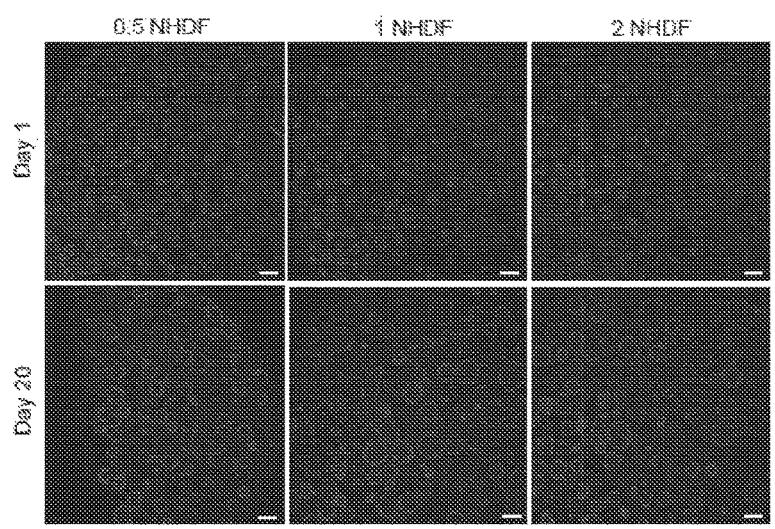
FIGS. 8A and 8B show hepatic aggregates created from primary human hepatocytes and normal human dermal fibroblasts (NHDFs) in varying ratios.
Figure 8B:
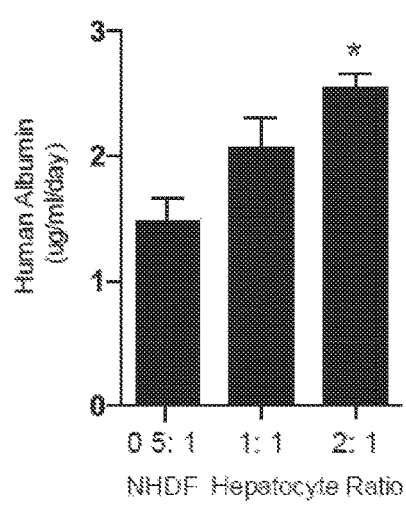

The addition of NHDFs to hepatocyte aggregates enhanced albumin production, a measure of hepatic function, after culture for six days by approximately 6-fold prior to incorporation into tissue seeds in vitro (FIG. 7A). Similarly, upon implantation of tissue seeds in uninjured nude mice, albumin promoter activity was enhanced over 8-fold in animals grafted with tissue seeds containing hepatic aggregates with both NHDFs and hepatocytes compared to hepatocytes without NHDFs (FIG. 7B). Moreover, short-term in vitro tests showed that the addition of NHDFs to hepatocyte aggregates enhances albumin production in a dose-dependent manner (FIGS. 8A and 8B).

Figure 9:
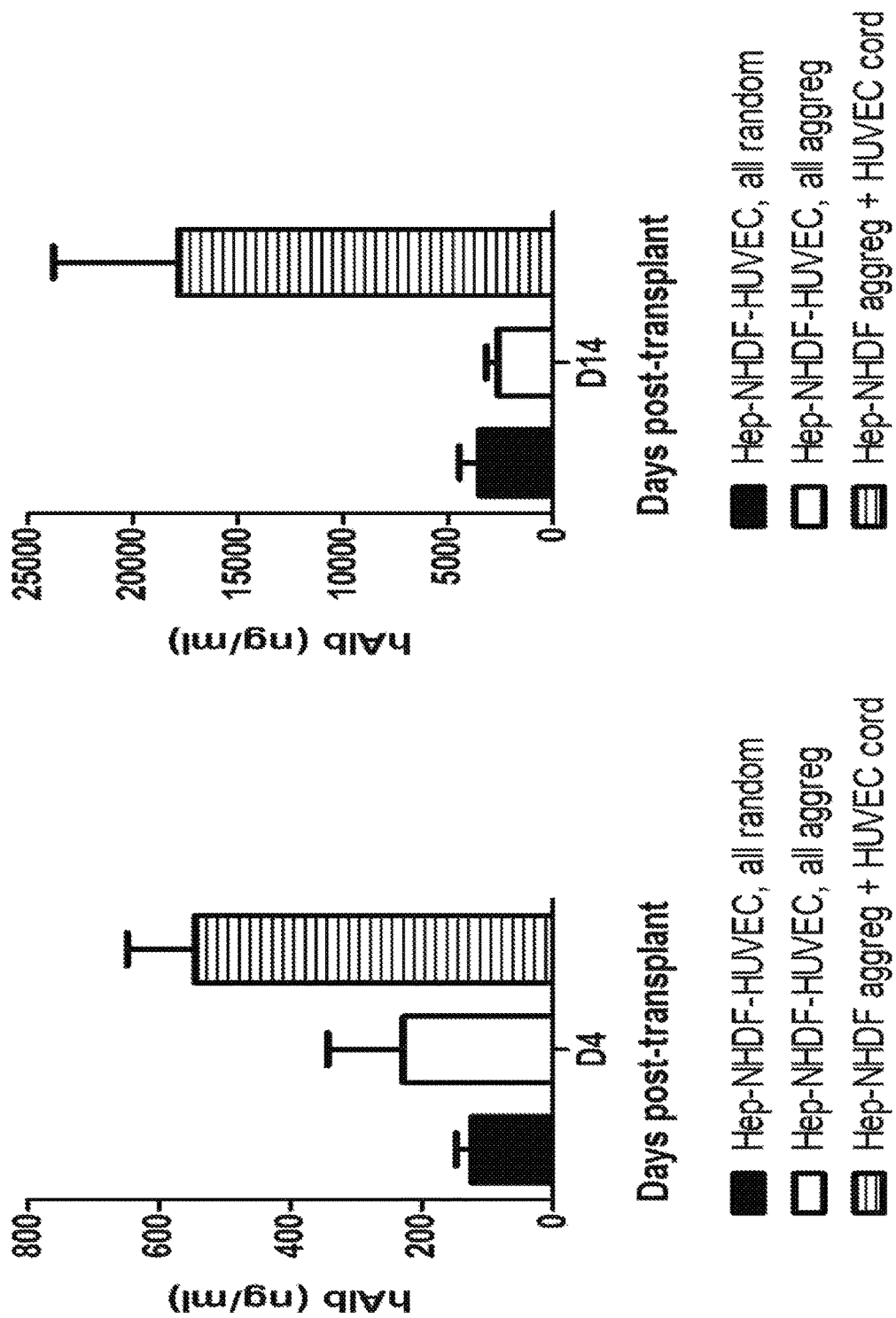
FIG. 9 shows the impact of cell architecture in the engineered tissue seed in human albumin production as measured by ng/ml at 4 (left) and 14 (right) days post-implantation. Three constructs were compared. All contained the same 3 cell populations (human hepatocytes, human fibroblasts and human endothelial cells) in different construct formations (all random, all aggregated, or hepatocyte/fibroblast aggregates and endothelial cords).

The architecture of the tissue seed was also found to be important for generating functional expanded tissue seeds. Tissue seeds with different cell arrangements were generated. FIG. 9 shows that tissues seeds comprising endothelial cords and hepatocyte aggregates (primary human hepatocytes co-cultured with human fibroblasts) ("Hep-NHDF aggreg+HUVEC cord") produced the highest level of human albumin 14 days post-transplant and was secreted earlier, compared to tissue seeds comprising hepatocytes, fibroblasts and endothelial cells randomly organized ("Hep-NHDF-HUVEC, all random"), and tissue seeds comprising hepatocyte, fibroblasts and endothelial aggregates ("Hep-NHDF-HUVEC, all aggreg"). These results show that the architecture of the tissue seed is critical for function of the expanded graft, and that tissue seeds containing endothelial cords and hepatocytes are the most functional.

Thus, these studies resulted in the creation of geometrically patterned human liver tissue seeds containing human hepatocyte aggregates and human endothelial cords.

Example 2

Implantation of Tissue Seed into Host

Figure 10A:
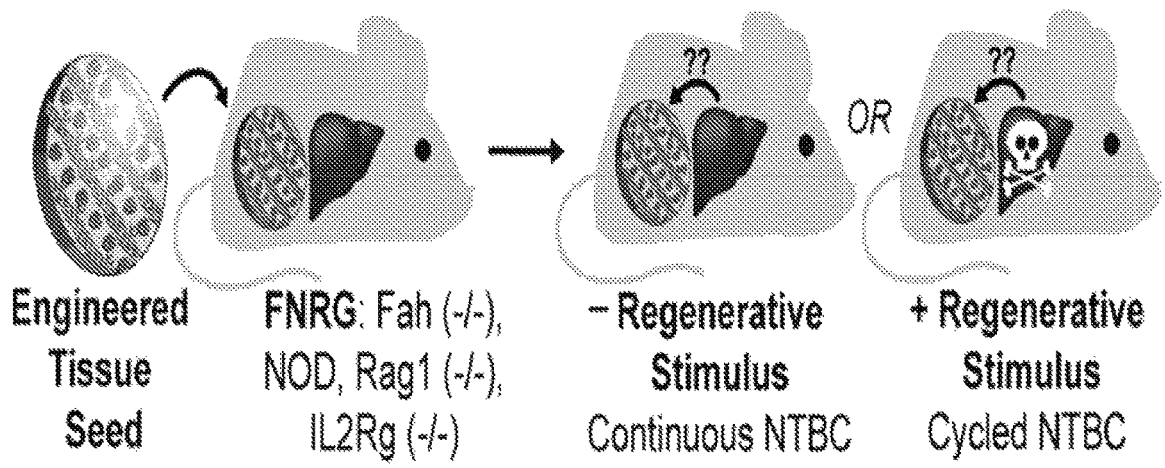
FIG. 10A is a schematic of liver injury. Engineered tissue seeds are implanted onto the mesenteric fat of FNRG mice and then either fed continuous NTBC (control; −regenerative stimulus) or cycled (14 day off/3-4 days on) NTBC (injured; +regenerative stimulus).

To analyze the role of host-derived, soluble regenerative stimuli, fully humanized tissue seeds were implanted onto the mesenteric fat of fumarylacetoacetate hydrolase-deficient (Fah −/−) backcrossed to nonobese diabetic (NOD), recombinase activating gene-deficient (Rag1−/−), interleukin-2 receptor gamma chain-deficient (Il2rγ null) (FNRG) mice, an immune-deficient model of hereditary tyrosinemia type I (Azuma, H., et al., *Nature Biotechnology*, Vol. 25: 903-910, 2007; Wilson, E. M., et al., *Stem Cell Research*, Vol. 13: 404-412, 2014; de Jon, Y. P., et al., *Science Translational Medicine*, Vol. 6: 254ra129, 2014). This mouse strain experiences progressive liver failure unless treated with the small molecule NTBC. NTBC was administered continuously to control animals ('−Regenerative Stimulus' animals; FIG. 10A) or cycled on/off to induce liver damage ('+Regenerative Stimulus' animals) after engraftment. Animals were sacrificed and tissue seed grafts were retrieved at 80 days following tissue implantation. Grafts were readily located in the mesenteric fat pad using the suture as a landmark.

Figure 10B:
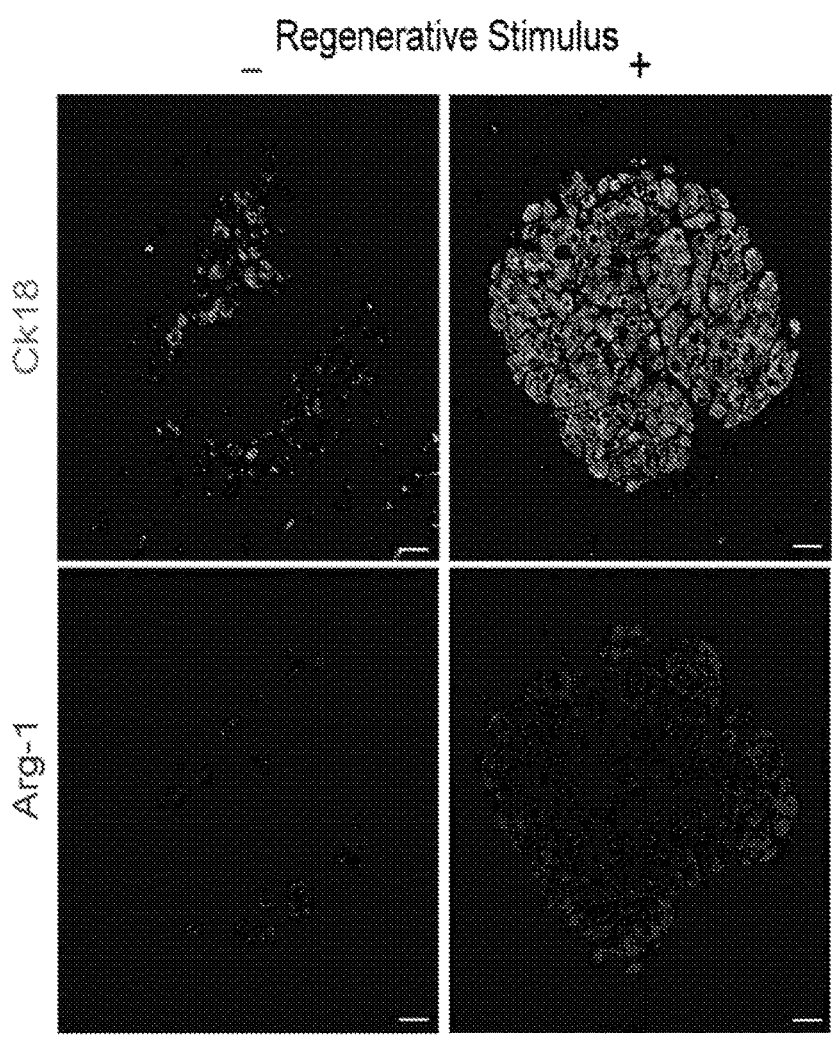
FIG. 10B shows immunostaining of tissue seed grafts retrieved at 80 days post-implantations. Grafts from control mice (−regenerative stimulus) are on the left and grafts from injured mice (+regenerative stimulus) are on the right. Staining detected cells positive for human cytokeratin-18 (Ck18) cells or arginase-1 (Arg-1) cells. Scale bars are 100 µm.
Figure 10C:
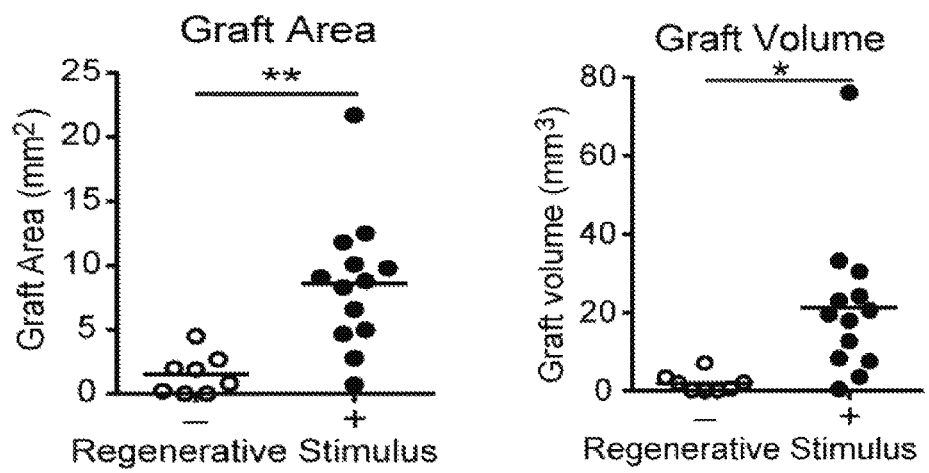
FIG. 10C shows significantly greater Ck-18 positive graft area and volume in animals with regenerative stimuli compared to controls. Tissue seeds were retrieved 80 days post implantation and analyzed. The graph on the left shows graft area measured as mm$^2$. *=p<0.01. The graph on the right shows graft volume as measured by mm$^3$. **=p<0.05.

To determine whether ectopic tissue seeds had expanded in animals with regenerative signals compared to controls, human hepatocytes were identified by immunostaining against human cytokeratin-18 (Ck-18), an intermediate filament expressed by hepatocytes, and arginase-1 (Arg-1), an enzyme that catalyzes the hydrolysis of arginine to ornithine and urea (Yan B. C., et al., *The American Journal of Surgical Pathology* (2010), Vol. 34: 1147-1154; van Eyken, P., et al., *Virchows Archiv. A, Pathological Anatomy and Histopathology* (1987), Vol. 412: 63-72). Grafts from control animals contained small cellular aggregates containing Ck-18 and Arg-1-positive cells dispersed within the hydrogel (FIG. 10B, left). In animals that underwent cycles of injury, visibly larger hepatic grafts were composed of densely packed Ck-18 and Arg-1-positive cells (FIG. 10B, right). Fibrin hydrogel remnants were identified at the periphery of grafts. The Ck-18-positive surface area in tissue seed grafts was quantified by a blinded observer using morphometric analysis in histologic sections. Hepatic tissue seed grafts covered significantly more surface area in animals with regenerative stimuli compared to control animals (FIG. 10C, left, p<0.01). By assuming the grafts to be spherical, graft volume was extrapolated based on surface area measurements and an average 11-fold graft expansion was calculated in animals with regenerative stimuli compared to control animals (FIG. 10C, right, p<0.05). This histomorphometry revealed significantly greater Ck-18-positive graft area and volume in animals with regenerative stimuli compared to controls.

Figure 10D:
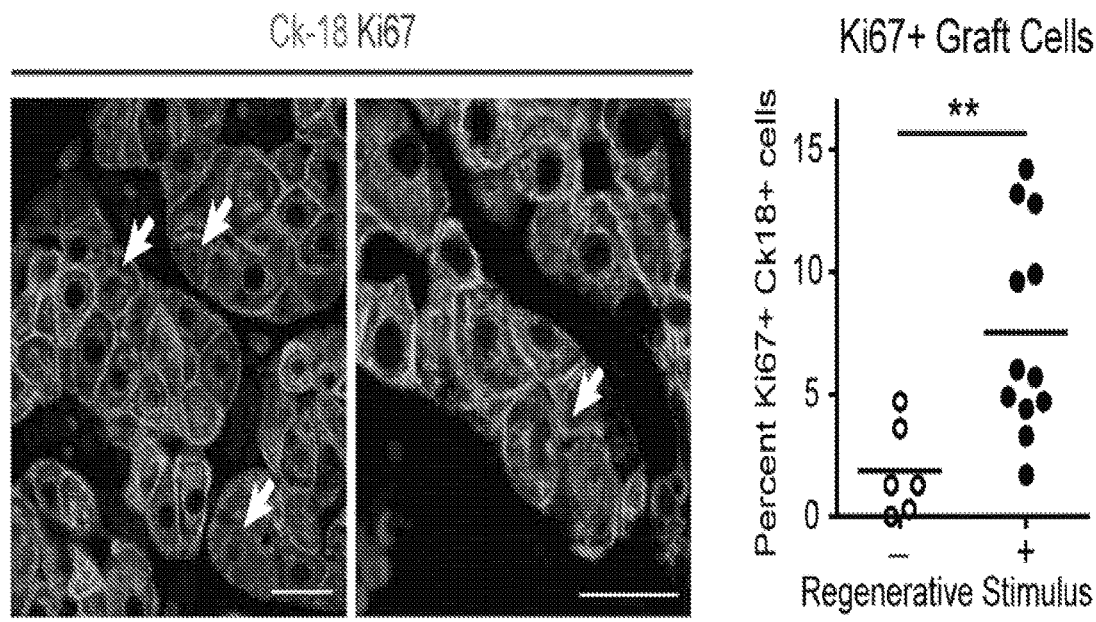
FIG. 10D shows Ki67+Ck-18+ graft cells. The pictures represent immunostaining for both Ck-18 and Ki67 (marker for proliferation). The graph on the right shows percent Ki67+Ck18+ cells in Ki67+ graft cells. **=p<0.01. Scale bars are 10 µm.

To assay for active proliferation in tissue seeds 80 days following implantation, sections were stained with antibodies against Ck-18 and Ki67, a nuclear protein associated with cellular proliferation. Numerous Ck-18 and Ki67 double-positive cells were identified with round nuclei characteristic of hepatocyte nuclei (FIG. 10D, left) as well as rare double-positive cells actively undergoing mitosis (FIG. 10D, center). When compared with control animals, 4-fold more Ck-18 and Ki67 double-positive cells were observed in grafts from animals with regenerative stimuli (FIG. 10D, right, p<0.01). Grafts in animals with regenerative stimuli exhibited a significantly greater number of Ki67 and CK-18 double-positive cells compared to uninjured animals.

Figure 11B:
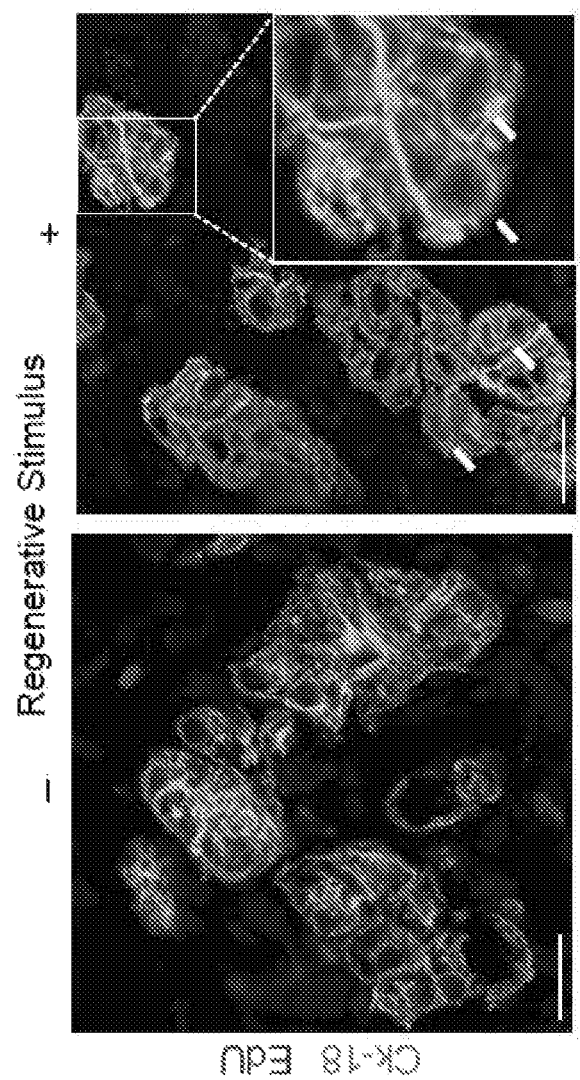
FIGS. 11A and 11B show tissue seeds implanted in the mesenteric fat of athymic mice with regenerative stimulus contained significantly more Ck-18 and EdU double-positive hepatocytes compared to controls (i.e., tissue seeds implanted without regenerative stimulus) after 7 days. Animals were pulsed daily after partial hepatectomy (+regenerative stimulus) with Edu to mark cells in the S-phase of the cell cycle.
Figure 11A:
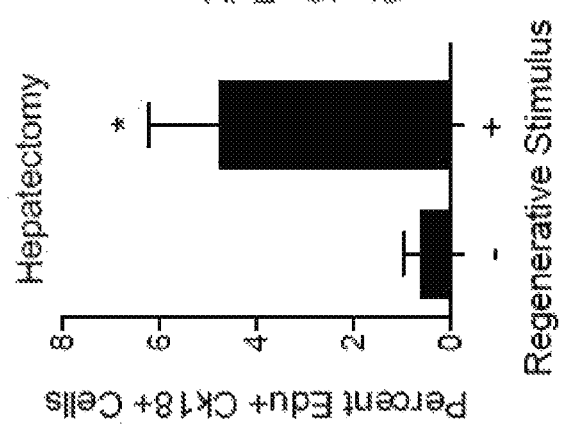

To test whether the tissue seeds also respond to regenerative cues after acute liver injury, tissue grafts were implanted in the mesenteric fat of athymic mice (i.e., nude mice lacking a thymus). After a one week engraftment period, mice were subjected to two-thirds partial hepatectomy of the host liver and pulsed every 12 hours with EdU to label cells in the S phase of the cell cycle. One week after liver injury, animals were sacrificed and engrafted tissues were excised, sectioned and double-immunostained using antibodies that recognize EdU and Ck-18+ to identify hepatocytes in the S-phase of the cell cycle. Grafts subjected to regenerative signals induced by hepatectomy injury contained significantly more EdU and Ck-18 double-positive cells compared to controls (FIGS. 11A and 11B). Taken together, the results demonstrate that in the context of endogenous liver injury, ectopic liver seeds containing primary hepatocytes proliferate to enlarge the graft.

Example 3

Characterization of Expanded Tissue Seeds

Characterization of Human Hepatic Function of Ectopic Grafts

Figure 12A:
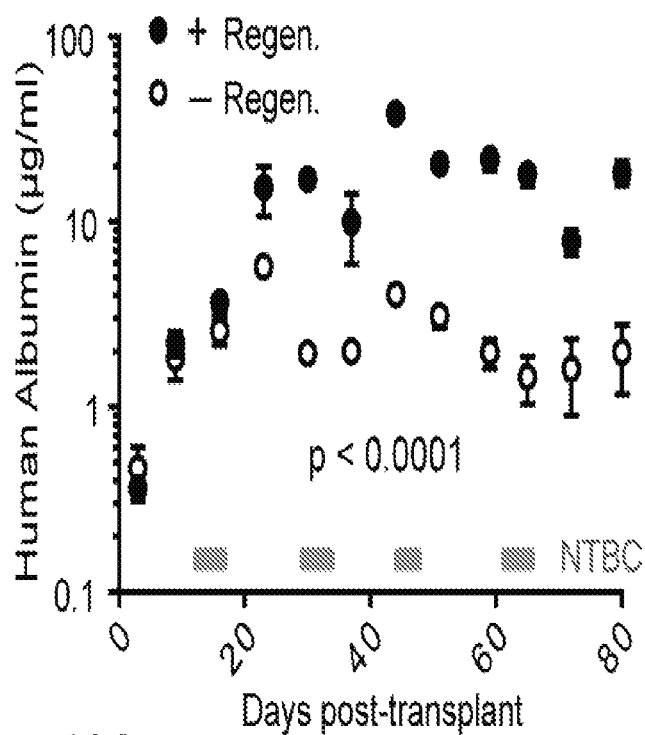
FIG. 12A is a graph depicting human albumin production (ug/ml) over a time period of 80 days post-transplantation. Closed circles represent data from mice with regenerative stimuli and open circles represent data from mice without regenerative stimuli.
Figure 12B:
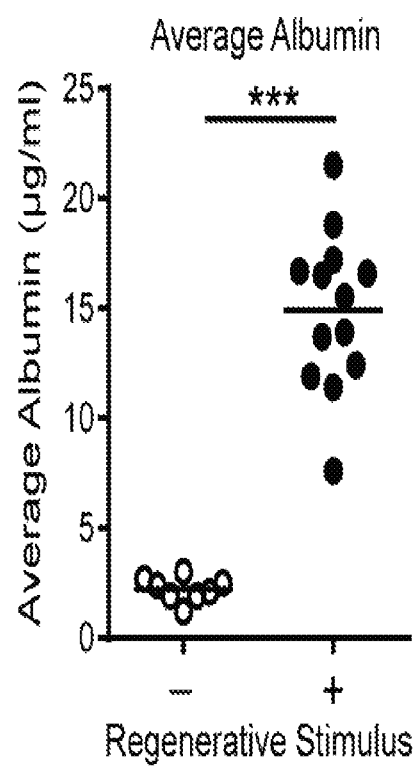
FIG. 12B is a graph depicting the average albumin production 80 days after implantation with engineered tissue seeds, in mice with or without regenerative stimuli. ***=p<0.0001.
Figure 12C:
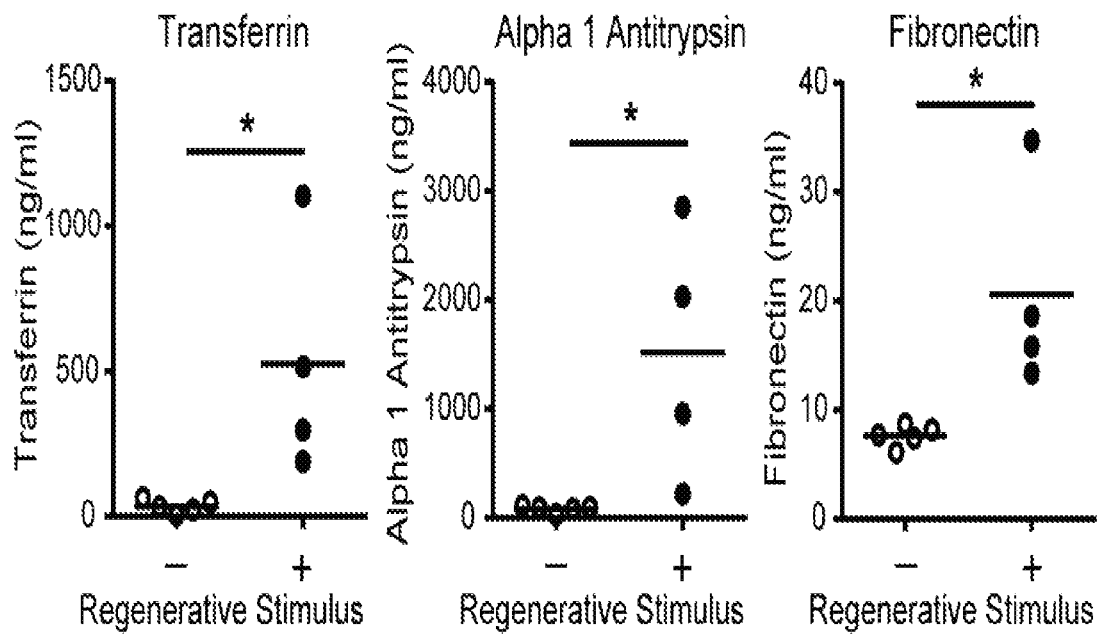
FIG. 12C provides graphs measuring the levels of different hepatocyte blood markers 80 days after implantation with engineered tissue seeds, in mice with or without regenerative stimuli. Transferrin (left), alpha-1-antitrypsin (middle), and fibronectin (right) were all measured in ng/ml. *=p<0.05 ***=p<0.001.

To evaluate the functional characteristics of the expanded tissue seeds, the presence of human proteins in the mouse serum was assayed. Human albumin was detectable in mouse serum as early as the first time point (day 3) and rose to a maximum of 43±4 µg/ml in animals with regenerative stimuli (130-fold change over time by the maximum timepoint; FIG. 12A-12B). The maximum human albumin level detected in a single animal with regenerative stimuli was 105 µg/ml. Human serum albumin levels began to diverge between the treatment groups at approximately day 20, and grafts in animals with regenerative stimuli produced significantly greater albumin than those in control animals (FIG. 12A-12B; 10-fold difference at the endpoint of the experiment). Human albumin was significantly greater in animals with regenerative stimuli compared to controls. In addition to human albumin, blood drawn from animals subjected to regenerative stimuli contained significantly elevated levels of human transferrin, alpha-1-antitrypsin, and fibronectin relative to controls (FIG. 12C; p<0.05). These results suggest that human hepatocytes in ectopic tissue seed grafts are functional and produce more human proteins when in the presence of regenerative signals, compared to their counterparts in uninjured animals.

Figure 13A:
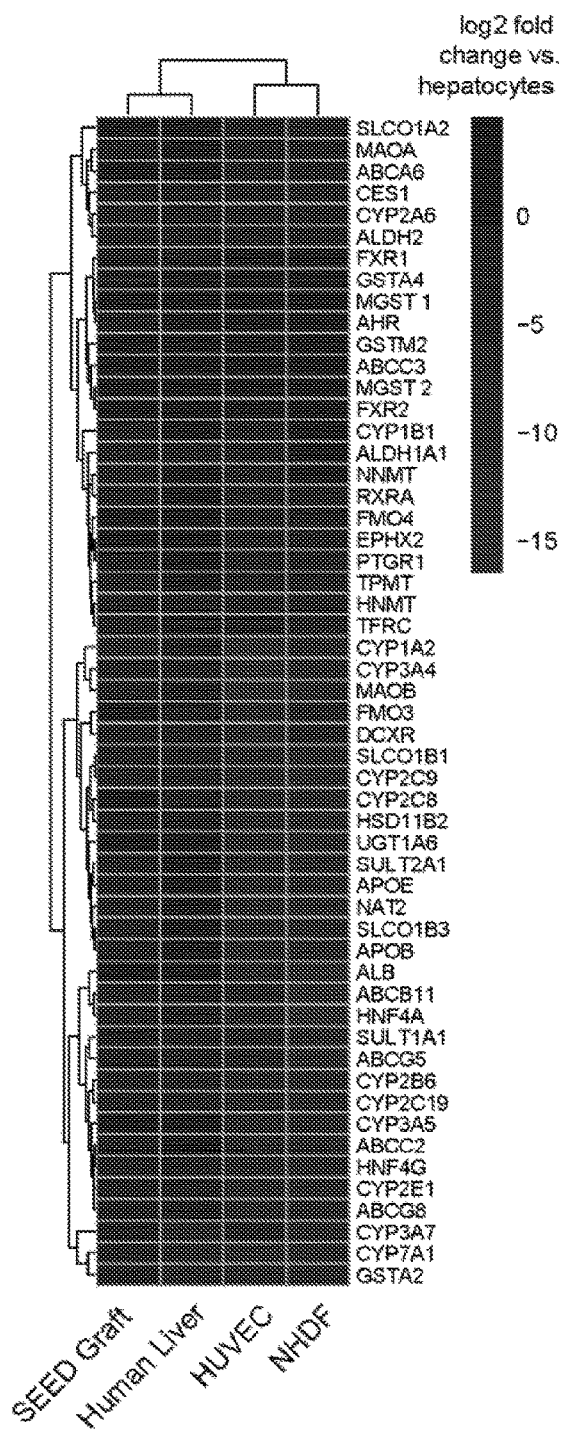
FIG. 13A is a heat map showing 47/50 liver-specific genes were expressed in explanted seed grafts compared to 18/50 genes expressed in HUVEC and NHDF cellular RNA.
Figure 13B:
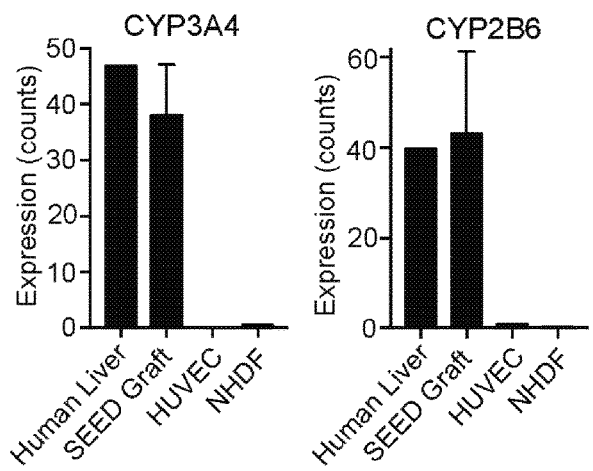
FIGS. 13B-13F show expression of genes from each of the major hepatic drug metabolism pathways expressed in seeds were similar to levels in human liver.
Figure 13C:
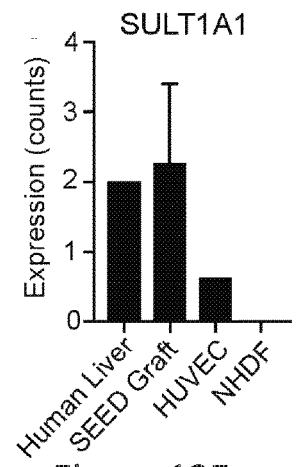
Figure 13D:
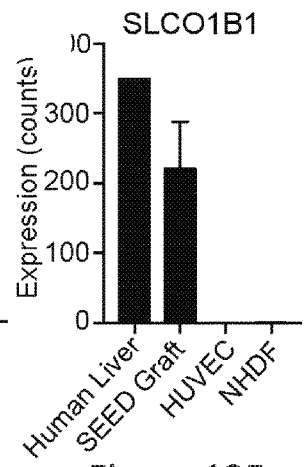
Figure 13E:
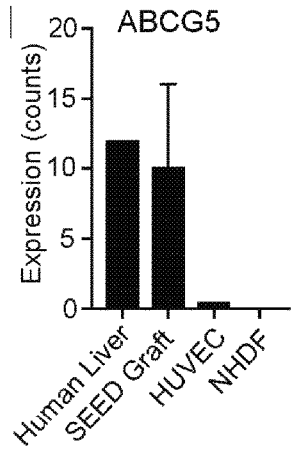
Figure 13F:
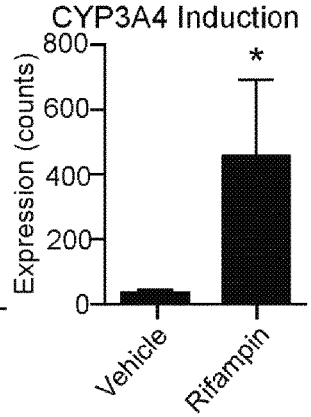

To assess an additional functional axis, as well as gauge the potential utility of tissue seeds for studies of drug metabolism, the expression and induction of human drug-metabolizing enzymes and other key liver-specific genes (i.e., transcription factors, albumin) were characterized in expanded grafts. RNA was collected from grafts explanted from injured host mice, as well as samples of human liver, and human primary hepatocytes, HUVEC and NHDF controls for RNA-Seq analysis. The expression levels of 50 genes that represent varying hepatic gene classes (e.g. CYP3A4 and 2B6 for cytochrome P450 activity, SULT1A1/2A1 for sulfotransferase/Phase II activity, SLCO1A2/1B1 for anion transporter activity, ABCB/ABCG for ATP-binding transporters, APOB/APOE for lipoprotein biosynthesis, ALB for biosynthesis, HNF4A/G as key transcription factors) were assessed in both human liver and primary human hepatocytes control RNA samples (transcript count ratio >1e-6). Read counts across groups were normalized to human primary hepatocytes controls to create an expression heat map (FIG. 13A). 47/50 of these liver-specific genes were expressed in explanted seed grafts, compared to 18/50 genes expressed in unexpanded HUVEC and NHDF RNA samples. Genes from each of the major hepatic drug metabolism pathways were generally expressed in grafts at similar levels to human liver, such as Phase I cytochrome P450 enzymes (FIG. 13B), Phase II enzymes such as sulfotransferases (FIG. 13C), and Phase III anion and ATP-binding transporters (FIGS. 13D and 13E). In addition to hepatic gene expression studies, an additional test to assay the ability of the grafts to upregulate key drug metabolism enzymes in response to a known human CYP450 inducer was performed. To this end, Rifampin or vehicle control was administered to animals bearing both expanded grafts and injured livers, the animals were euthanized and RNA was collected from explanted grafts. Rifampin induced CYP34A expression in grafts, a highly liver-specific phenomenon indicative of mature hepatocytes function (FIG. 13F). Together these studies demonstrate that tissue seeds express drug-metabolizing enzymes, and the expression of these enzymes can be enhanced after administration of the known inducer Rifampin.

Next, the transcriptional profile of the grafts was interrogated more globally. Specifically, the Ingenuity Pathway Analysis was used to assess the fraction of genes known to be downstream of given transcription factors that were differentially regulated between hepatic grafts and HUVEC/NHDF control cells. This analysis identified distinct transcriptional regulation in hepatic grafts by hepatocyte transcription factors in the HNF1, 3, and 4 families, as well as C/EBP, compared to HUVEC/NHDF controls (FIG. 14A), which supports the interpretation that the hepatocytes present in the expanded tissue seeds display a lineage-appropriate phenotype. Furthermore, since tissue seeds are composed of primary hepatocytes, HUVECs and NHDFs, expression profiles from each of these three cell types was tested for detection in seeds after expansion. Hierarchical clustering of expression RNA-Seq profiles obtained from samples of expanded tissue seeds, pure human primary hepatocytes, human liver, and pure populations of cultured NHDFs and HUVECs demonstrated that tissue seeds cluster between the primary hepatocytes/human liver samples and non-parenchymal HUVEC/NHDF cell lines, consistent with an intermediate phenotype driven by the presence of each of these three cells types within the expanded graft (FIG. 14B).

Taken together, the results demonstrate that human hepatocytes in ectopic tissue seed grafts retain a hepatic phenotype and are functional, as characterized by synthesis and drug metabolism, two major axes of hepatic function that are necessary for life.

Characterization of Hepatic Graft Morphology

Figures 15A, 15B, 15C, 15D:
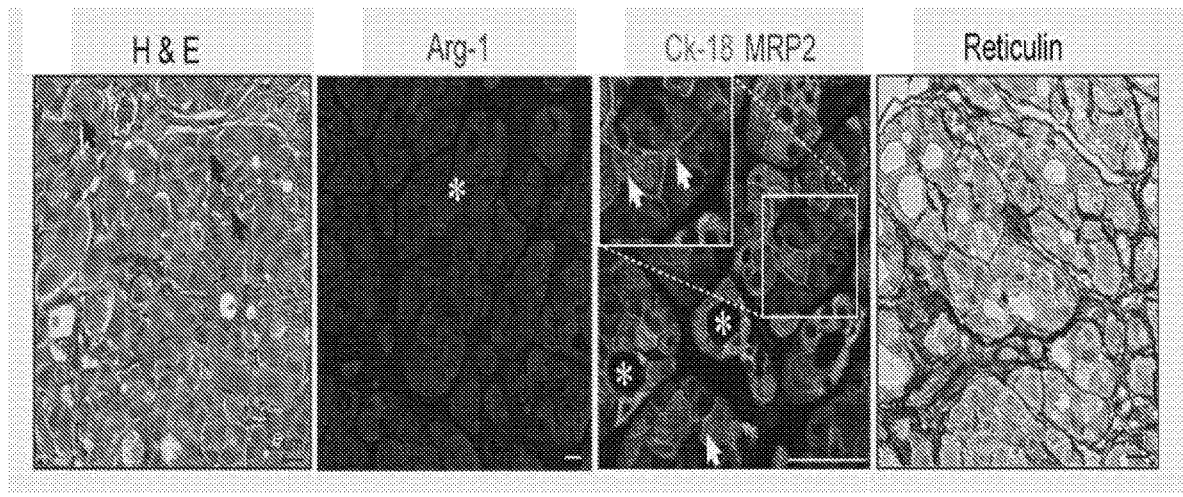
FIGS. 15A-15D are representative images of immunohistochemical staining of engineered tissue seed grafts from animals with regenerative stimuli scarified 80 days after implantation. All scale bars are 25 µm.

Next, the ability of cells to self-organize in response to the presence of regenerative stimuli as the tissue seeds expanded was determined. Immunohistological characterization revealed that the expanded tissue seeds in animals with regenerative stimuli contained densely packed polyhedral cells resembling hepatocytes, many of which were binucleated (FIG. 15A; Hematoxylin & Eosin). These cells stained positively for Ck-18 and Arg-1, both of which are normally expressed in human hepatocytes (FIG. 15B-15C). Graft hepatocytes in expanded seeds were organized into dense aggregate-like units that in some cases exhibited structure reminiscent of hepatic cords in the normal human liver (FIG.

15B, white star). Furthermore, hepatic units in expanded seeds were arranged within a syncytium of interconnected lacunae containing endovascular stroma and lined with collagen III, which lines hepatic cords in the space of Disse in the human liver (FIG. 15D, Reticulin stain). In addition, tissue seed graft sections stained with multidrug resistance-associated protein 2 (MRP2, also known as ABCC2), which is selectively transported to the apical (i.e., canalicular) domain of hepatocytes, revealed that hepatocytes in expanded liver seeds were polarized. Tissue seed grafts also exhibited bile canalicular-like structures between adjacent hepatocytes characteristic of normal liver structure (FIG. 15C, white arrows), as well as larger vacuolar structures lined with MRP2 (FIG. 15C, white stars).

Figures 15E, 15F:
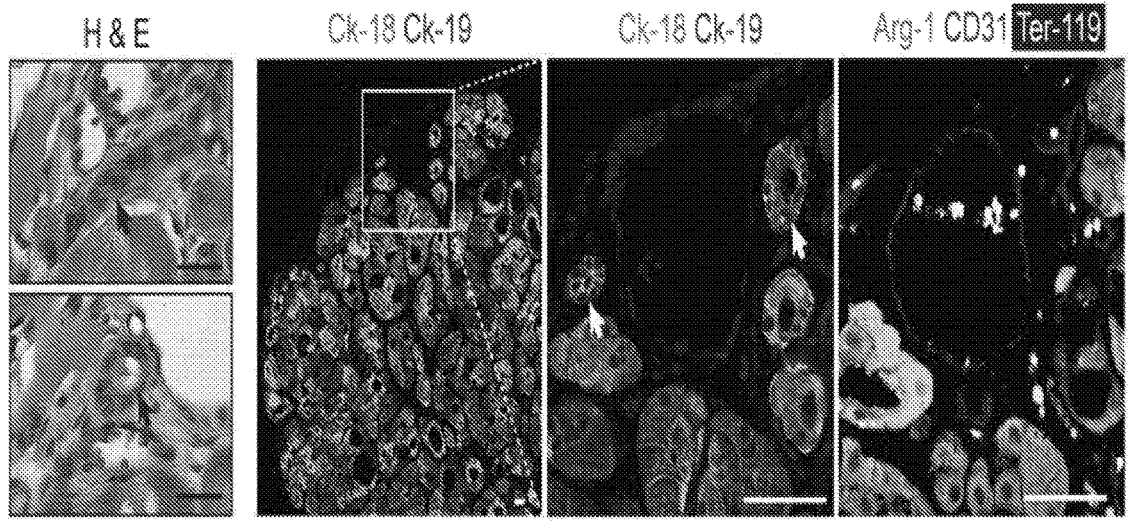
FIG. 15E shows representative images of engineered tissue seed grafts stained with hematoxylin and eosin 80 days after implantation in animals with regenerative stimuli. The arrows point to duct-like structures resembling bile ducts. Scale bars are 25 µm.
FIG. 15F shows representative images of immunostained engineered tissue seed grafts 80 days after implantation in animals with regenerative stimuli. The left and center images show Ck-18 and Ck-19 stained grafts. The right image shows Arg-1, CD31, and Ter-119 stained grafts. All scale bars are 25 µm.
Figure 16:
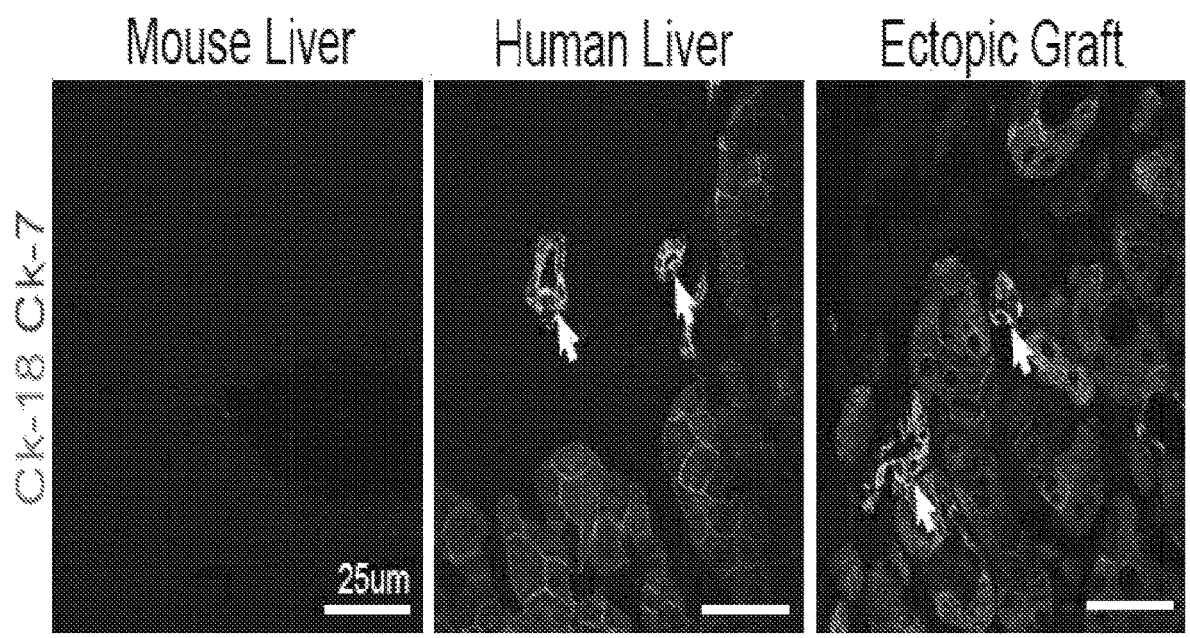
FIG. 16 shows images of immunostained tissues, including a mouse liver (left), human liver (middle), and an engineered tissue seed graft (right), stained for Ck-18 and Ck-7. All scale bars are 25 µm.

Further characterization with hematoxylin and eosin staining revealed that expanded tissue seed grafts also contained duct-like structures resembling bile ducts (FIG. 15E, arrows). To further examine whether biliary epithelial-like cells were present in ectopic grafted tissues, tissue sections were immunohistochemically stained for expression of both Ck-18 (a cytokeratin expressed in both hepatocytes and biliary epithelial cells) and Ck-19 (a cytokeratin expressed in biliary epithelial cells but not hepatocytes). Cells organized in ductal structures stained positively for both Ck-18 and Ck-19, suggesting that these cells exhibit biliary epithelial-like characteristics (FIG. 15F, left and center). Notably, Ck-18 and Ck-19 double-positive ductal structures were typically located within connective tissue and adjacent to huCD31-positive blood vessels, many of which contained Ter-119 positive erythroid cells (FIG. 15F, right). To further confirm both the biliary epithelial cell-like phenotype and whether these cells were of human origin, tissue sections were stained for human Ck-18 and a second cytokeratin expressed on biliary epithelial cells but not hepatocytes, human Ck-7. Ungrafted mouse control livers did not stain with either human marker, whereas positive control human liver tissue contained Ck-18 and Ck-7 double-positive cells in ductal structures (FIG. 16). Ductal structures in ectopic grafts stained positive for both Ck-18 and Ck-7, further confirming that they were comprised of human cells with an epithelial cell phenotype (FIG. 16). These results demonstrate the presence of human biliary epithelial-like cells that have self-assembled to form ductal-like structures at an ectopic location within human tissue seeds, and these ductal structures are commonly associated with other classic features of portal triads, such as vasculature and connective tissue. Taken together, pre-patterned hepatocytes in tissue seeds that were implanted in animals exposed to regenerative stimuli self-assembled upon expansion to create densely packed ectopic hepatic tissue that exhibit several microstructural hallmarks typically associated with human liver.

Concomitant Expansion of Vessels Containing Human Endothelial Cells

Figure 17A:
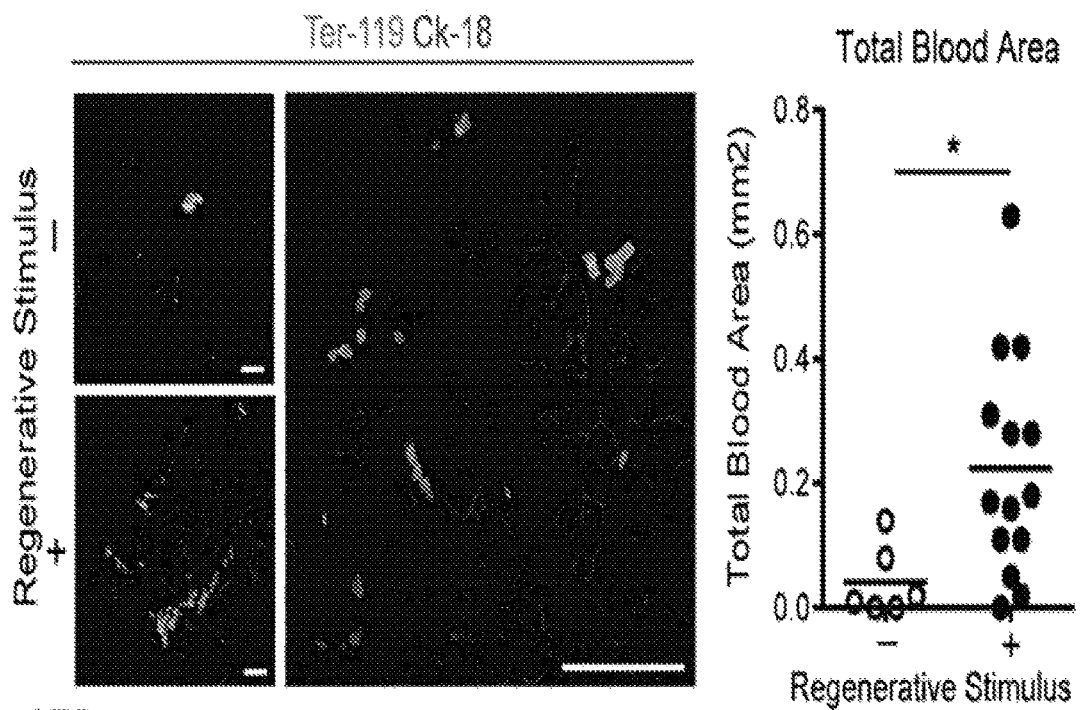
FIG. 17A depicts the presence of blood cells in the engineered tissue seed grafts. The left images are representative of immunostained engineered tissue seed grafts 80 days after implantation in animals with or without regenerative stimuli, stained for Ter-119 (erythrocyte marker) and Ck-18. The right graph shows total blood area measured in $mm^2$, in engineered tissue seed grafts from mice with or without regenerative stimuli, 80 day post-implantation. All scale bars are 25 µm.

The tissue seeds were then analyzed to determine whether interconnected lacunae in tissue seed grafts contained red blood cells and whether regenerative cues would promote expansion of the blood pool. Numerous cells resembling red blood cells in lacunae of tissue seed grafts by H&E staining were noted (FIG. 15A), and the identity of such cells was confirmed by staining for Ter-119, an erythrocyte marker (FIG. 17A). Total blood area was quantified and it was observed that grafts from animals subjected to liver injury contained significantly more blood compared to those from control animals (FIG. 17A, $p<0.05$), suggesting that the blood pool coordinately expanded with the expansion of hepatic tissue seeds in animals with regenerative stimuli.

Figure 17B:
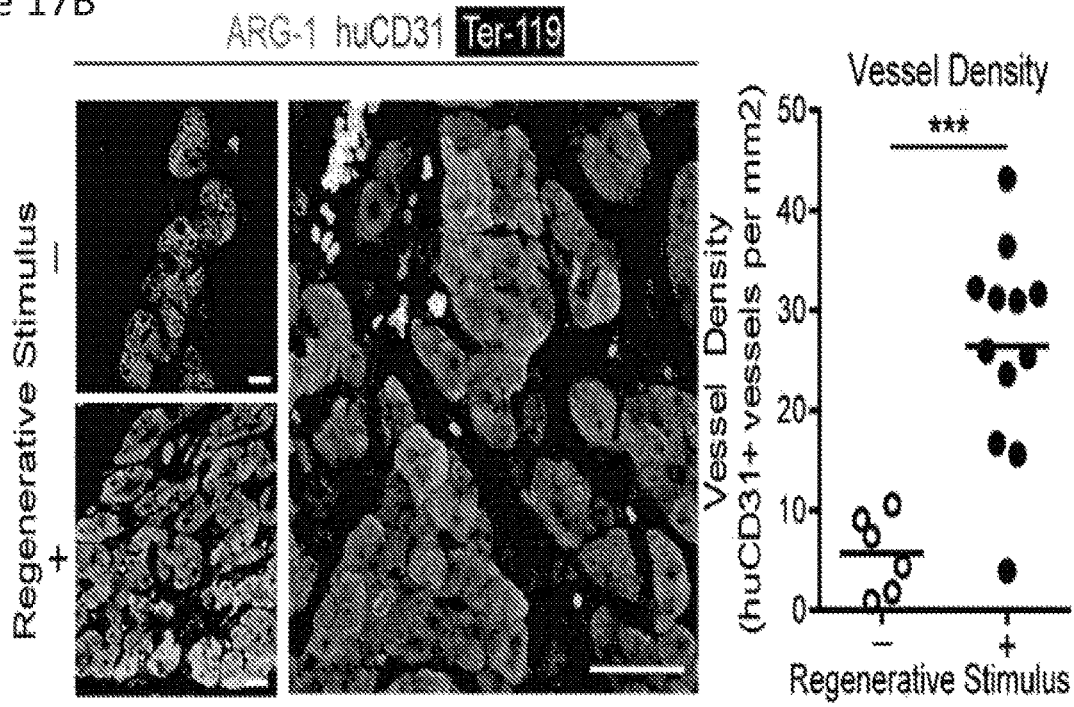
FIG. 17B depicts the expansion of endothelial cells in the engineered tissue seed grafts. The left images are representative of immunostained engineered tissue seed grafts 80 days after implantation in animals with or without regenerative stimuli, stained for Arg-1, human CD31, and Ter-119. The right graph shows vessel density as measured by huCD31+vessels/$mm^2$. All scale bars are 25 µm.
Figure 18:
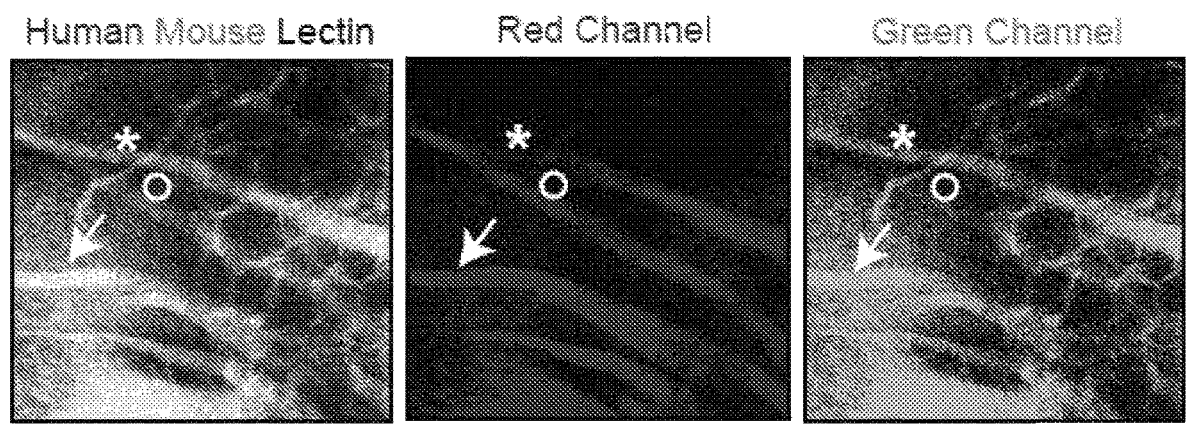
FIG. 18 provides images showing seeds contained vessels lined with both human and mouse endothelium (arrow, section of vessel containing both human and mouse endothelium; open circle, section of vessel with primarily human endothelium; asterisk, section of vessel with primarily mouse endothelium). Seeds were engrafted into FNRG animals with liver injury, cleared using CLARITY, and incubated with lectins that bind human (middle image/red channel) or mouse (right image/green channel).
Figure 19:
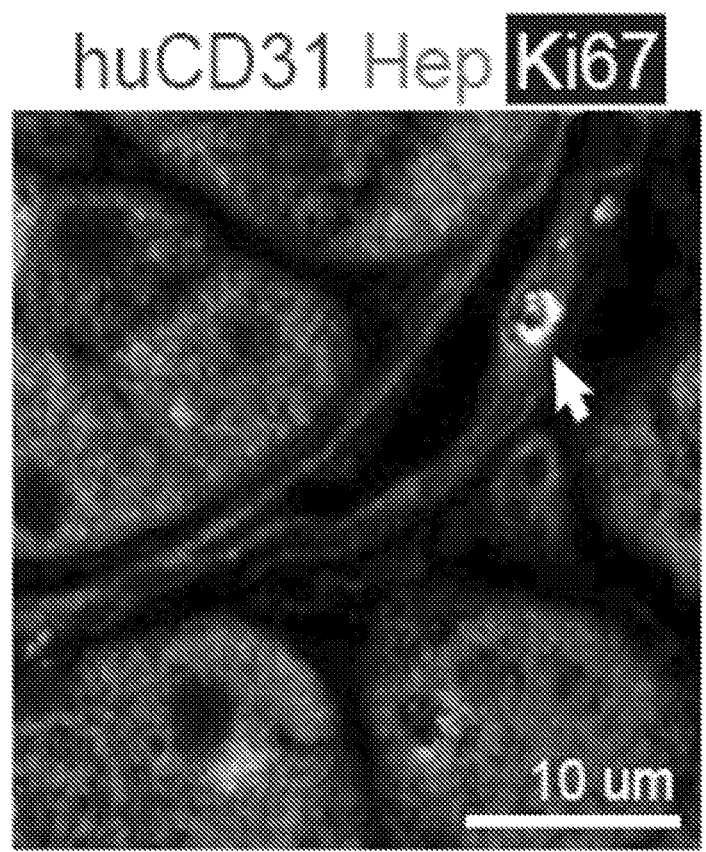
FIG. 19 is a representative image of an engineered tissue seed graft immunostained for huCD31 and Ki67 80 days after implantation in mice with regenerative stimuli. The arrow points to a rare double positive cell.

The presence of organized red blood cells in expanded tissue seeds suggested that vascular networks might be present in these grafts. The ability of human endothelial cells within the tissue seeds to also expand in response to regenerative cues was investigated. To test these hypotheses, graft sections were immunostained with antibodies against human CD31 (endothelial cells), Ter-119, and Arg-1. Numerous vessels lined in part by human endothelial cells were identified throughout the grafts in injured animals (FIG. 17B). Incubation of explanted graft sections in a solution containing lectins that bind specifically to human or mouse endothelium demonstrated that vessels were lined with both human and mouse endothelial cells (FIG. 18). In many cases, these vessels contained Ter-119-positive erythroid cells (FIG. 17B). Blood vessels lined with human CD31-positive endothelial cells were located in the lacunae between and within hepatic units (FIG. 17B, center). Grafts in hosts with regenerative stimuli included more vessels containing human endothelial cells compared to grafts in control animals (FIG. 17B, $p<0.01$). Ki67-positive human endothelial cells were present, but rare (generally less than one Ki67 and huCD31 double-positive cell at the graft faces of all 1 mm sections), suggesting most endothelial cells were not undergoing active cell cycle progression at the time of tissue explant (FIG. 19). Taken together, these results demonstrate that vascular networks carrying blood coordinately expanded with tissue seed hepatic mass in animals with regenerative stimuli.

Tissue Seed Architecture Impacts Expansion in Response to Regenerative Stimuli

Figure 20A:
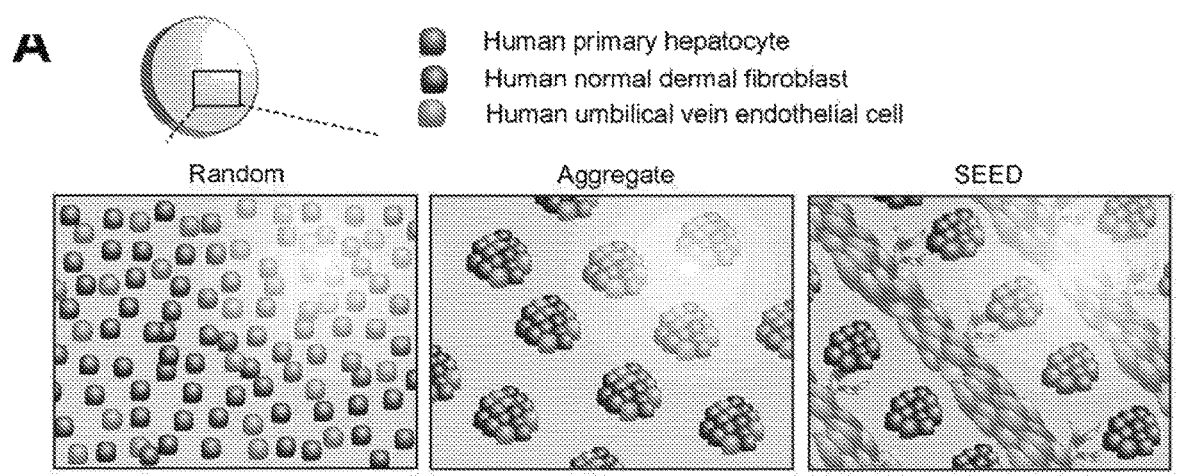
FIGS. 20A-20E show tissue architecture impacts function of seeds after expansion.
Figure 20B:
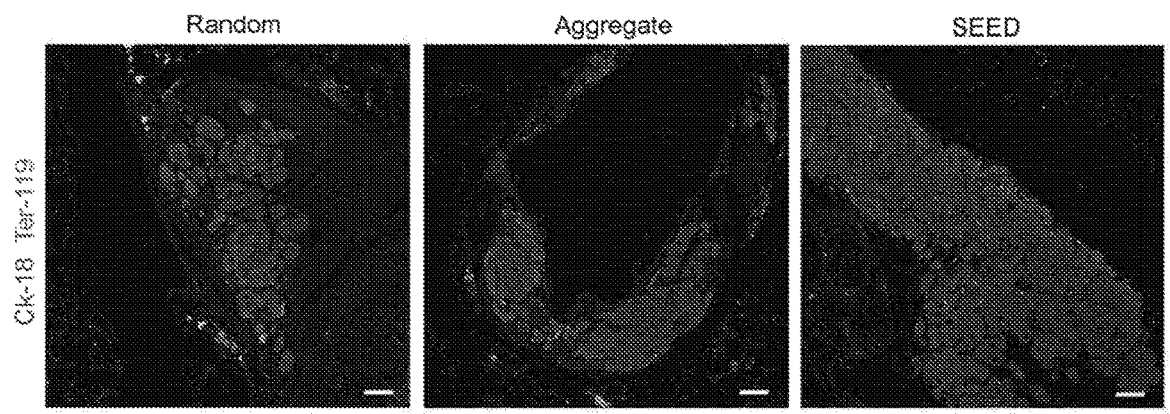
Figure 20C:
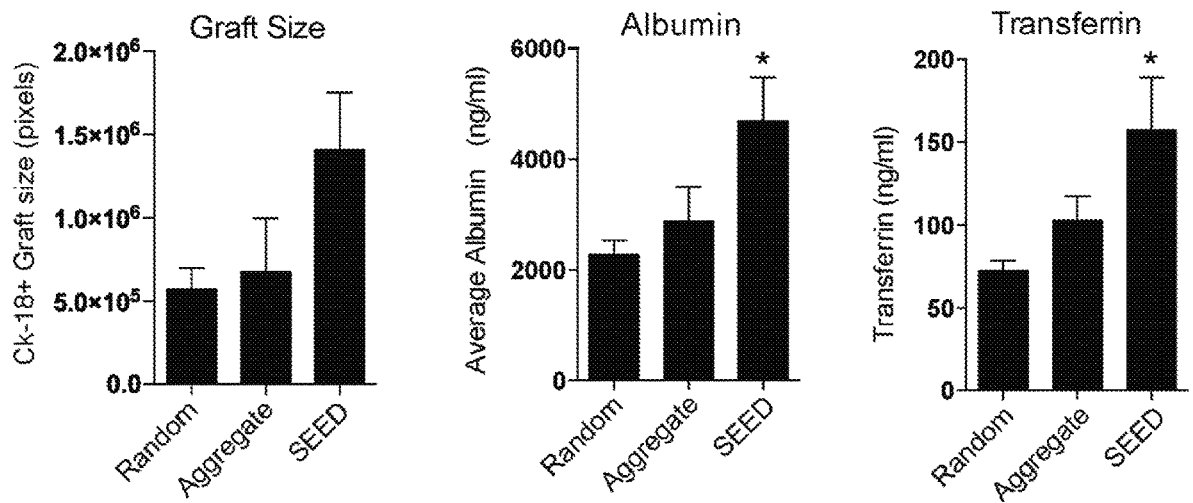
Figure 20D:
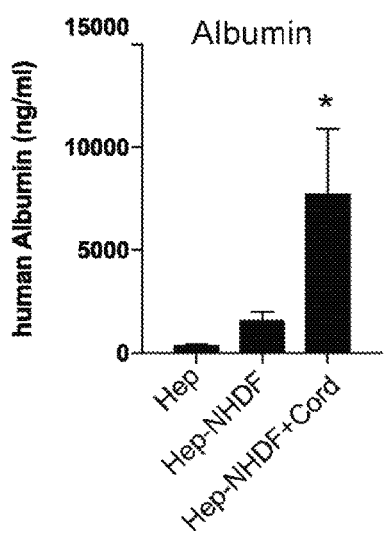

Since tissue architecture ultimately defines the cell-cell contacts and paracrine signaling gradients that drive cellular phenotype and function, the impact of the relative cellular positioning in seeds on expansion in response to regenerative stimuli was tested. Specifically, it was analyzed whether the tissue seeds could be used to dissect of the role of architectural cellular patterning in mediating implant expansion in response to regenerative stimuli. Three constructs were generated using varying arrangements of human hepatocytes, endothelial cells, and stromal cells. These configurations included 1) all three cell types randomly organized as single cells within fibrin hydrogels, 2) all three cell types aggregated to create tri-cell aggregates, and suspended randomly within fibrin hydrogels, and 3) the original tissue seed architecture in which hepatocytes and stromal cells were patterned in aggregates and embedded in fibrin alongside organized endothelial cords (FIG. 20A). Constructs were implanted in the mesenteric fat of FNRG mice, and NTBC was cycled on/off to induce liver damage in all groups. Ck-18+ hepatic graft size of explanted grafts appeared to increase in animals with tissue seeds, but this difference did not reach significance (FIGS. 20B-20C). Nonetheless, human tissue graft function, as measured by the levels of human albumin and transferrin in mouse serum, was significantly enhanced in tissue seed constructs (FIG. 20C, middle and right). To further assess the relative importance of the inclusion of different cell types in mediating seed expansion, NHDFs and/or endothelial cells were removed, respectively, from the seed constructs prior to implantation in FNRG mice and initiating liver injury. Each cellular element in the seeds had a positive impact on human albumin produced in the mouse serum, and this effect reached significance in the presence of all three cell types (FIG. 20D).

Figure 20E:
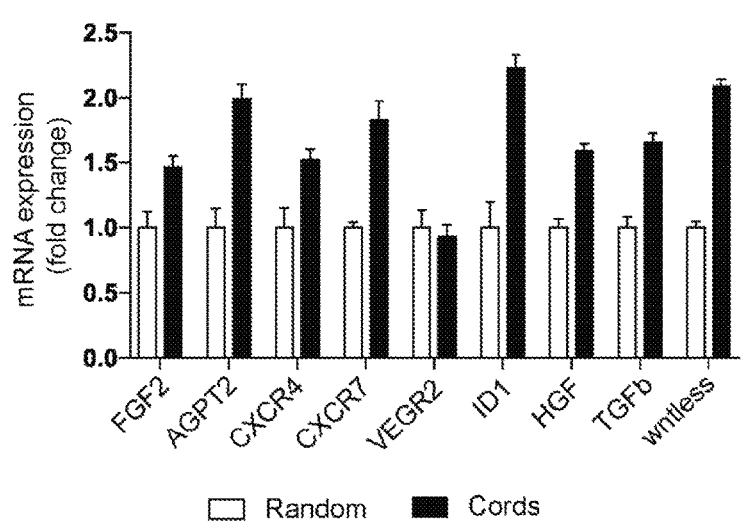

Finally, the mechanism by which cell patterning might play a role in tissue expansion was explored. Tissue seeds containing either randomly organized endothelial cells or endothelial cells patterned in endothelial cords were created and the expression of key 'angiocrine' genes, which have been shown previously to be upregulated in endothelial cells and enhance hepatocyte proliferation during liver regeneration (Ding, B. S., et al., Nature, Vol. 505: 97-102, 2014; Ding, B. S., et al., Nature, Vol. 468: 310-315, 2010), was analyzed immediately after cord formation in vitro. mRNA expression of multiple angiocrine factors were upregulated in tissues containing patterned endothelial cords compared to those with randomly organized endothelial cells (FIG. 20E). These data suggest that expansion of tissue seeds may be driven in part by enhanced expression of angiocrine signals. Together, these analyses demonstrate that tissue architecture influences implant expansion, and that the observed tissue seed expansion may be partially mediated by enhanced expression of angiocrine cues.

EQUIVALENTS

Numerous modifications and alternative embodiments of the present disclosure will be apparent to those skilled in the art in view of the foregoing description. Accordingly, this description is to be construed as illustrative only and is for the purpose of teaching those skilled in the art the best mode for carrying out the present disclosure. Details of the structure may vary substantially without departing from the spirit of the disclosure, and exclusive use of all modifications that come within the scope of the appended claims is reserved. It is intended that the present disclosure be limited only to the extent required by the appended claims and the applicable rules of law.

All literature and similar material cited in this application, including, patents, patent applications, articles, books, treatises, dissertations, web pages, figures and/or appendices, regardless of the format of such literature and similar materials, are expressly incorporated by reference in their entirety. In the event that one or more of the incorporated literature and similar materials differs from or contradicts this application, including defined terms, term usage, described techniques, or the like, this application controls. Such equivalents are intended to be encompassed by the following claims.

The invention claimed is:

1. An ex vivo engineered tissue seed suitable for implantation in a host, comprising
   (a) a patterned biomaterial comprising one or more endothelial cell cords comprising primary human endothelial cells embedded in a biocompatible hydrogel scaffold; and
   (b) hepatocyte aggregates formed by coculturing a first population of cells comprising primary human hepatocytes and a second population of cells comprising human fibroblast cells,
   wherein the hepatocyte aggregates are combined with the patterned biomaterial, and wherein the hepatocyte aggregates are not in direct contact with the endothelial cell cords, thereby forming an engineered tissue seed suitable for implantation in a host.

2. The engineered tissue seed of claim 1, which expands in response to a regeneration cue, following implantation in the host.

3. The engineered tissue seed of claim 1, wherein liver parenchyma in the engineered tissue seed expands in response to regeneration cues, following implantation in the host.

4. The engineered tissue seed of claim 1, wherein vasculature in the engineered tissue seed expands in response to regeneration cues, following implantation in the host.

5. The engineered tissue seed of claim 1, which expands about 50-fold in situ, following implantation in the host.

6. The engineered tissue seed of claim 1, which secretes a hepatocyte blood factor selected from the group consisting of albumin, transferrin, alpha-1-antitrypsin, and fibronectin, or a combination thereof, following implantation in the host.

7. The engineered tissue seed of claim 1, which expands to form densely packed hepatocytes, form duct-like structures resembling bile ducts, form biliary epithelial-like cells, form blood vessels, or any combination thereof, following implantation in the host.

8. The engineered tissue seed of claim 1, which expands in response to paracrine signaling between cells in the engineered tissue seed, following implantation in the host.

9. The engineered tissue seed of claim 1, which expands in response to a regeneration cue from the host, wherein the regeneration cue is due to an injury, disease or infection in the host, or occurs during native development of the host.

10. The engineered tissue seed of claim 1, wherein the regeneration cue is a growth factor or cytokine.

11. The engineered tissue seed of claim 1, further comprising a small molecule or growth factor which stimulates or enhances expansion of the engineered tissue seed, following implantation in a host.

12. The engineered tissue seed of claim 1, wherein the scaffold comprises one or more channels, wherein the channels are in parallel or non-parallel formation.

13. The engineered tissue seed of claim 12, wherein the channels are organized with specific branch patterns selected from rectilinear grids, bifurcated trees, 2D and 3D organizations.

14. The engineered tissue seed of claim 1, wherein the seed is about 10-30 mm in diameter.

15. The engineered tissue seed of claim 1, wherein the endothelial cell cords consist of endothelial cells.

16. The engineered tissue seed of claim 1, which expands in response to liver injury following implantation in the host.

17. An ex vivo engineered tissue seed suitable for implantation in a host, comprising
   (a) a patterned biomaterial comprising a plurality of endothelial cell cords comprising primary human endothelial cells embedded in a biocompatible hydrogel scaffold, wherein the plurality of endothelial cell cords are organized in a repeating and parallel arrangement; and
   (b) hepatocyte aggregates formed by coculturing a first population of cells comprising primary human hepatocytes and a second population of cells comprising human fibroblast cells,
   wherein the hepatocyte aggregates are combined with the patterned biomaterial, thereby forming an engineered tissue seed suitable for implantation in a host.

18. The engineered tissue seed of claim 17, which expands about 50-fold in situ, following implantation in the host.

19. The engineered tissue seed of claim 17, which expands in response to liver injury following implantation in the host.

20. The engineered tissue seed of claim 17, which expands to form densely packed hepatocytes, form duct-like structures resembling bile ducts, form biliary epithelial-like cells, form blood vessels, or any combination thereof, following implantation in the host.

21. The engineered tissue seed of claim 17, wherein the endothelial cell cords consist of endothelial cells.

22. The engineered tissue seed of claim 17, wherein the hepatocyte aggregates are not in direct contact with the endothelial cell cords.

23. The engineered tissue seed of claim 17, wherein the seed is about 10-30 mm in diameter.

24. The engineered tissue seed of claim 17, wherein the hepatocyte aggregates are micropatterned between the endothelial cell cords.

25. The engineered tissue seed of claim 24, wherein the hepatocyte aggregates are not in direct contact with the endothelial cell cords.

26. An ex vivo engineered tissue seed suitable for implantation in a host, the engineered tissue seed comprising:
   (a) one or more human endothelial cell cords; and
   (b) one or more hepatocyte aggregates, wherein each hepatocyte aggregate comprises a first population of cells comprising primary human hepatocytes and a second population of cells comprising human fibroblast cells,
      wherein the one or more human endothelial cell cords and the one or more hepatocyte aggregates are each in a biocompatible scaffold, and wherein the one or more hepatocyte aggregates are not in direct contact with the one or more human endothelial cell cords.

27. An ex vivo engineered tissue seed suitable for implantation in a host, the engineered tissue seed comprising:
   (a) a plurality of human endothelial cell cords organized in a repeating and parallel arrangement; and
   (b) one or more hepatocyte aggregates, wherein each hepatocyte aggregate comprises a first population of cells comprising primary human hepatocytes and a second population of cells comprising human fibroblast cells,
      wherein the plurality of human endothelial cell cords and the one or more hepatocyte aggregates are each in a biocompatible scaffold.

28. The engineered tissue seed of claim 27, wherein the hepatocyte aggregates are micropatterned between the endothelial cell cords.

29. The engineered tissue seed of claim 28, wherein the hepatocyte aggregates are not in direct contact with the endothelial cell cords.

* * * * *